(12) United States Patent
Scherman et al.

(10) Patent No.: US 9,439,868 B2
(45) Date of Patent: Sep. 13, 2016

(54) SUPRAMOLECULAR CAPSULES

(75) Inventors: Oren Alexander Scherman, Cambridge (GB); Roger Coulston, Cambridge (GB); Christopher Abell, Cambridge (GB); Jing Zhang, Cambridge (GB)

(73) Assignee: CAMBRIDGE ENTERPRISE LIMITED, Cambridge (GB)

( * ) Notice: Subject to any disclaimer, the term of this patent is extended or adjusted under 35 U.S.C. 154(b) by 0 days.

(21) Appl. No.: 14/233,417

(22) PCT Filed: Jul. 25, 2012

(86) PCT No.: PCT/GB2012/051787
§ 371 (c)(1),
(2), (4) Date: Jan. 17, 2014

(87) PCT Pub. No.: WO2013/014452
PCT Pub. Date: Jan. 31, 2013

(65) Prior Publication Data
US 2014/0170214 A1 Jun. 19, 2014

(30) Foreign Application Priority Data

Jul. 26, 2011 (GB) .................................. 1112893.1
Feb. 8, 2012 (GB) .................................. 1202127.5

(51) Int. Cl.
| | | |
|---|---|---|
| *A61K 9/48* | (2006.01) | |
| *A61K 47/48* | (2006.01) | |
| *C08G 83/00* | (2006.01) | |
| *A61K 9/50* | (2006.01) | |
| *A01N 25/28* | (2006.01) | |
| *B01J 13/14* | (2006.01) | |
| *C11D 17/00* | (2006.01) | |
| *C09B 69/10* | (2006.01) | |
| *B82Y 5/00* | (2011.01) | |
| *A61K 35/12* | (2015.01) | |

(52) U.S. Cl.
CPC ............ *A61K 9/4816* (2013.01); *A01N 25/28* (2013.01); *A61K 9/5031* (2013.01); *A61K 9/5089* (2013.01); *A61K 47/48961* (2013.01); *B01J 13/14* (2013.01); *B82Y 5/00* (2013.01); *C08G 83/008* (2013.01); *C09B 69/109* (2013.01); *C11D 17/0039* (2013.01); *A61K 2035/128* (2013.01)

(58) Field of Classification Search
CPC ..................... A61K 47/48961; A61K 9/5031; C08G 83/008; A01N 25/28
USPC ....................................................... 424/451
See application file for complete search history.

(56) References Cited

U.S. PATENT DOCUMENTS

| 6,911,572 B1 | 6/2005 | Bruhn et al. |
|---|---|---|
| 7,060,498 B1 | 6/2006 | Wang |
| 8,378,059 B2 | 2/2013 | Rauwald et al. |
| 2002/0133003 A1 | 9/2002 | Kim et al. |
| 2004/0247680 A1 | 12/2004 | Farokhzad et al. |
| 2005/0250551 A1 | 11/2005 | Helle |
| 2005/0250881 A1 | 11/2005 | Gref et al. |
| 2006/0154254 A1 | 7/2006 | Kim et al. |
| 2006/0292570 A1 | 12/2006 | Keinan |
| 2010/0247477 A1* | 9/2010 | Rauwald et al. ............ 424/78.3 |
| 2010/0254890 A1 | 10/2010 | Yang et al. |

FOREIGN PATENT DOCUMENTS

| JP | 2007-211060 A | 8/2007 | |
|---|---|---|---|
| WO | 99/64485 A1 | 12/1999 | |
| WO | 2005/023816 A2 | 3/2005 | |
| WO | WO 2005/112890 A1 | 12/2005 | |
| WO | 2007/046575 A1 | 4/2007 | |
| WO | 2007/106144 A1 | 9/2007 | |
| WO | 2008/096360 A2 | 8/2008 | |
| WO | 2009071899 * | 6/2009 | ............ C08G 83/00 |
| WO | WO 2009/071899 A2 | 6/2009 | |
| WO | 2011/077099 A2 | 6/2011 | |
| WO | 2013/014452 A1 | 1/2013 | |

OTHER PUBLICATIONS

Kola et al.; title: A detailed description of synthetic and natural polymers which are used in the formulation of sustained release drug delivery system: review; Journal of chemical and pharmaceutical sciences, vol. 6(3), pp. 161-169; July-September issue, 2013.*
Nechifor et al., Title: The size distribution of core shell polymeric capsules as revealed by low-field NMR diffusometry, Applied Magnetic Resonance, vol. 40, pp. 205-211, published online Feb. 12, 2011.*
Appel et al; "Supramolecular Cross-Linked Networks via Host—Guest Complexation with Cucurbit[8]uril;" J. Am. Chem. Soc.; 2010; col. 132; pp. 14251-14260.
Patra et al; "Formation and Size Tuning of Colloidal Microcapsules via Host-Guest Molecular Recognition at the Liquiid-Liquid Interface;" Langmuir; 2009; vol. 25; No. 24; pp. 13852-13854.
Wang et al; "Stepwise Assembly of the Same Polyelectrolytes Using Host-Guest Interaction to Obtain Microcapsules with Multiresponsive Properties;" Chem. Mater.; 2008; vol. 20; pp. 4194-4199.
Hwang et al; "Noncovalent Immobilization of Proteins on a Solid Surface by Cucurbit[7]uril-Ferrocenemethylammonium Pair, a Potential Replacement of Biotin-Avidin Pair;" J. Am. Chem Soc.; 2007; vol. 129; pp. 4170-4171.

(Continued)

*Primary Examiner* — Ali Soroush
*Assistant Examiner* — Yanzhi Zhang
(74) *Attorney, Agent, or Firm* — Oliff PLC

(57) ABSTRACT

Provided is a capsule having a shell of material that is a supramolecular cross-linked network. The network is formed from a host-guest complexation of cucurbituril (the host) and one or more building blocks comprising suitable guest functionality. The complex non-covalently crosslinks the building block and/or non-covalently links the building block to another building block thereby forming the supramolecular cross-linked network. The capsules are obtained or obtainable by the complexation of a composition comprising cucurbituril and one or more building blocks having suitable cucurbituril guest functionality thereby to form a supramolecular cross-linked network.

33 Claims, 17 Drawing Sheets

(56) References Cited

OTHER PUBLICATIONS

Taylor et al; "Precise Subnanometer Plasmonic Junctions for SERS within Gold Nanoparticle Assemblies Using Cucurbit[n]uril 'Glue';" ACS Nano; 2011; vol. 5; No. 5; pp. 3878-3887.
Nov. 7, 2011 Search Report issued in British Patent Application No. 1112893.1.
Mar. 14, 2012 Search Report issued in British Patent Application No. 1202127.5.
Nov. 29, 2012 Search Report issued in International Patent Application No. PCT/GB2012/051787.
Nov. 29, 2012 Written Opinion issued in International Patent Application No. PCT/GB2012/051787.
Abraham et al; "Microfluidic Synthesis of Reversibly Swelling Porous Polymeric Microcapsules with Controlled Morphology;" Adv. Mater. 2008; vol. 20; pp. 2177-2182.
Ameloot et al; "Interfacial synthesis of hollow metal-organic framework capsules demonstrating selective permeability;" Nature Chemistry; 2011; DOI: 10.1038/NCHEM.1026; pp. 1-6.
An et al; pH Controlled Permeability of Lipid/Protein Biometric Microcapsules; Biomacromolecules; 2006; vol. 7; pp. 580-585.
Andrieux et al; "Characterization of Fluorescein Isothiocyanate-Dextrans Used in Vesicle Permeability Studies;" Anal. Chem.; 2002; vol. 74; No. 20; pp. 5217-5226.
Anema et al; "Shell-Isolated Nanoparticle-Enhanced Raman Spectroscopy: Expanding the Versatility of Surface-Enhanced Raman Scattering;" Annu. Rev. Anal. Chem.; 2011; vol. 4; pp. 129-150.
Bush et al; "Charge-Mediated Recognition of N-Terminal Tryptophan in Aqueous Solution by a Synthetic Host;" J. Am. Chem. Soc.; 2005; vol. 127; pp. 14511-14517.
Caruso et al; "Nanoengineering of Inorganic and Hybrid Hollow Spheres by Colloidal Templating;" Science; 1998; vol. 282; pp. 1111-1114.
Cavalieri et al; "Assembly and Functionalization of DNA-Polymer Microcapsules;" ACS Nano; 2009; vol. 3; No. 1; pp. 234-240.
Chiefari et al; "Living Free-Radical Polymerization by Reversible Addition-Fragmentation Chain Transfer: The RAFT Process;" Macromolecules; 1998; vol. 31; pp. 5559-5562.
Comiskey et al; "An electrophoretic ink for all-printed reflective electronic displays;" Nature; 1998; vol. 394; pp. 253-255.
Coulston et al; "Supramolecular gold nanoparticle-polymer composites formed in water with cucurbit[8]uril;" Chem. Commun.; 2011; vol. 47; pp. 164-166.
Cui et al; "Monodisperse Polymer Capsules: Tailoring Size, Shell, Thickness, and Hydrophobic Cargo Loading via Emulsion Templating;" Adv. Funct. Mater.; 2010; vol. 20; 1625-1631.
Danil de Namor et al; "Thermodynamics of Calixarene Chemistry;" Chem. Rev.; 1998; vol. 98; pp. 2495-2525.
De Cock et al; "Polymeric Multilayer Capsules in Drug Delivery;" Angew. Chem. Int. Ed.; 2010; vol. 49; pp. 6954-6973.
Donath et al; "Novel Hollow Polymer Shells by Colloid-Templated Assembly of Polyelectrolytes;" Angew. Chem. Int. Ed.; 1998; vol. 37; No. 16; pp. 2201-2205.
Dsouza et al; "Fluorescent Dyes and Their Supramolecular Host/Guest Complexes with Macrocycles in Aqueous Solution;" Chem. Rev.; 2011; vol. 111; pp. 7941-7980.
Duffy et al; "Rapid Prototyping of Microfluidic Systems in Poly(dimethylsiloxane);" Anal. Chem.; 1998; vol. 70; pp. 4974-4984.
Forster et al; "Infrared, Raman and Resonance Raman Investigations of Methylviologen and its Radical Cation;" Journal of Raman Spectroscopy; 1982; vol. 12; No. 1; pp. 36-48.
Frens et al; "Controlled Nucleation for the Regulation of the Particle Size in Monodisperse Gold Suspensions;" Nature Physical Science; 1973; vol. 241; pp. 20-22.
Garstecki et al; "Formation of droplets and bubbles in a microfluidic T-junction-scaling and mechanism of break-up;" Lab Chip; 2006; vol. 6; pp. 437-446.
Gokel et al; "Crown Ethers: Sensors for Ions and Molecular Scaffolds for Materials and Biological Models;" Chem. Rev.; 2004; vol. 104; pp. 2723-2750.

Granath; "Solution Properties of Branched Dextrans;" Journal of Colloid Science; 1958; vol. 13; pp. 308-328.
Gunther et al; "Multiphase microfluidics: from flow characteristics to chemical and materials synthesis;" Lab Chip; 2006; vol. 6; pp. 1487-1503.
Hermanson et al; "Permeability of silk microcapsules made by the interfacial adsorption of protein;" Phys. Chem. Chem. Phys.; 2007; vol. 9; pp. 6642-6446.
Holtze et al; "Biocompatible surfactants for water-in-fluorocarbon emulsions;" Lab Chip; 2008; vol. 8; pp. 1632-1639.
Huebner et al; "Microdroplets: A sea of applications?;" Lab Chip; 2008; vol. 8; pp. 1244-1254.
Jiao et al; "A Systems Approach to Controlling Supramolecular Architecture and Emergent Solution Properties via Host-Guest Complexation in Water;" J. Am. Chem. Soc.; 2010; vol. 132; pp. 15734-15743.
Jiao et al; "Size Selective Supramolecular Cages from Aryl-Bisimidazolium Derivatives and Cucurbit[8]uril;" Organic Letters; 2011; vol. 13; No. 12; pp. 3044-3047.
Kelly et al; "The Optical Properties of Metal Nanoparticles: The Influence of Size, Shape, and Dielectric Environment;" J. Phys. Chem. B; 2003; vol. 107; pp. 668-677.
Kim et al; "New Cucurbituril Homologues: Syntheses, Isolation, Characterization, and X-ray Crystal Structures of Cucurbit[n]uril (n=5, 7, and 8);" J. Am. Chem. Soc.; 2000; vol. 122; pp. 540-541.
Lagona et al; "The Cucurbit[n]uril Family;" Angew. Chem. Int. Ed.; 2005; vol. 44; pp. 4844-4870.
Link et al; "Size and Temperature Dependence of the Plasmon Absorption of Colloidal Gold Nanoparticles;" J. Phys. Chem. B; 1999; vol. 103; pp. 4212-4217.
Martin et al; "Charged Gold Nanoparticles in Non-Polar Solvents: 10-min Synthesis and 2D Self-Assembly;" Langmuir; 2010; vol. 26; No. 10; pp. 7410-7417.
Mehvar; "Dextrans for targeted and sustained delivery of therapeutic and imaging agents;" Journal of Controlled Release; 2000; vol. 69; pp. 1-25.
Moghaddam et al; "New Ultrahigh Affinity Host-Guest Complexes of Curcurbit[7]uril with Bicycle[2.2.2]octane and Adamantane Guests: Thermodynamic Analysis and Evaluation of M2 Affinity Calculations;" J. Am. Chem. Soc.; 2011; vol. 133; pp. 3570-3581.
Patra et al; "Colloidal Microcapsules: Self-Assembly of Nanoparticles at the Liquid-Liquid Interface;" Chem. Asian J.; 2010; DOI: 10.1002/asia.201000301; pp. 1-13.
Peyratout et al; "Tailor-Made Polyelectrolyte Microcapsules: From Multilayers to Smart Containers;" Angew. Chem. Int. Ed.; 2004; vol. 43; pp. 3762-3783.
Priest et al; "Microfluidic polymer multilayer adsorption on liquid crystal droplets for microcapsule synthesis;" Lab Chip; 2008; vol. 8; pp. 2182-2187.
Rauwald et al; "Correlating Solution Binding and ESI-MS Stabilities by Incorporating Solvation Effects in a Confined Cucurbit[8]uril System;" J. Phys. Chem. B; 2010; vol. 114; pp. 8606-8615.
Rekharsky et al; "Complexation Thermodynamics of Cyclodextrins;" Chem. Rev.; 1998; vol. 98; pp. 1875-1917.
Therberge et al; "Mircodroplets in Microfluidics: An Evolving Platform for Discoveries in Chemistry and Biology;" Angew. Chem. Int. Ed.; 2010; vol. 49; pp. 5846-5868.
Thorsen et al; "Dynamic Pattern Formation in a Vesicle-Generating Microfluidic Device;" Physical Review Letters; 2001; vol. 86; No. 18; pp. 4163-4166.
Utada et al; "Monodisperse Double Emulsions Generated from a Microcapillary Device;" Science; 2005; vol. 308; pp. 537-541.
Xu et al; "Preparation of Highly Monodisperse Droplet in a T-Junction Microfluidic Device;" AIChE Journal; 2006; vol. 52; No. 9; pp. 3005-3010.
Yang et al; "Microfluidic assisted synthesis of multi-functional polycaprolactone microcapsules: incorporation of CdTe quantum dots, $Fe_3O_4$ superparamagnetic nanoparticles and tamoxifen anti-cancer drugs;" Lab Chip; 2009; vol. 9; pp. 961-965.
Lim et al. "Self-Assembled Ternary Complex of Cationic Dendrimer, Cucurbituril, and DNA: Noncovalent Strategy in Developing a Gene Delivery Carrier". Bioconjugate Chem. vol. 13, pp. 1181-1185, 2002.

(56) References Cited

OTHER PUBLICATIONS

Glossary, Drug-Discovery-and-Development, 2012, http:www.dddmag.com/content/glossary-drug-discovery-and-development-terms.
Bosman et al.; "Supramolecular polymers at work;" Materials Today; Apr. 2004; pp. 34-39; vol. 7; Elsevier Ltd.
Sijbesma et al.; "Reversible Polymers Formed from Self-Complementary Monomers Using Quadruple Hydrogen Bonding;" Science; Nov. 28, 1997; pp. 1601-1604; vol. 278; American Association for the Advancement of Science; Washington D.C.
Archer et al.; "Coordination chemistry from monomers to copolymers;" Coordination Chemistry Reviews; 1993; pp. 49-68; vol. 128; Elsevier Sequoia.
Swiegers et al.; "New Self-Assembled Structural Motifs in Coordination Chemistry;" Chem. Rev.; 2000; pp. 3483-3537; vol. 100; American Chemical Society.
Lehn et al.; "Spontaneous assembly of double-stranded helicates from oligobipyridine ligands and copper(I) cations: Structure of an inorganic double helix;" Proc. Natl. Acad. Sci.; May 1987; pp. 2565-2569; vol. 84.
Schutte et al.; "Metallosupramolecular Thin Polyelectrolyte Films;" Angew. Chem. Int. Ed.; 1998; pp. 2891-2893; vol. 37, No. 20; Wiley-VCH Verlag GmbH & Co.
Lohmeijer et al.; "Supramolecular Engineering with Macromolecules: An Alternative Concept for Block Copolymers;" Angew. Chem. Int. Ed.; 2002; pp. 3825-3829; vol. 41, No. 20; Wiley-VCH Verlag GmbH & Co.
Chen et al; "Ruthenuim Bipyridine-Containing Polymers and Block Copolymers via Ring-Opening Metathesis Polymerization;" Macromolecules; 2004; pp. 5866-5872; vol. 37; American Chemical Society.
Zhou et al,; "Synthesis and Characterization of Bis(2,2':6'2"-terpyridine)ruthenium(II)-Connected Diblock Polymers via Raft Polymerization;" Macromolecules; 2005; pp. 4114-4123; vol. 38; American Chemical Society.
Fustin et al.; "Metallo-Supramolecular Block Copolymers:" Advanced Materials; 2007; pp. 1665-1673; vol. 19; Wiley-VCH Verlag GmbH & Co.
Scherman et al.; "Olefin metathesis and quadruple hydrogen bonding: A powerful combination in multistep supramolecular synthesis;" PNAS; Aug. 8, 2006; pp. 11850-11855; vol. 103, No. 32; The National Academy of Sciences of the USA.
Yang et al.; "Supramolecular AB Diblock Copolymers;" Angew. Chem. Int. Ed.; 2004; pp. 6471-6474; vol. 43; Wiley-VCH Verlag GmbH & Co.
Higley et al.; "A Modular Approach toward Block Copolymers;" Chem. Eur. J.; 2005; pp. 2946-2953; vol. 11; Wiley-VCH Verlag GmbH & Co.
Yamauchi et al.; "Combinations of Microphase Separation and Terminal Multiple Hydrogen Bonding in Novel Macromolecules;" J. Am. Chem. Soc.; 2002; pp. 8599-8604; vol. 124; American Chemical Society.
Binder et al.; "Supramolecular Poly(ether ketone)-Polyisobutylene Pseudo-Block Copolymers;" Journal of Polymer Science: Part A: Polymer Chemistry; 2004; pp. 162-172; vol. 42; Wiley Periodicals, Inc.
Sontjens et al.; Stability and Lifetime of Quadruply Hydrogen Bonded 2-Ureido-4[1H]-pyrimidinone Dimers; J. Am. Chem. Soc.; 2000; pp. 7487-7493; vol. 122; American Chemical Society.
Shimizu; "Mini Review-Perspectives on main-chain hydrogen bonded supramolecular polymers;" Polymer International; 2007; pp. 444-452; vol. 56; Society of Chemical Industry.
Behrend et al.; "Justus Liebig's Annalen Der Chemie.;" 1904; pp. 1-37; vol. 339.
Freeman et al.; "Cucurbituril;" J. Am. Chem. Soc.; 1981; pp. 7367-7368; vol. 103; American Chemical Society.
Kim et al.; "Selective Inclusion of a Hetero-Guest Pair in a Molecular Host: Formation of Stable Charge-Transfer Complexes in Cucurbit[8]uril;" Angew. Chem. Int. Ed.; 2001; pp. 1526-1529; vol. 40, No. 8; Wiley-VCH Verlag GmbH.

Sindelar et al.; "Supramolecular Assembly of 2,7-Dimethyldiazapyrenium and Cucurbit[8]uril: A New Fluorescent Host for Detection of Catechol and Dopamine;" Chem. Eur. J.; 2005; pp. 7054-7059; vol. 11; Wiley-VCH Verlag GmbH & Co.
Jeon et al.; "Supramolecular Amphiphiles: Spontaneous Formation of Vesicles Triggered by Formation of a Charge-Transfer Complex in a Host" Angew. Chem. Int. Ed.; 2002; pp. 4474-4476; vol. 41, No. 23; Wiley-VCH Verlag GmbH & Co.
Jeon et al.; "Molecular Loop Lock: A Redox-Driven Molecular Machine Based on a Host-Stablized Charge-Transfer Complex;" Angew. Chem. Int. Ed.; 2005; pp. 87-91; vol. 44; Wiley-VCH Verlag GmbH & Co.
Ko et al.; "Designed Self-Assembly of Molecular Necklaces Using Host-Stabilized Charge-Transfer Interactions;" J. Am. Chem. Soc.; 2004; pp. 1932-1933; vol. 126; American Chemical Society.
Kim et al.; "Growth of poly(pseudorotaxane) on gold using host-stabilized charge-transfer interaction;" Chem. Commun.; 2004; pp. 848-849; The Royal Society of Chemistry.
Jeon et al.; "A [2]Pseudorotaxane-Based Molecular Machine: Reversible Formation of a Molecular Loop Driven by Electrochemical and Photochemical Stimuli;" Angew. Chem, in, Ed.; 2003; pp. 4097-4100; vol. 42; Wiley-VCH Verlag GmbH & Co.
Ko et al.; "Supramolecular assemblies built with host-stabilized charge-transfer interactions;" Chem. Commun.; 2007; pp. 1305-1315; The Royal Society of Chemistry.
Moon et al.; "Cucurbit[8]uril-Mediated Redox-Controlled Self-Assembly of Viologen-Containing Dendrimers;" Angew. Chem. Int. Ed.; 2004; pp. 5496-5499; vol. 43; Wiley-VCH Verlag GmbH & Co.
Wang et al.; "Electrochemical Switching and Size Selection in Cucurbit[8]uril-Mediated Dendrimer Self-Assembly;" Angew. Chem. Int. Ed.; 2006; pp. 7042-7046; vol. 45; Wiley-VCH Verlag GmbH & Co.
Floudas et al.; "Poly(ethylene oxide-b-isoprene) Diblock Copolymer Phase Diagram;" Macromolecules; 2001; pp. 2947-2957; vol. 34; American Chemical Society.
Sun et al.; "The photoinduced long-lived charge-separated state of Ru(bpy).sub.3-methylviologen with cucurbit[8]uril in aqueous solution;" Chem. Commun; 2006; pp. 4195-4197; The Royal Society of Chemistry.
Jon et al.; "A facile, stereoselective [2+2] photoreaction mediated by cucurbit[8]uril;" Chem. Commun.; 2001; pp. 1938-1939; The Royal Society of Chemistry.
Rauwald et al.; "Supramolecular Block Copolymers with Cucurbit[8]uril in Water;" Angew. Chem. Int. Ed.; 2008; pp. 3950-3953; vol. 47; Wiley-VCH Verlag GmbH & Co.
Broeren et al.; "Multivalency in the Gas Phase: The Study of Dendritic Aggregates by Mass Spectrometry;" Angew. Chem. Int. Ed.; 2004; pp, 3557-3562; vol. 43; Wiley-VCH Verlag GmbH & Co.
Osaka et al.; "Characterization of host-guest complexes of cucurbit[n]uril (n=6,7) by electrospray ionization mass spectrometry;" J. Mass Spectrom; 2006; pp. 202-207; vol. 41; John Wiley & Sons, Ltd.
Brunsveld et al.; "Supramolecular Polymers;" Chem. Rev.; 2001; pp. 4071-4097; vol. 101; American Chemical Society.
Knapp et al.; "A Novel Synthetic Strategy toward Soluble, Well-Defined Ruthenium(II) Coordination Polymers," Macromolecules; 1996; pp. 478-480; vol. 29; American Chemical Society.
Kim et al.; "Direct Synthesis of Polymer Nanocapsules with a Noncovalently Tailorable Surface.," Angew. Chem. Int. Ed.; 2007; vol. 46, pp. 3471-3474; Wiley-VCH Verlag GmbH & Co.
Ligthart et al.; "Supramolecular Polymer Engineering;" Macromolecular Engineering, Precise Synthesis, Materials Properties, Applications; 2007; pp. 351-399; Wiley-VCH Verlag GmbH & Co.
Nov. 3, 2009 International Search Report issued in International Application No. PCT/GB2008/004016.
Nov. 3, 2009 Written Opinion of the International Search Report issued in International Application No. PCT/GB2008/004016.
Hwang et al, "Noncovalent Immobilization of Proteins on a Solid Surface by Cucurbit[7]uril-Ferrocenemethylammonium Pair, a Potential Replacement of Biotin-Avidin Pair". J. Am. Chem Soc. vol. 129, pp. 4170-4171, 2007.

(56) References Cited

OTHER PUBLICATIONS

Appel et al. "Ultrahigh-Water-Content Supramolecular Hydrogels Exhibiting Multistimuli Responsiveness". J. Am. Chem. Soc. vol. 134, pp. 11767-11773, 2012.
Appel et al. "Supramolecular polymeric hydrogels". Chem. Soc. Rev. vol. 41, pp. 6195-6214, 2012.
Benguigui et al. "Homogeneous and inhomogeneous polyacrylamide gels as observed by small angle neutron scattering: A connection with elastic properties". Eur. Phys. J. B. vol. 11, pp. 439-444, 1999.
Biedermann et al. "Postpolymerization Modification of Hydroxyl-Functionalized Polymers with Isocyanates". Macromolecules. vol. 44, pp. 4828-4835, 2011.
Esposito et al. "Comparative analysis of tetracycline-containing dental gels: poloxamer- and monoglyceride-based formulations". International Journal of Pharmaceutics. vol. 142, pp. 9-23, 1996.
Estroff et al. "Water Gelation by Small Organic Molecules". Chem. Rev. vol. 104, No. 3, pp. 1201-1217, 2004.
Greenfield et al. "Tunable Mechanics of Peptide Nanofiber Gels". Langmuir. vol. 26, No. 5, pp. 3641-3647, 2010.
Hartgerink et al. "Self-Assembly and Mineralization of Peptide-Amphiphile Nanofibers". Science. vol. 294, pp. 1684-1688, Nov. 23, 2001.
Heitmann et al. "Sequence-Specific Recognition and Cooperative Dimerization of N-Terminal Aromatic Peptides in Aqueous Solution by a Synthetic Host". J. Am. Chem. Soc. vol. 128, pp. 12574-12581, 2006.
Horkay et al. "Macroscopic and Microscopic Thermodynamic Observations in Swollen Poly(vinyl acetate) Networks". Macromolecules. vol. 24, pp. 2896-2902, 1991.
Horkay et al. "Structural investigations of a neutralized polyelectrolyte gel and an associating neutral hydrogel". Polymer. vol. 46, pp. 4242-4247, 2005.
Hunt et al. "Tunable, High Modulus Hydrogels Driven by Ionic Coacervation". Adv. Mater. vol. 23, pp. 2327-2331, 2011.
Katakam et al. "Controlled release of human growth hormone following subcutaneous administration in dogs". Int. J. Pharm. vol. 152, pp. 53-58, 1997.
Koopmans et al. "Formation of Physical Hydrogels via Host-Guest Interactions of β-Cyclodextrin Polymers and Copolymers Bearing Adamantyl Groups". Macromolecules. vol. 41, pp. 7418-7422, 2008.
Kretschmann et al. "Switchable Hydrogels Obtained by Supramolecular Cross-Linking of Adamantyl-Containing Lcst Copolymers with Cyclodextrin Dimers". Angew. Chem. Int. Edit. vol. 45, pp. 4361-4365, 2006.
Richard et al. "Analysis and Visualisation of Neutron-Scattering Data". J. Neutron Research. vol. 4, pp. 33-39, 1996.
Lee et al. "Unprecedented host-induced intramolecular charge-transfer complex formation". Chem. Comm. pp. 2692-2693, 2002. The Royal Soc. of Chem.
Li et al. "Poly(ester urethane)s Consisting of Poly[(R)-3-hydroxybutyrate] and Poly(ethylene glycol) as Candidate Biomaterials: Characterization and Mechanical Property Study". Biomacromolecules. vol. 6, pp. 2740-2747, 2005.
Loh et al. "Micellization and Thermogelation of Poly(ether urethane)s Comprising Poly(ethylene glycol) and Poly (propylene glycol)". Macromol. Symp. vol. 296, pp. 161-169, 2010.
Loh et al. "Biodegradable Thermogelling Poly[(R)-3-hydroxybutyrate]-Based Block Copolymers: Micellization, Gelation, and Cytotoxicity and Cell Culture Studies". J. Phys. Chem. B. vol. 113, pp. 11822-11830, 2009.
Loh et al. "Hydrolytic degradation and protein release studies of thermogelling polyurethane copolymers consisting of poly[(R)]-3-hydroxybutyrate], poly(ethylene glycol), and poly(propylene glycol)". Biomaterials. vol. 28, pp. 4113-4123, 2007.
Loh et al. "Biodegradable thermogelling poly(ester urethane)s consisting of poly(lactic acid)—Thermodynamics of micellization and hydrolytic degradation". Biomaterials. vol. 29, pp. 2164-2172, 2008.
Loh et al. "Synthesis and water-swelling of thermo-responsive poly(ester urethane)s containing poly(ε -caprolactone), poly(ethylene glycol) and poly(propylene glycol)". Biomaterials. vol. 29, pp. 3185-3194, 2008.
Loh et al. "Controlled drug release from biodegradable thermoresponsive physical hydrogel nanofibers". J. Contol. Release. vol. 143, pp. 175-182, 2010.
Loh et al. "Encapsulation of basic fibroblast growth factor in thermogelling copolymers preserves its bioactivity." J. Mater. Chem. vol. 21, pp. 2246-2254, 2011.
Lutolf, Matthias. "Spotlight on hydrogels". Nature Materials. vol. 8, pp. 451-453, Jun. 2009.
Mynar et al. "The gift of healing". Nature. vol. 451, pp. 895-896, Feb. 2008.
Nakamura et al. "Supramolecular Catalysis of the Enantiodifferentiating [4+4] Photocyclodimerization of 2-Anthracenecarboxylate by γ-Cyclodextrin". J. Am. Chem. Soc. vol. 125, pp. 966-972, 2003.
Nochi et al. "Nanogel antigenic protein-delivery system for adjuvant-free intranasal vaccines". Nat. Mat. vol. 9, pp. 572-578, Jun. 20, 2010.
Peppas et al. "Physicochemical Foundations and Structural Design of Hydrogels in Medicine and Biology". Annu. Rev. Biomed. Eng. vol. 2, pp. 9-29, 2000.
Pezron et al. "Conformation of gelatin chains in aqueous solutions: 1. A light and small-angle neutron scattering study". Polymer. vol. 32 No. 17, pp. 3201-3210, 1991.
Reczek et al. "Multivalent Recognition of Peptides by Modular Self-Assembled Receptors". J. Am. Chem. Soc. vol. 131, pp. 2408-2415, 2009.
Ritger et al. "A Simple Equation for Description of Solute Release I. Fickian and Non-Fickian Release from Non-Swellable Devices in the form of Slabs, Spheres, Cylinders or Discs". Journal of Contorlled Release. vol. 5, pp. 23-36, 1987.
Ritger et al. "A Simple Equation for Description of Solute Release II. Fickian and Anomalous Release from Swellable Devices". Journal of Controlled Release. vol. 5, pp. 37-42, 1987.
Staats et al. "Chaperoning vaccines". Nat. Mat. vol. 9, pp. 537-538, Jul. 2010.
Tamaki et al. "Reversible Photodimerization of Water-Soluble Anthracenes included in γ-Cyclodextrin." Chem. Lett. pp. 53-56, 1984.
Uzunova et al. "Toxicity of cucurbit[7]uril and cucurbit[8]uril: an explanatory in vitro and in vivo study". Org. Biomol. Chem. vol. 8 No. 9, pp. 2037-2042, May 7, 2010.
Van Tomme et al. "Self-gelling hydrogels based on oppositely charged dextran microspheres". Biomaterials. vol. 26, pp. 2129-2135, 2005.
Wang et al. "High-water-content mouldable hydrogels by mixing clay and a dendritic molecular binder". Nature. vol. 463, pp. 339-343, Jan. 21, 2010.
Wojtecki et al. "Using the dynamic bond to access macroscopically responsive structurally dynamic polymers". Nat. Mat. vol. 10, pp. 14-27, 2011.
Wu et al. "Fabrication of Supramolecular Hydrogels for Drug Delivery and Stem Cell Encapsulation". Langmuir. vol. 24, pp. 10306-10312, 2008.
Yang et al. "Highly Stereoselective Photocyclodimerization of a-Cyclodextrin-Appended Anthracene Mediated by γ-Cyclodextrin and Cucurbit[8]uril: A Dramatic Steric Effect Operating Outside the Binfing Site". J. Am. Chem. Soc. vol. 130, pp. 8574-8575, 2008.
Jun. 20, 2013 International Search Report and Written Opinion issued in International Application No. PCT/GB2013/050414.
May 14, 2012 Search Report issued in Great Britain Application No. GB1202834.6.
Huang et al. "Fabrication of cucurbit[6]uril mediated alginate physical hydrogel beads and their application as a drug carriers". e-Polymers. vol. 95, pp. 1-11, 2008.

(56) References Cited

OTHER PUBLICATIONS

Park et al. "In Situ Supramolecular Assembly and Modular Modification of Hyaluronic Acid Hydrogels for 3D Cellular Engineering". ACS Nano. vol. 6, No. 4, pp. 2960-2968, 2012.

Loh et al. "New Biodegradable Thermogelling Copolymers Having Very Low Gelation Concentrations". Biomacromolecules. vol. 8, pp. 585-593, 2007.

Kim et al. "New Cucurbituril Homologues: Syntheses, Isolation, Characterization, and X-ray Crystal Structures of Cucurbit[n]uril (n=5, 7, and 8)". J. Am. Chem. Soc. vol. 122, pp. 540-541, 2000.

U.S. Appl. No. 14/379,109 in the name of Scherman et al., filed Aug. 15, 2014.

Jan. 3, 2012 Ofice Action issued in U.S. Appl. No. 12/734,925.

Jul. 2, 2012 Office Action issued in U.S. Appl. No. 12/734,925.

Sep. 25, 2015 Office Action issued in Chinese Patent Application No. 201380020985.8.

* cited by examiner

Figure 3 a-b
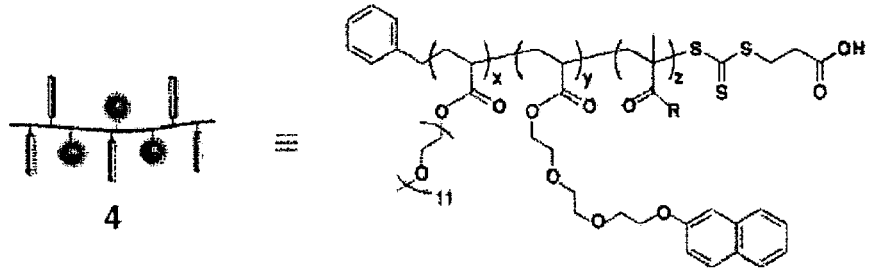
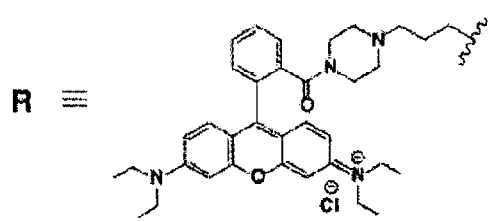
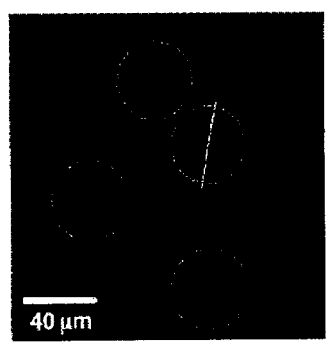
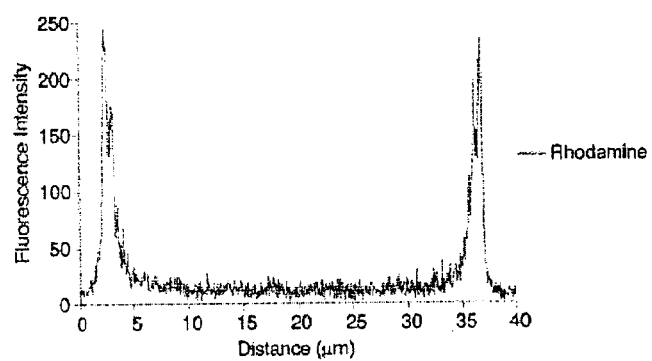

Figure 3 c-d
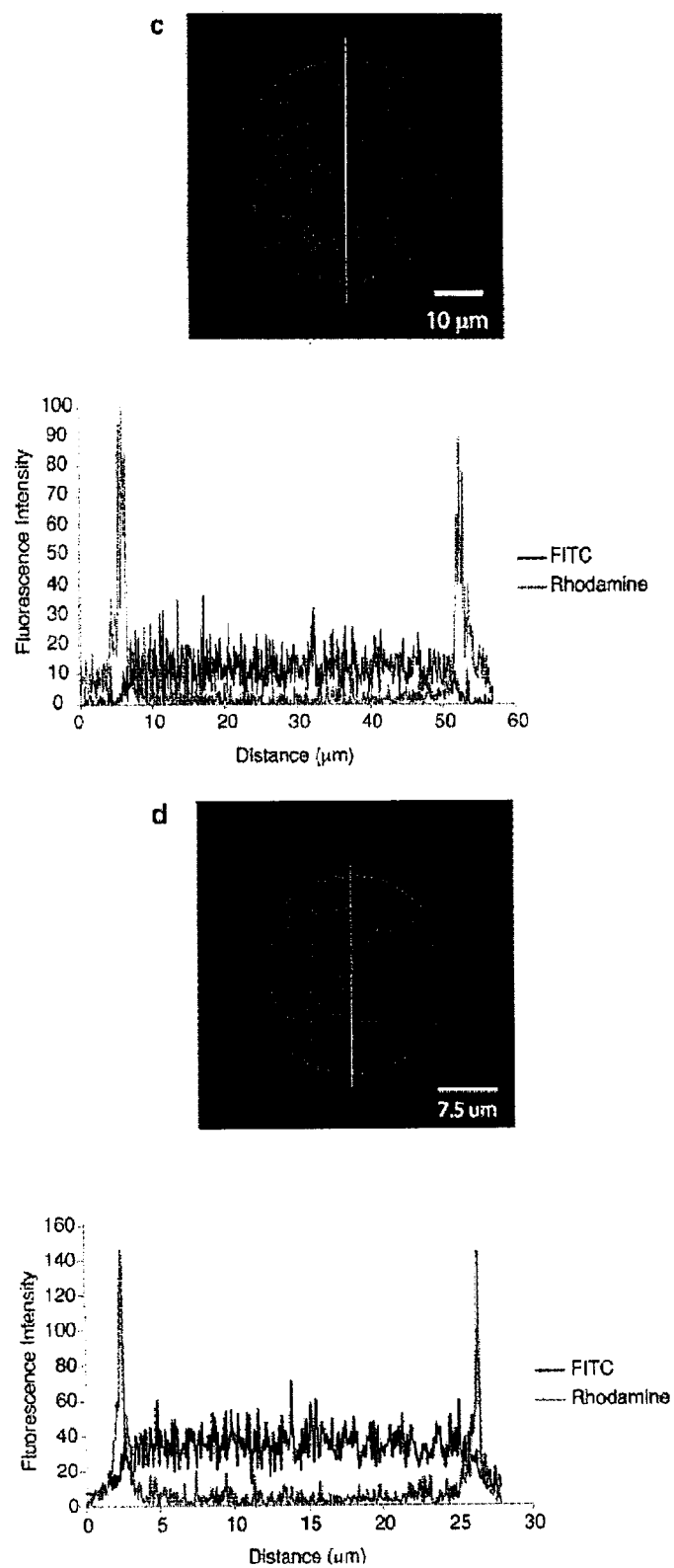

Figure 6 b-d
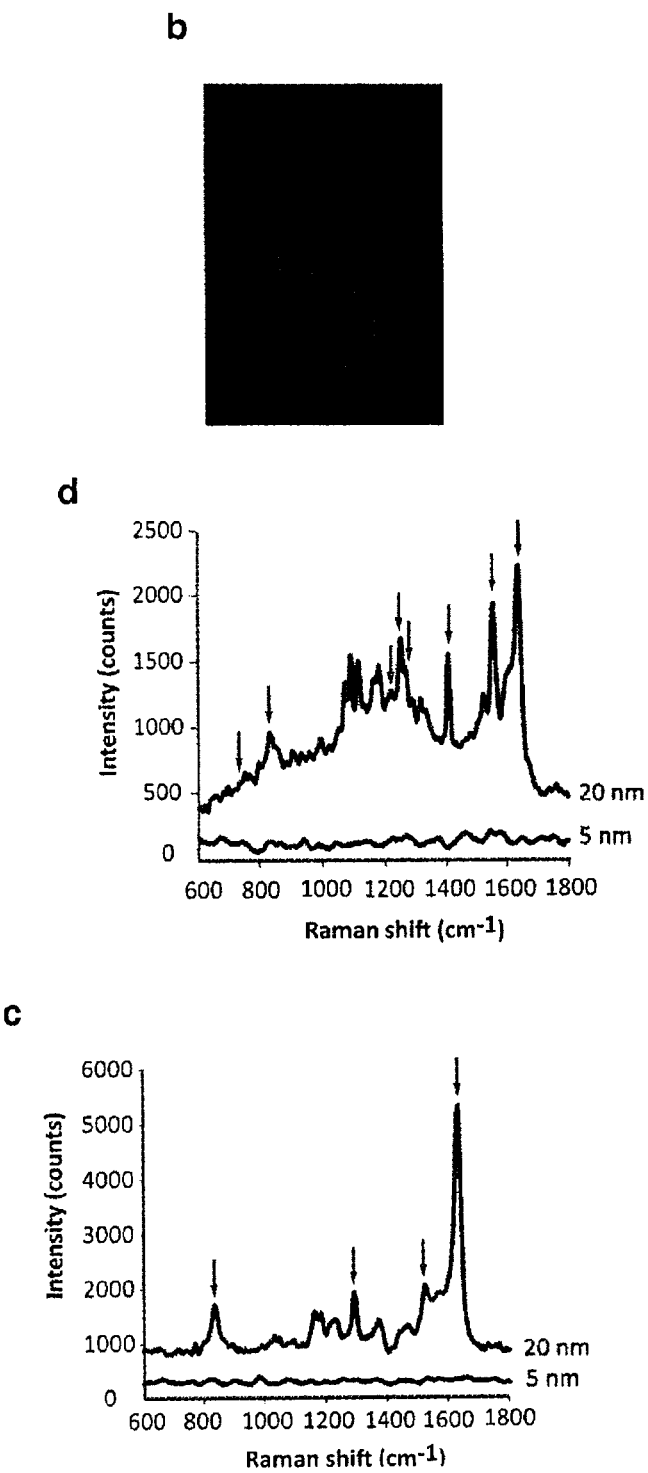

Figure 10
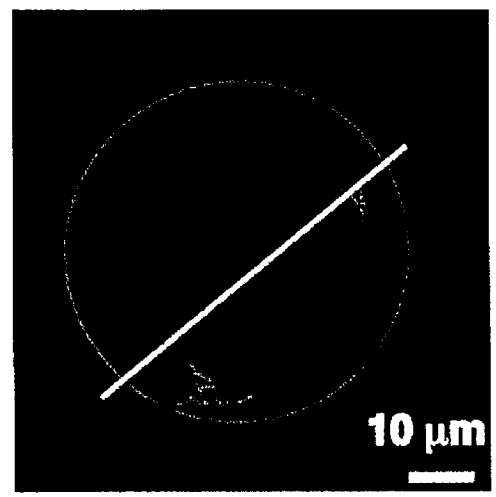
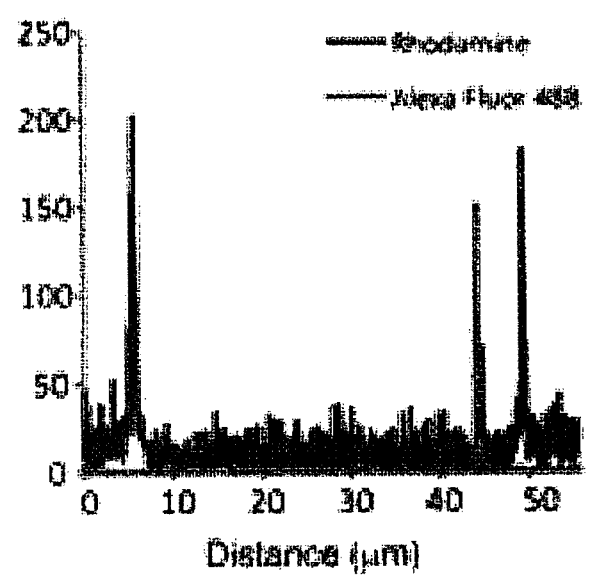

SUPRAMOLECULAR CAPSULES

PRIORITY

This application claims priority to GB 1112893.1 filed on 26 Jul. 2011 and GB 1202127.5 filed on 8 Feb. 2012, the contents of both of which are hereby incorporated by reference in their entirety.

FIELD OF THE INVENTION

This invention relates to capsules, particularly microcapsules, based on a cucurbituril cross-linked network, and methods for the preparation of such capsules, and their use in methods of delivering encapsulated components.

BACKGROUND

The microencapsulation of a component by self-assembled hollow microspheres is one of the important aspects of nanotechnology and materials science. Control over the shape and composition of the supporting structure, parameters that influence the material properties, is important for many applications, such as diagnostics, drug delivery, electronic displays and catalysis (see Ke at al. *Angew. Chem.* 2011, 123, 3073; De Cock et al. *Angew. Chem. Int. Ed.* 2010, 49, 6954; Yang et al. *Angew. Chem.* 2011, 123, 497; Comiskey et al. *Nature* 1998, 394, 253; Peyratout at al. *Angew. Chem. Int. Ed.* 2004, 43, 3762). Preparation of conventional polymeric microcapsules proceeds via a layer-by-layer (L-b-L) scheme, where a solid support is coated by the sequential addition of a series of oppositely charged polyelectrolyte layers (see Caruso et al. *Science* 1998, 282, 1111; Donath et al, *Angew. Chem. Mt. Ed.* 1998, 37, 2201). This strategy provides a uniform material but suffers from reduced encapsulation efficiencies due to the solid template. An alternative method utilises colloidal emulsion-templating where liquid-liquid interfaces drive the self-assembly of shell components (see Cui at al. *Adv. Funct. Mater.* 2010, 20, 1625). However, it is difficult to control monodispersity and material diversity of the resulting microcapsules, thereby limiting its functionality in drug delivery and sensing applications.

In contrast, microfluidic droplets, a subset of colloidal emulsion, have shown great promise for microcapsule fabrication (see Gunther et al. *Lab Chip* 2006, 6, 1487; Huebner et al. *Lab Chip* 2008, 8, 1244; Theberge et al. *Angew. Chem. Int. Ed.* 2010, 49, 5846). These droplets of narrow size distribution (polydispersity index<2%) can be generated at extremely high frequency with economic use of reagents (see Xu et al. *AlChE Journal* 2006, 52, 3005). Initial efforts to prepare capsules based on microdroplet-assisted fabrication have focused on phase separation using double emulsion and liquid crystal core templating (see Utada et al. *Science* 2005, 308, 537; Priest at al. *Lab Chip* 2008, 8, 2182). The formation of polymeric capsule walls has also been described in an approach that involves microfluidic device surface treatment and rapid polymerization techniques (see Zhou at al. *Electrophoresis* 2009, 31, 2; Abraham et al. *Advanced Materials* 2008, 20, 2177). The wall is formed as the solvent evaporates from formed organic solvent droplets. Metal-organic framework capsules have also been recently reported (see Ameloot et al. *Nat. Chem.* 2011, 3, 382). With the current ionic or covalent cross-linking strategies, however, the main challenge in capsule fabrication lies in the simultaneous production of uniform capsules with high cargo loading efficiencies and facile incorporation of diverse functionality into the capsule shell.

The present inventors have now established a capsule based on a cucurbituril-based host-guest network. Designing microstructures using multivalency and cooperativity through molecular recognition provides an unparalleled opportunity in the fabrication of microcapsules with tailorable interactions and functionalities. However, efforts in preparing microcapsules using supramolecular host-guest approach, as described herein, are scarce (see De Cock at al. *Angew. Chem. Int. Ed.* 2010, 49, 6954).

Previous disclosures include a colloidal microcapsule comprising β-cyclodextrin and modified gold nanoparticles (AuNPs) prepared via emulsion templating (Patra at al., *Langmuir* 2009, 25, 13852), and a microcapsule comprising polymers functionalized with cyclodextrin and ferrocene prepared using a L-b-L synthesis (Wang et al., *Chemistry of Materials* 2008, 20, 4194).

SUMMARY OF THE INVENTION

The present invention generally provides capsules having a shell of material that is a supramolecular cross-linked network. The network is formed from a host-guest complexation of cucurbituril (the host) and one or more building blocks comprising suitable guest functionality. The complex non-covalently crosslinks the building block and/or non-covalently links the building block to another building block thereby forming the network.

In a general aspect the present invention provides a capsule having a shell obtainable from the complexation of cucurbiturils with suitable guest molecules.

In a first aspect of the invention there is provided a capsule having a shell which is obtainable from the complexation of a composition comprising cucurbituril and one or more building blocks having suitable cucurbituril guest functionality thereby to form a supramolecular cross-linked network.

In one embodiment, the shell is obtainable from the complexation of (a) a composition comprising cucurbituril and (1) or (2); or (b) a composition comprising a plurality of covalently linked cucurbiturils and (1), (2) or (3).

In one embodiment, the shell is obtainable from the complexation of a composition comprising cucurbituril and (1) or (2).

In one embodiment, the shed is obtainable from the complexation of a composition comprising cucurbituril and (1).

(1) comprises a first building block covalently linked to a plurality of first cucurbituril guest molecules and a second building block covalently linked to a plurality of second cucurbituril guest molecules, wherein a first guest molecule and a second guest molecule together with cucurbituril are suitable for forming a ternary guest-host complex.

(2) comprises a first building block covalently linked to a plurality of first cucurbituril guest molecules and a plurality of second cucurbituril guest molecules, wherein a first and a second guest molecule together with cucurbituril are suitable for forming a ternary guest-host complex. Optionally the composition further comprises a second building block covalently linked to one or more third cucurbituril guest molecules, one or more fourth cucurbituril guest molecules or both, wherein a third and a fourth molecule together with cucurbituril are suitable for forming a ternary guest-host complex, and/or the first and fourth molecules together with cucurbituril are suitable for forming a ternary guest-host complex, and/or the second and third molecules together with cucurbituril are suitable for forming a ternary guest-host complex;"

(3) comprises a first building block covalently linked to a plurality of first cucurbituril guest molecules, wherein the first guest molecule together with the cucurbituril are suitable for forming a binary guest-host complex. Optionally the composition further comprises a second building block covalently linked to one or more second cucurbituril guest molecules, wherein the second guest molecule together with the cucurbituril are suitable for forming a binary guest-host complex.

In one embodiment, the cucurbituril is selected from CB[8] and variants and derivates thereof.

In one embodiment, the cucurbituril forms a ternary complex with suitable guest molecules, for example with first and second guest molecules.

In one embodiment, the capsule is a microcapsule.

In one embodiment, the capsule encapsulates a component.

In a second aspect of the invention there is provided a method for the preparation of a capsule having a shell, such as the capsule of the first aspect of the invention, the method comprising the step of:

(i) contacting a flow of a first phase and a flow of a second phase in a channel, thereby to generate in the channel a dispersion of discrete regions, preferably droplets, of the second phase in the first phase, wherein the second phase comprises cucurbituril and one or more building blocks having suitable cucurbituril guest functionality suitable to form a supramolecular cross-linked network, thereby to form a capsule shell within the discrete region, wherein the first and second phases are immiscible.

In one embodiment, the second phase comprises either (a) a cucurbituril and (1) or (2); or (b) a plurality of covalently linked cucurbiturils and (1), (2) or (3).

In one embodiment, one of the first and second phases is an aqueous phase and the other phase is a water immiscible phase.

In one embodiment, the second phase is an aqueous phase. The first phase is a water immiscible phase, for example an oil phase.

In one embodiment, the first phase is an aqueous phase. The second phase is a water immiscible phase, for example an oil phase.

In one embodiment, the method further comprises the step of (ii) collecting the outflow from the channel, thereby to obtain a droplet, which contains a capsule.

In one embodiment, the method comprises the step (ii) above and (iii) optionally drying the capsule obtained in step (ii).

In one embodiment, the channel is a microfluidic channel.

In one embodiment, the flow of the second phase is brought into contact with the flow of the first phase substantially perpendicular to the first phase. In this embodiment, the channel structure may be a T-junction geometry.

In one embodiment, the flow of the second phase further comprises a component for encapsulation, and the step (i) provides a capsule having a shell encapsulating the component.

In a third aspect of the invention there is provided a capsule obtained or obtainable by the method of the second aspect of the invention.

In a fourth aspect of the invention there is provided a method of delivering a component to a location, the method comprising the steps of:

(i) providing a capsule having a shell encapsulating a component;
(ii) delivering the capsule to a target location;
(iii) releasing the component from the shell.

In an alternative aspect of the invention there is provided a capsule having a shell which is obtainable from the complexation of a composition comprising a host and one or more building blocks having suitable host guest functionality thereby to form a supramolecular cross-linked network.

In one embodiment the host is selected from cyclodextrin, calix[n]arene, crown ether and cucurbituril, and the one or more building blocks having suitable host guest functionality for the cyclodextrin, calix[n]arene, crown ether or cucurbituril host. In one embodiment, references in the first to fourth aspects above to cucurbituril and a cucurbituril guest may be interpreted as a reference to an alternative host and a suitable guest for that host.

SUMMARY OF THE FIGURES

FIG. 3 (a) Chemical structure and schematic representation of NP-RD-pol 4. (b) LSCM image of droplets containing aqueous solutions of Np-RD-pol, CB[8] and MV-AuNP, and the fluorescence intensity profile. Scale bar=40 µm. (c) LSCM image of a droplet (46 µm diameter) containing aqueous solutions of Np-RD-pol, CB[8], MV-AuNP and FITC-dextran and the corresponding fluorescence intensity profile. Scale bar=7.5 µm. (d) LSCM image of a droplet (23 µm diameter) containing aqueous solutions of Np-Rd-pol, CB[8], MV-AuNP and FITC-dextran and the corresponding fluorescence intensity profile. Scale bar=10 µm.

$MV^{2+}$-AuNP:Np-pol, and the resulting formation of 2:1 $(MV^{+*}$-AuNP$)_2 \subset CB[8]$ complex. (b) The fluorescence images of the process of the disintegration of the microcapsule wall material in an aqueous solution of $Na_2S_2O_4$ and in $H_2O$ over 12 h in $N_2$ environment at 25° C. Scale bars=5 µm.

FIG. 6 (a) Schematic representations of the microcapsules with and without $MV^{2+}$-AuNPs (5 nm and 20 nm). For negative control, $MV^{2+}$-pol 5 was used instead of AuNPs. (b) SERS spectra of empty microcapsules consisting of $MV^{2+}$-pol, 5 nm $MV^{2+}$-AuNP, and 20 nm $MV^{2+}$-AuNP, showing characteristic peaks for CB[8] and $MV^{2+}$ (indicated with arrows). (c) SERS spectra of FITC-dextran encapsulated microcapsules consisting of $MV^{2+}$-pol and 20 nm $MV^{2+}$-AuNP, showing characteristic peaks for FITC (indicated with arrows) in addition to capsule shell materials. All spectra were obtained using 633 nm excitation laser line. (d) SERS mapping of the microcapsule, showing localization of the SERS signal for CB[8] and $MV^{24}$.

Figure 7:
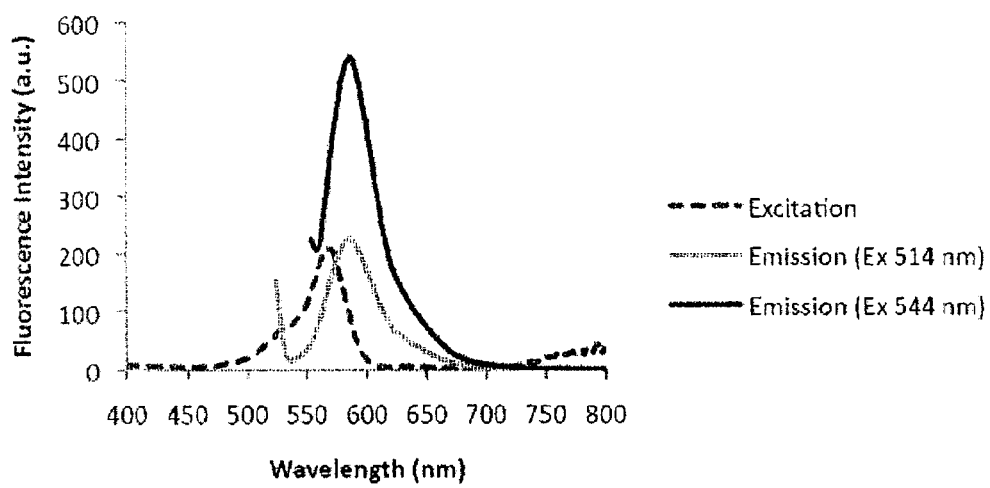

FIG. 7 is the excitation spectrum of Np-RD-pol and emission spectra excited at 514 nm and 544 nm.

Figure 8:
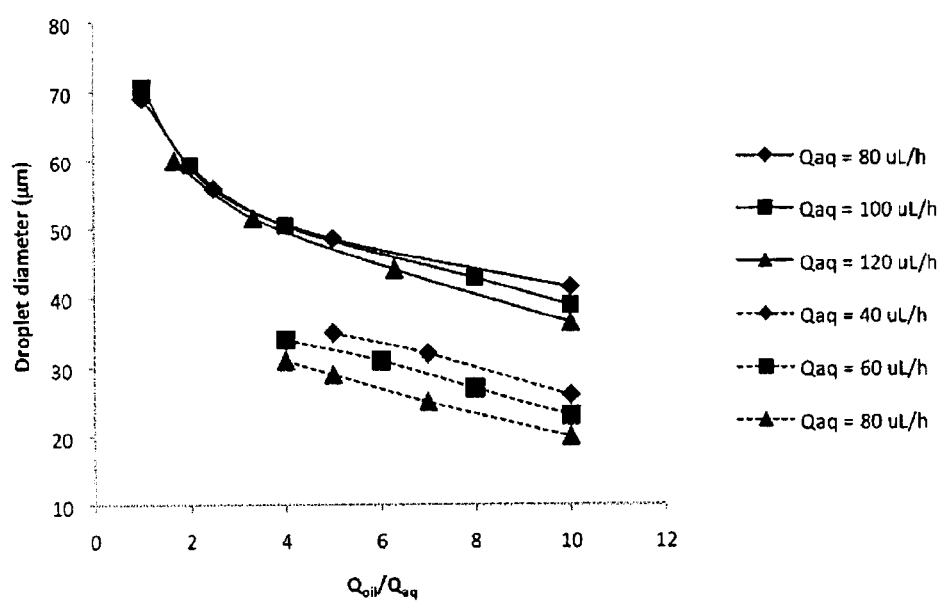

FIG. 8 shows the variation in mean diameter of droplets as a function of the ratio of $Q_{oil}/Q_{aq}$, of various aqueous streams of $Q_{aq}$=80 µL/h, 100 µL/h, 120 µL/h using T-junction and a channel 40 µm in width (solid line), and of various aqueous streams of $Q_{aq}$=40 µL/h, 60 µL/h, 80 µL/h using T-junction and a channel 20 µm in width (dashed line).

Figure 9:
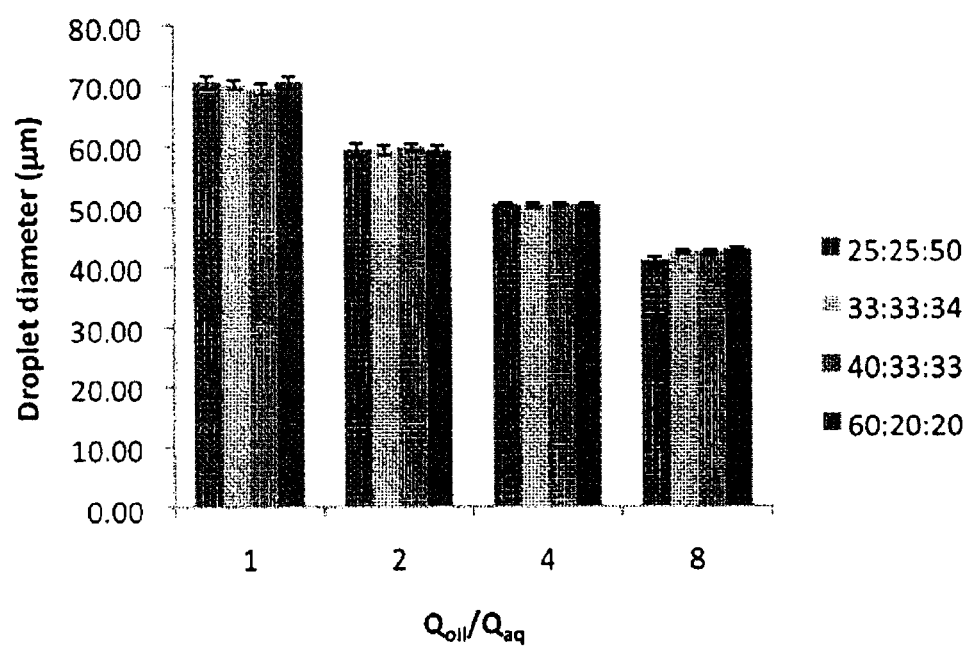

FIG. 9 shows the variation in the mean diameter of droplets as a function of the ratio of the oil and the aqueous stream, and as a function of the ratio of the individual aqueous stream flow rates.

FIG. 10 is the LSCM image of a droplet containing aqueous solutions of Np-RD-pol, CB[8], MV-AuNP and GFP-expressing *E. coli* cells and the corresponding fluorescence intensity profile.

Figure 11:
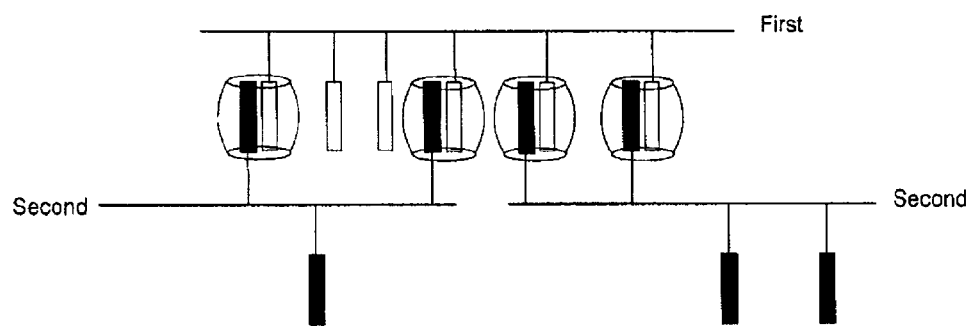

FIG. 11 is a schematic representation of some of the first guest molecules (unshaded rectangles) of the first building block are in complex with cucurbituril hosts (barrels) and second guest molecules (shaded rectangles) of the second building blocks.

Figure 12:
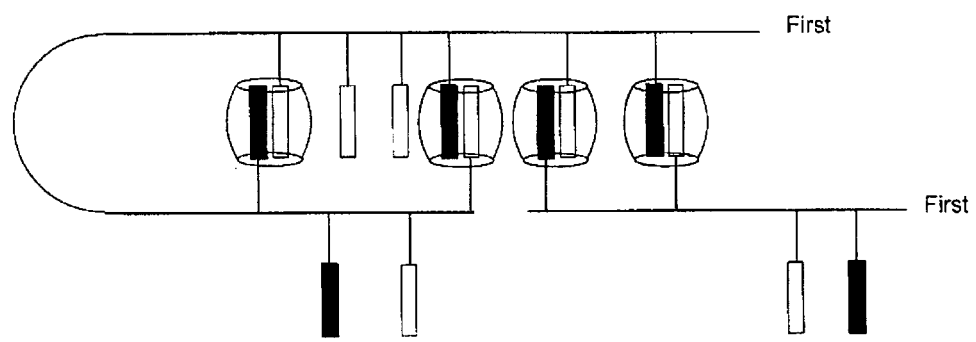

FIG. 12 is a schematic representation of a basic network formed between cucurbituril and two single first building blocks each having a plurality of first and second guest molecules.

Figure 13:
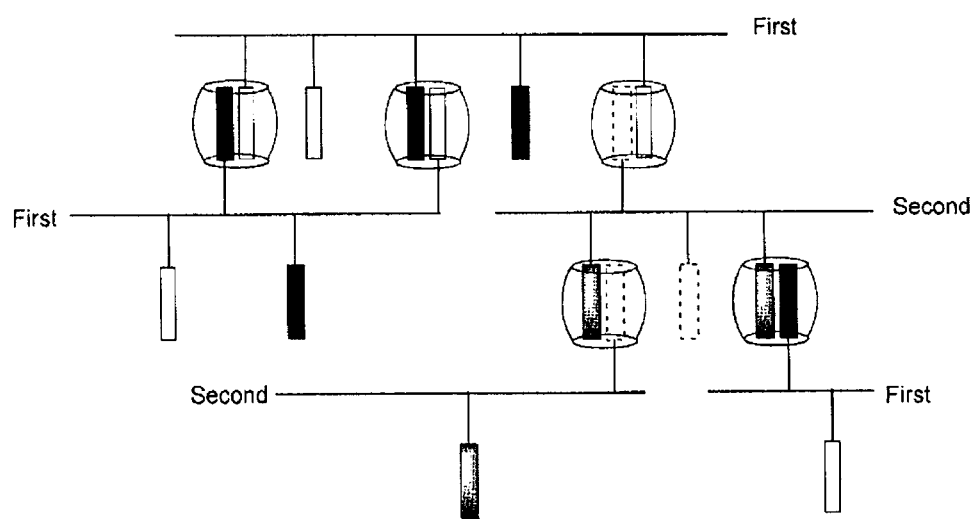

FIG. 13 is a schematic representation of a basic network formed between cucurbituril, three single first building blocks each having a plurality of first and second guest molecules, and two second building blocks each having a plurality of third and fourth guest molecules.

Figure 14:
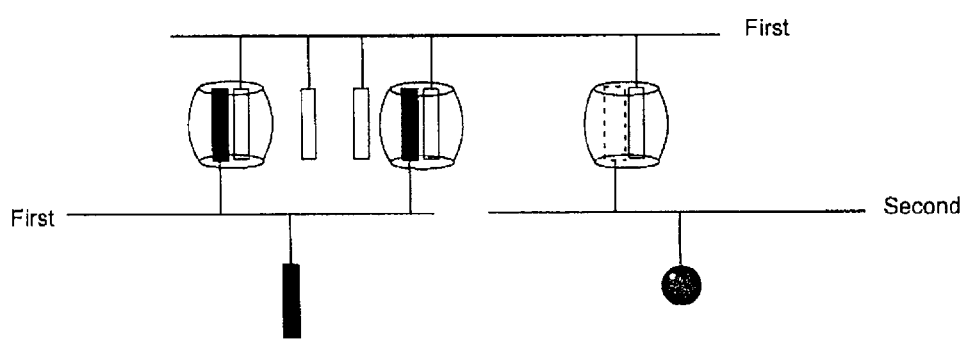

FIG. 14 is a schematic representation of a basic network formed between cucurbituril, two single first building blocks each having a plurality of first and second guest molecules, and also including a single second building block, which is covalently linked to one fourth guest molecule, and a detectable label.

Figure 15:
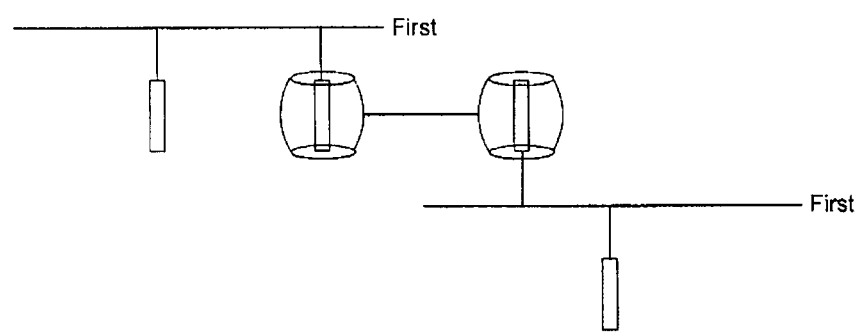

FIG. 15 is a schematic representation of a basic network formed between a plurality of covalently linked cucurbiturils and two single first building blocks each haying a plurality of first guest molecules.

Figure 16:
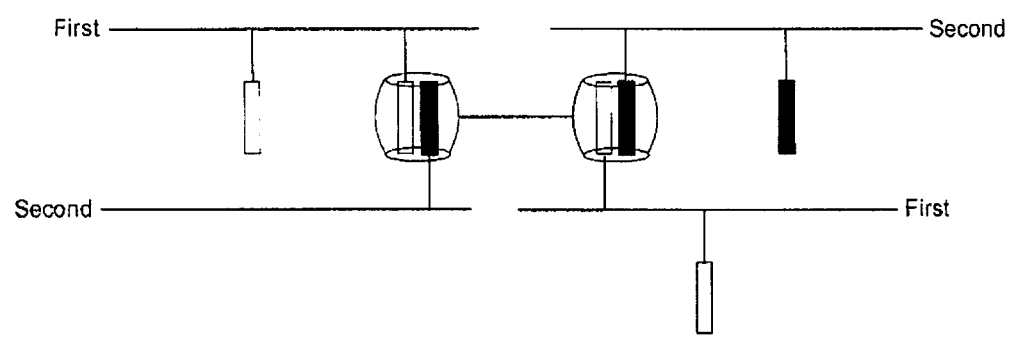

FIG. 16 is a schematic representation of a basic network formed between a plurality of covalently linked cucurbiturils, two single first building blocks each having a plurality of first guest molecules, and two single second building blocks each having a plurality of second guest molecules.

DETAILED DESCRIPTION OF THE INVENTION

The present inventors have established that capsules may be prepared having a shell that is obtainable from the supramolecular complexation of cucurbituril with building blocks covalently linked to appropriate cucurbituril guest molecules.

The capsules are formed using fluidic droplet generation techniques, amongst others. The ability of cucurbituril and the building blocks to form a shell is surprising given the previously reported behaviour of such materials.

Earlier work from one of the present inventors has found that cucurbituril may be used to form a supramolecular cross-linked network via host-guest complexation (see Appel et al. *J. Am. Chem. Soc.* 2010, 132, 14251). The network is based on the supramolecular assembly of a ternary complex of CB[8] together with a methyl viologen-functionalised (MV) polymer and a napthol-functionalised (Np) polymer. However, the networks described here are in the form of supramolecular hydrogels. Capsules are not described or suggested.

The hydrogels are prepared by sonication of the MV-functionalised polymer together with CB[8], followed by addition of the Np-functionalised polymer, with a subsequent short mixing step.

The finding by the present inventors that cucurbituril can be mixed together with building blocks connected to appropriate guest molecules thereby to yield a shell of material was therefore unexpected. The capsule is obtainable through the use of fluidic droplet preparation techniques and bulk droplet generation techniques. The former is particularly beneficial in that it generates droplets having a very low distribution of sizes, which results in capsules having a very low distribution in sizes. Moreover, the methods of the invention allow close control over the formation of the product capsule. Simple changes in the fluidic droplet preparation technique, such as changes in flow rates, may be used to control the size of the capsule obtained, the size of the pores in the shell, and the thickness of the shell, amongst others.

The capsules of the invention are shown to be robust, and are capable of withstanding temperatures of at least 100° C. The capsules also maintain their integrity at reduced pressure.

The capsules of the invention are suitable for encapsulating a component. Using the fluidic droplet preparation techniques described herein, a capsule shell may be constructed in the presence of the component to be encapsulated. Thus, in one procedure the shell may be formed and the component encapsulated. Advantageously therefore, the capsule may be constructed without the need for a later passive diffusion step after the capsule construction. Furthermore, the method of encapsulation allows high rates of incorporation of the material into the capsule, and material waste is therefore minimised.

The invention is now described in more detail with reference to the each feature of the invention.

Capsules

A capsule of the invention comprises a shell of material. The material is the supramolecular complex that is formed from the complexation of cucurbituril with building blocks covalently linked to appropriate cucurbituril guest molecule. The shell defines an internal space, which may be referred to as a hollow space, which is suitable for holding a component. Thus, in one embodiment, the capsules of the invention extend to those capsules encapsulating a component within the shell. The shell may form a barrier limiting or preventing the release of material encapsulated within.

The component may be releasable from the capsule, through pores that are present in the shell. In some embodiments, the pores are sufficiently small to prevent the component from being released. Thus, the network making up the shell may be at least partly disassembled thereby permitting release of material from within the shell. Further pores may be generated by the application of an external stimulus to the shell. In this case, the pores may be generated through a disruption of the cucurbituril guest complex. Such decomplexation therefore creates pores through which encapsulated components may be released from within the shell. In some embodiments of the invention, the shell material may subsequently be reformed by reassembly of the shell components.

In one embodiment, the capsule holds water within the shell. The water may be an aqueous solution comprising one or more of the reagents that are for use in the preparation of the supramolecular shell i.e. unreacted reagents. In one embodiment, the aqueous solution comprises cucurbituril and/or (1) or (2) or (b) a plurality of covalently linked cucurbiturils and/or (1), (2) or (3). Within the shell there may also be present a network that is formed from the complexation of the reagents that have been used to generate the shell.

Within the shell there may be provided an encapsulated material, which may be provided in addition to water and the reagents that are for use in the supramolecular assembly of the shell.

Where the capsule is said to encapsulate a component, it is understood that that this encapsulated component may be present within the internal space defined by the shell.

In one embodiment, the encapsulant is also present, at least partially, within the pores of the shell.

The presence of a component within the shell and/or within the pores of the shell may be determined using suitable analytical techniques which are capable of distinguishing the shell material and the encapsulant. For example, each of the shell material and the component may have a detectable label or suitable functionality that is independently detectable (orthogonal) to the label or functionality of the other. In one embodiment, each of the shell and the component has an orthogonal fluorescent label. For example, one has a rhodamine label and the other has a fluorescein label. Laser scanning confocal microscopy techniques may be used to independently detect the fluorescence of each label, thereby locating each of the shell and encapsulant. Where the component signals are located at the same point as the signals from the shell, it is understood that the component resides within a pore of the shell.

The general shape of the shell, and therefore the shape of the capsule, is not particularly limited. In practice however, the shape of the capsule may be dictated by its method of preparation. In the preparation methods described herein, a capsule shell may be prepared using fluidic droplet formation techniques. Typically, the shell material is formed at the boundary of a discrete (or discontinuous) phase in a continuous phase. For example, one phase may be an aqueous phase, and the other may be a water immiscible phase. The discrete region may be a droplet, having a substantially spherical shape. The shell formed is therefore also substantially spherical.

In certain embodiments, a capsule may be obtained when the shell has a substantially spherical shape. This capsule may be subjected to a drying step, which reduces the amount of solvent (for example, water) in and around the capsule. As a result of this step, the capsule shrinks in size. At first the shell maintains a substantially spherical shape. After further drying, the capsule sphere may partially or fully collapse in on itself. The structural integrity of the capsule is maintained and the shell simply distorts to accommodate changes in the internal volume. Thus, the capsules of the invention include those capsules where the shell is an at least partially collapsed sphere.

Given the formation of the capsule shell at the boundary of the discrete region (for example, a droplet), references to the dimensions of a droplet may also be taken as references to the dimension of the capsule. The capsule shell may form prior to a drying step.

The inventors have established that capsules that have been shrunk, for example by desolvation, may subsequently be returned to their original substantially spherical shape, by, for example, resolvating the capsule.

The shape of a capsule may be determined by simple observation of the formed capsule using microscopy, such as bright field microscopy, scanning electron microscopy or transmission electron microscopy. Where the shell material comprises a label, the detection of the label through the shell will reveal the capsule shape. For example, where the label is a fluorescent label, laser scanning confocal microscopy may be used to locate the shell material and its shape.

The size of the capsule is not particularly limited. In one embodiment, the capsule is a microcapsule and/or a nanocapsule.

In one embodiment, each capsule has an average size of at least 0.1, 0.2, 0.5, 0.7, 1, 5, 10, 20, 30, 40, 50, 100 or 200 µm in diameter.

In one embodiment, each capsule has an average size of at most 400, 200, 100, 75 or 50 µm in diameter.

In one embodiment, the capsule size is in a range where the minimum and maximum diameters are selected from the embodiments above. For example, the capsule size is in range from 10 to 100 µm in diameter.

Average size refers to the numerical average of measured diameters for a sample of capsules. Typically, at least 5 capsules in the sample are measured. A cross section measurement is taken from the outmost edges of the shell.

The cross-section of a capsule may be determined using simple microscopic analysis of the formed capsules. For example, the formed capsules may be placed on a microscope slide and the capsules analysed. Alternatively, the capsule size may be measured during the preparation process, for example as the capsules are formed in a channel of a fluidic device (i.e. in line).

The measurement of the cross section may also be achieved using techniques related to the detection of a detectable label or functionality present within the shell material. As mentioned above in relation to detection and location of the encapsulated component, the shell material may comprise a fluorescent label which may be detected by laser scanning confocal microscopy techniques. The presence of multiple labels within and around the capsule shell allows the cross-sectional shape to be determined, and the largest cross-section measured.

In the preparation method described herein a capsule is prepared using a fluidic droplet generation technique. The capsule shell is formed in a droplet, which is created in a channel of a fluidic droplet generating device, at the boundary of the aqueous phase of the droplet with the continuous phase. The size of the capsule is therefore substantially the same as that of the droplet.

The present inventors have established that the capsules of the invention may be prepared with a low size distribution. This is particularly advantageous, as a large number of capsules may be prepared, each with predictable physical and chemical characteristics.

In one embodiment, the capsule diameter has a relative standard deviation (RSD) of at most 0.5%, at most 1%, at most 1.5%, at most 2%, at most 4%, at most 5%, at most 7%, or at most 10%.

The relative standard deviation is calculated from the standard deviation divided by the numerical average and multiplied by 100. The size of the capsule refers to the largest cross section of the capsule, in any section. The cross-section of a substantially spherical capsule is the diameter.

The shell defines an internal cavity which is suitable for encapsulating a component. The size of the internal space will generally correspond to the size of the capsule itself. Thus, the dimension, for example the diameter, of the internal space may be selected from any one of the diameter values given above for the shell itself.

Where the size of the capsule is measured, the diameter refers to the distance from the outermost edge to outmost edge of the shell material of two opposing points, as mentioned above. Where the size of the internal space is measured, the diameter refers to the distance from the innermost edge to innermost edge of the shell material of two opposing points The inventors have established techniques that allow the shell outer and inner edges to be determined. For example, the presence of a detectable label within the shell material allows the outermost and innermost edges of the shell to be determined. If these edges can be detected, the thickness of the shell may be determined.

Typically, the diameter as measured from outermost to outermost edge is not significantly different to the diameter as measure from innermost to innermost edge. The difference is the thickness of the shell at the two opposing points.

In one embodiment, the shell has a thickness of at least 0.02, at least 0.05, at least 0.1, at least 0.5, at least 1.0, at least 2.0 or at least 5.0 μm.

As previously noted, the shell has pores. In one embodiment, the pores may be of a size to permit the passage of material therethrough. For example, components encapsulated within the capsule may pass through the pores of the shell to be released from the capsule. Conversely, the pores may be of sufficient size to allow components to pass into the shell internal space, and thereby become encapsulated. Such may be referred to as a passive diffusion encapsulation step. Such a technique may be used to provide a capsule having an encapsulant within. As described herein, the present inventors have provided alternative methods for the encapsulation of material in the shell preparation step. Such methods allow for a more efficient loading of the capsule with material, as the material is entirely encapsulated within the shell.

In one embodiment, the pores may be of a size that is too small to permit passage of material therethrough. For example, components encapsulated within the capsule may be prevented from passing through the pores of the shell, and therefore cannot be released from the capsule. Such material may be released from the capsule by, for example, disrupting the cucurbituril complexes that hold the shell together. Disruption of the shell in this way creates larger pores through which material may pass.

It is believed that the pore size may be increased upon solvation of a previously desolvated capsule. As the capsule shrinks, the porosity of the capsule may decrease as the shell material folds over, thereby at least partially blocking some of the pores.

The size of a pore may be gauged experimentally using a range of encapsulated components each having a different cross-section, such as a different diameter. The cross-section may be known or may be predicted based on an understanding of the likely configuration of the component. The pore size may be determined based on which components are released from the capsule and which are not.

The cross-section, typically diameter, of a component may be predicted based on the calculated radius of gyration for each encapsulated component. Such calculations are most suitable for determining the size of small globular particles, and may be used in relation to polymeric systems, such as polypeptides, polynucleotides and polysaccharides. Methods for the calculation of radius of gyration are described in Andrieux et al. *Analytical Chemistry* 2002, 74, 5217, which is incorporated by reference herein.

A capsule comprising an encapsulated component may be prepared using the methods described herein. Once the capsule (with encapsulant) is prepared, the capsule and its aqueous surroundings may be analysed for loss of material from within the shell out to the external aqueous phase. The encapsulated compounds may have an analytical label to aid detection. Suitable labels include fluorescent labels which are detectable using standard fluorescence microscopy techniques.

In one embodiment, dextran compounds of differing molecular weight may be used as test compounds to determine the pore size of a formed capsule. The dextran may be labelled, and preferably with a fluorescent label.

Dextran compounds of differing molecular weight are readily available from commercial sources, including, for example, Sigma Aldrich. Dextrans having an average molecular weight of from 1,000 to 500,000 are available. Dextran with a molecular weight of 70 kDa has a radius of gyration of approx. 8 nm, whilst dextran with a molecular weight of 150 kDa has a radius of gyration of approx. 11 nm (see Granath *Journal of Colloid Science* 1958, 13, 308). Dextran compounds having a fluorescent label, such as fluorescein isothiocyanate, are also available from commercial sources, including, again, Sigma Aldrich.

In one embodiment, the pore size is at most 20, at most 15, at most 10, at most 5, at most 1 or at most 0.5 μm.

In one embodiment, the pore size is at most 500, at most 200, at most 100, at most 50, or at most 20 nm.

In one embodiment, the pore size is at least 0.5, at least 1, or at least 5 nm.

In one embodiment, the pore size is in a range where the minimum and maximum pore sizes are selected from the embodiments above. For example, the pore size is in range 1 to 20 nm.

As an alternative to dextran, protein standards may be used instead. As an alternative to the labelled compounds described above, it also possible to detect the compound released from the capsule using mass spectroscopy, or protein gel electrophoresis (for protein standards).

Surface area, porosity and pore size may also be determined experimentally using BET gas absorption techniques.

As expected, the shell pore size is influenced by the amount of cucurbituril present in the complexable composition from which the capsule may be prepared. Increasing the amount of cucurbituril present in the complexable composition is believed to increase the amount of crosslinking with the network, thereby reducing the size of the pores in the formed shell material.

The capsule shell may comprise one or more layers of material. The layers of the material may be linked, for example by a ternary supramolecular complex of cucurbituril with a first guest molecule present in one layer and a second guest molecule present in a second layer. Additionally, or alternatively, the layers of the material may be linked by a first building block having a plurality of guest molecules, where one guest molecule forms a ternary complex with a cucurbituril and another guest molecule present in a first layer, and another guest molecule forms a ternary complex with a cucurbituril and another guest molecule present in a second layer. In these embodiments the shell may be viewed as a mesh extending in three dimensions. Although the shell may have a depth of material, such as a thickness described herein, it is understood that the formation of the shell will nevertheless provide an internal space in which a component may reside. Thus, the present invention is not intended to encompass particles having no internal space.

Alternatively the capsule shell may comprise a plurality of concentric layers of network material that are not interlinked. In any such embodiment, the reference to capsule size refers to the cross section of the outermost shell.

As discussed above, the shell material may include detectable labels or detectable functionalities A detectable functionality is functionality of a capsule shell component having a characteristic that is detectable over and above the characteristics that are present in other components of the capsule, or even other functionalities of the same component.

The detectable functionality may refer to a particular chemical group that gives rise to a unique signal in, for example, IR, UV-VIS, NMR or Raman analysis. The functionality may be a radioactive element, Typically a part of the shell material or the encapsulant is provided with a detectable label, as the introduction of a chosen label allows the use of techniques that are most appropriate for the property that is to be measured. Described herein are building blocks having fluorescent detectable labels. Also described herein are building blocks that are capable of providing a surface enhanced resonance effect.

The she may have additional functionality on its inner and/or outer surfaces. Described herein are building blocks having functionality to improve solubility, to aid detection, reactive functionality for later elaboration of the shell, and catalysts, amongst others.

The capsule shell of the invention is stable and may be stored without loss of the shell structure. The integrity of the shell therefore allows the capsule to be used as a storage vessel for an encapsulant. The capsules of the invention are thermally stable and the shell is known to maintain its integrity at least up to 100° C. The capsules of the invention are also stable at reduced pressures (i.e. below ambient pressure). The shell is known to maintain its integrity down to at least 20 Pa, The capsules of the invention have a long shelf life. The present inventors have confirmed that structural integrity is maintained for at least 10 months.

The structural integrity of the shell is in part due to the strength of the cucurbituril guest-host complex, which is described in more detail below.

Additional or Alternative Capsule Features

The capsule shell has pores. The porosity is adjustable by appropriate changes in the stoichiometry of the reagents used to form the capsule. Increasing the crosslinking between building blocks will decrease the size of the pores in the capsule. Alternatively, the building blocks may be selected so as to provide a shell material that has increased or decrease porosity. Where a encapsulant or relatively small size is to be encapsulated, the capsule is prepared with pores of relatively small diameter, thereby to limit or prevent loss of the encapsulant out of the shell. Where a relatively large encapsulant is to be encapsulated, the pore size may be larger.

As noted above, the shell may have additional functionality on its inner and/or outer surfaces. In some embodiments, the functionality is provided for later chemical functionalisation of the capsule shell, for example as a reaction site for linking to a compound having a particularly desirable reactivity.

In one embodiment, the shell has a chemical functional group available for reaction on the outer and/or the inner surface of the capsule. The chemical functional group is selected from the group consisting of hydroxyl, amine (preferably primary and secondary amine), carboxy, thiol, ester, thioester, carbonate, urethane, and thiourea.

In one embodiment the shell is linked to a functional compound.

In one embodiment, the functional compound is an analytical label to aid detection and quantification of the capsule. Such is described in the section above.

The functional compound may be catalytic (including enzymatic), antifungal, herbicidal, or antigenic.

The functional compound may have surface adhesion properties. Such functionality may be used to attach the capsule to a surface, either covalently or non-covalently.

The functional compounds may be capable of binding to (or sequestering) a compound or ion. Such functionality may be of assistance in purification, such as filtering, and for the capture of toxic and non-toxic elements and compounds.

In one embodiment, the functional compound is a biomolecule.

In one embodiment, the functional compound is a polypeptide, a polysaccharide, a polynucleotide, or a lipid.

Examples of polypeptides include enzymes, antibodies, hormones and receptors.

The functionality may be introduced into the shell by appropriate choice of building block material. Thus, where the building block is a polymer, suitable functionality may be incorporated into the monomers of the polymer, which monomer may be present within the polymer backbone, or on a side chain. Where the building block is a particle, the surface of that particle may be suitably functionalised.

Where a functional molecule is present on a surface of the shell, this molecule may be added after the capsule is formed. The functional molecules may be linked to the shell using a chemical functional group that has been introduced for this purpose.

In principle, the cucurbituril may have functionality that is available for reaction. However, this is less preferred.

Where necessary, appropriate protecting groups may be used to protect the functionality during the capsule preparation procedure. The protecting groups may be removed later, as and when required.

Complex

The capsule shell comprises a network that is held together by a supramolecular handcuff. The complex that forms this supramolecular handcuff is based on a cucurbituril hosting one guest (binary complex) or two guests (ternary complex). The cucurbituril forms a non-covalent bond to each guest. The present inventors have established that complexes of cucurbituril are readily formed and provide robust non-covalent linkages between building blocks. The formation of the complex is tolerant of many functionalities within the building blocks. One of the present inventors has demonstrated that polymer networks may be prepared using a cucurbituril handcuff. However, until now, the formation of precise polymer structures, such as capsules, using cucurbituril has been described.

In one embodiment, the shell is a network having a plurality of complexes, wherein each complex comprises cucurbituril hosting a first guest molecule and a second guest molecule. The first and second guest molecules are covalently linked to a first building block, or to a first building block and a second building block.

Where the complex comprises two guests within the cucurbituril cavity, the association constant, $K_a$, for that complex is at least $10^3$ $M^{-2}$, at least $10^4$ $M^{-2}$, at least $10^5$ $M^{-2}$, at least $10^6$ $M^{-2}$, at least $10^7$ $M^{-2}$, at least $10^8$ $M^{-2}$, at least $10^9$ $M^{-2}$, at least $10^{10}$ $M^{-2}$, at least $10^{11}$ $M^{-2}$, or at least $10^{12}$ $M^{-2}$.

Where a cucurbituril hosts two guest molecules, the guest molecules may be the same or they may be different. A cucurbituril that is capable of hosting two guest molecules may also be capable of forming a stable binary complex with a single guest. The formation of a ternary guest-host complex is believed to proceed via an intermediate binary complex. Within the shell, there may be present a binary complex formed between a guest molecule and a cucurbituril. The binary complex may be regarded as a partially formed ternary complex that has not yet formed a non-covalent bond to another guest molecule.

In one embodiment, the shell is a network having a plurality of complexes, wherein each complex comprises cucurbituril hosting one guest molecule, and each cucurbituril is covalently linked to at least one other cucurbituril. The guest molecules are covalently linked to a first building block, or to a first building block and a second building block.

Where the complex comprises one guest within the cucurbituril cavity, the association constant, $K_a$, for that complex is at least $10^3$ $M^{-1}$, of at least $10^4$ $M^{-1}$, of at least $10^5$ $M^{-1}$, of at least $10^6$ $M^{-1}$, of at least $10^7$ $M^{-1}$, of at least $10^8$ $M^{-1}$, of at least $10^9$ $M^{-1}$, of at least $10^{10}$ $M^{-1}$, of at least $10^{11}$ $M^{-1}$ or of at least $10^{12}$ $M^{-1}$.

In one embodiment, the guest is a compound capable of forming a complex which has an association constant in the range $10^4$ to $10^7$ $M^{-1}$.

In one embodiment the formation of the complex is reversible. The decomplexation of the complex to separate the guest or guests may occur in response to an external stimulus, including, for example, a competitor guest compound. Such decomplexation may be induced in order to provide additional or larger pores in the capsule through which an encapsulated material may pass.

As noted above in relation to the capsule shell, the complex of cucurbituril with one or two guests is the non-covalent link that links and/or interlinks the building blocks to from a supramolecular network of material. The complex is thermally stable and does not separate at reduced pressure, as explained for the shell.

Network

The formation of a supramolecular complex serves to link and/or interlink building blocks, thereby forming a network of material. This is the capsule shell.

Two types of network are provided. The first type is based on the formation of a plurality of ternary complexes, each complex comprising a cucurbituril host with a first guest molecule and a second guest molecule. The second type is based on the formation of a plurality of binary complexes, each complex comprising a cucurbituril host with a first guest molecule. In this second type, each cucurbituril is covalently linked to a least one other cucurbituril. These types of network may be combined with a shell.

Where a building block is provided with a plurality of guest molecules, all of the guest molecules need not participate in a complex with cucurbituril. Where the network is based on linking between ternary structures, a guest molecule of a building block may be in a binary complex with a cucurbituril. The binary complex may be regarded as a partially formed ternary complex that has not yet combined with a further guest molecule to generate the ternary form.

Throughout the description references are made to a building block, a first building block and a second building block. It is understood that a reference to such is a reference to a collection of the individual molecules, particles, polymers etc. that are the building blocks. Where a reference is intended to an individual building block molecule, particle etc. the term single is used in reference to the building blocks e.g. a single first building block.

The networks described below are the basic networks that are obtainable from the compositions described. It is understood that the present inventions extends to more complex networks that are obtainable from compositions comprising further building blocks.

Network of Ternary Complexes Based on Cucurbituril

This network is obtainable from the assembly of a first guest molecule and a second guest molecule together with a cucurbituril host. The guest molecules may be provided on one or two (or more) building blocks as described below.

In one embodiment, a network is obtainable or obtained from the complexation of a composition comprising a cucurbituril, a first building block covalently linked to a plurality of first cucurbituril guest molecules and a second building block covalently linked to a plurality of second cucurbituril guest molecules, wherein a first guest molecule and a second guest molecule together with cucurbituril are suitable for forming a ternary guest-host complex.

The ternary complex serves to non-covalently link the first and second building blocks. A single first building block may form a plurality of non-covalent links to a plurality of second building blocks. Similarly, a single second building block may form a plurality of non-covalent links to a plurality of first building blocks. In this way, a network of material is established.

It is noted that in some embodiments, the first and second guest molecules may be identical. Therefore the first and second building blocks may differ in their compositions. In some embodiments, the first and second building blocks may be identical. In this case, the first and second guest molecules are different.

FIGS. 11-16 illustrate is a schematic structure of a basic network formed between cucurbituril, a single first building block and two single second building blocks. In FIGS. 11-16, the guest molecules are depicted as rectangles which are covalently linked (vertical line) to a building block (horizontal line). The vertical line may depict a direct covalent bond or a linker to the building block. The building block may be a polymeric molecule, a particle or the like, as described herein.

As shown in FIG. 11, some of the first guest molecules (unshaded rectangles) of the first building block are in complex with cucurbituril hosts (barrels) and second guest molecules (shaded rectangles) of the second building blocks.

It is apparent that not all guest molecules present participate in a complex in the final network. Each of the first and second building blocks may form complexes with other second and first building blocks respectively. The guest molecules are shaded for ease of understanding. However, as explained herein, the guest molecules of the first and second building blocks may be the same.

In an alternative embodiment, a network is obtainable or obtained from the complexation of a composition comprising a cucurbituril and a first building block covalently linked to a plurality of first cucurbituril guest molecules and a plurality of second cucurbituril guest molecules, wherein a first and a second guest molecule together with cucurbituril are suitable for forming a ternary guest-host complex.

The ternary complex serves to non-covalently link and/or interlink the first building block. A single first building block may form a plurality of non-covalent links to a plurality of other first building blocks. Additionally, or alternatively, a single first building block may form a plurality of non-covalent interlinks with itself, thereby to crosslink the single first building block.

As before, the first and second guest molecules may be identical.

FIG. 12 depicts a schematic structure of a basic network formed between cucurbituril and two single first building blocks each having a plurality of first and second guest molecules. Some of the first guest molecules (unshaded rectangles) of the first building block are in complex with cucurbituril hosts (barrels) and second guest molecules (shaded rectangles) of another first building block. It can be seen from the network illustrated that a first building block may form intramolecular complexes, thereby crosslinking a single first building block.

It is apparent that not all guest molecules present need participate in a complex in the final network. Each of the first building blocks may form complexes with other first building blocks, or with other parts of the same building block. As explained herein, the first and second guest molecules may be the same.

Optionally, the composition further comprises a second building block covalently linked to one or more third cucurbituril guest molecules, one or more fourth cucurbituril guest molecules or both, wherein a third and a fourth molecule together with cucurbituril are suitable for forming a ternary guest-host complex, or the first and fourth guest molecules together with cucurbituril are suitable for forming a ternary guest-host complex, or the second and third guest molecules together with cucurbituril are suitable for forming a ternary guest-host complex.

Where the second building block is provided with a plurality of third and fourth guest molecules, the ternary complex serves to non-covalently link and/or interlink the second building block. A single second building block may form a plurality of non-covalent links to a plurality of other second building blocks. Additionally, or alternatively, a single second building block may form one or more non-covalent interlinks with itself, thereby to crosslink the single second building block.

The third and fourth guest molecules may be suitable for forming complexes with the first and second guest molecules of the first building block. In one embodiment, the first and third guest molecules are the same. In one embodiment the second and fourth guest molecules are the same. Here, the ternary complex serves to non-covalently link the first and second building blocks, for example through a complex of the first and fourth guest molecules and/or through a complex of the second and third guest molecules.

Thus, a single first building block may form a plurality of non-covalent links to a plurality of second building blocks. Similarly, a single second building block may form a plurality of non-covalent links to a plurality of first building blocks. In this way, a network of material is established. The building blocks may also form intermolecular non-covalent bonds as described previously.

Where a second building block is covalently linked to one or more third guest molecules or one or more fourth guest molecule, the first and fourth molecules together with cucurbituril are suitable for forming a ternary guest-host complex, and the second and third molecules together with cucurbituril are suitable for forming a ternary guest-host complex. Thus, the ternary complex serves to non-covalently link the second building block to the first building block.

FIG. 13 depicts a schematic structure of a basic network formed between cueurbituril, three single first building blocks each having a plurality of first and second guest molecules, and two second building blocks each having a plurality of third and fourth guest molecules. Some of the first guest molecules (unshaded rectangles) of the first building block are in complex with cucurbituril hosts (barrels) and second guest molecules (shaded rectangles) of another first building block. Some of the third guest molecules (partially shaded rectangles) of the second building block are in complex with cucurbituril hosts (barrels) and fourth guest molecules (dashed rectangles) of another second building block. A the first guest molecule of the first building block is in complex with a cucurbituril host and a fourth guest molecule (dashed rectangles) of a second building block. A second guest molecule of the first building block is in complex with a cucurbituril host and a third guest molecule of a second building block.

The first and third guest molecules may be the same. The second and fourth guest molecules may be the same.

A second building block may be covalently linked to one guest molecule (which may be a third or a fourth guest molecule). In this embodiment, the second building block is not capable of forming a plurality of links to other building blocks. As such, the building block would not contribute to the formation of across links within the network. However, the second building block may be provided in order to introduce into the network a particular physical or chemical characteristic that is possessed by the second building block. For example, the second building block may comprise a detectable label or a functional group, such as a solubilising group. The incorporation of the second building block into the network therefore allows the modification of the physical or chemical characteristics of the overall network.

Figure 14 depicts a schematic structure of a basic network formed between cucurbituril, two single first building blocks each having a plurality of first and second guest molecules, and also including a single second building block, which is covalently linked to one fourth guest molecule, and a detectable label. Some of the first guest molecules (unshaded rectangles) of the first building block are in complex with cucurbituril hosts (barrels) and second guest molecules (shaded rectangles) of another first building block. A first guest molecule of the first building block is in complex with a cucurbituril host and a fourth guest molecule. The detectable label (partially shaded circle) may be provided in order to allow identification of the resulting network.

Network of Binary Complexes Based on a Plurality of Covalently Linked Cucurbiturils This network is obtainable from the assembly of a first guest molecule together with a cucurbituril host, which host is covalently linked to one or more other cucurbiturils. The guest molecules may be provided on one, or two (or more) building blocks as described herein.

The covalently linked cucurbiturils serve to link building block molecules through the plurality of complexes that are formed within each of the covalently linked cucurbiturils.

FIG. 15 depicts a schematic structure of a basic network formed between a plurality of covalently linked cucurbiturils and two single first building blocks each having a plurality of first guest molecules. Some of the first guest molecules (unshaded rectangles) of each of the single first building block are in a binary complex with cucurbituril hosts (barrel). The cucurbiturils are linked, thereby to form a link between each of the first building blocks.

It is apparent that not all guest molecules present need participate in a complex in the final network. Each of the single first building blocks may form complexes with other first building blocks respectively, or may form an intramolecular crosslink with another portion of the same building block. As explained herein, the guest molecules of the first and second building blocks may be the same. In FIG. 15, one of the first building blocks may be replaced with a second building block which is covalently linked to a second guest molecule. The second guest molecule is one that is capable of forming a binary complex with the cucurbituril. The second guest molecule may be the same as the first guest molecule.

In FIG. 15, two cucurbiturils are shown linked together. The present invention encompasses the use of systems where more than two cucurbiturils are linked together. For example multiple cucurbiturils may be pendant to a polymeric molecule.

Network of Ternary Complexes Based on a Plurality of Covalently Linked Cucurbiturils It will be apparent from the description of the networks above, that each of the cucurbituril hosts in the plurality of covalently linked cucurbiturils may be suitable for forming ternary complexes. Thus, the plurality of covalently linked cucurbiturils may be used in place of the cucurbituril described for use in the network of ternary complexes based on cucurbituril.

FIG. 16 depicts a structural schematic of a basic network formed between a plurality of covalently linked cucurbiturils, two single first building blocks each having a plurality of first guest molecules, and two single second building blocks each having a plurality of second guest molecules. Some of the first guest molecules (unshaded rectangles) of the first building block are in tertiary complex with a cucurbituril host (barrel) and the second guest molecules (shaded rectangles) of the second building block The cucurbiturils are linked, thereby to form a link between each of the first and second building blocks.

As before, the first and second guest molecules may be the same. Each of the first and second building blocks may form complexes with other second and first building blocks respectively. Other permutations are possible, for example, where the plurality of covalently linked cucurbiturils has greater than two cucurbiturils.

Other Networks

Described above are the basic networks of the invention that are obtained or obtainable from the compositions described. It will be clear to one of skill in the art that the compositions described may include further building blocks, for example third and fourth building blocks, each linked to one or more cucurbituril guest molecules. The present invention also covers capsules where the shell comprises a mixture of any one of the networks described above. Such are obtainable from compositions comprising an appropriate selection of cucurbituril, covalently linked cucurbiturils, first building block and second building block as appropriate.

The invention also relates to a capsule having a shell that is a network comprising different cucurbiturils. Different cucurbiturils may be chosen in order to obtain a network that is based on ternary and binary complexes. Different cucurbiturils may be chosen in order to generate networks that result from the selective complexation of each cucurbituril for different guest molecules, which may be present on the same or different building blocks.

Cucurbituril

The present invention provides use of cucurbituril as a supramolecular handcuff to link and/or crosslink building blocks. The cucurbituril may be used to form ternary complexes with first and second guest molecules present on one or more building blocks. The formation of such complexes links individual building blocks thereby to form a network of material. This network is the shell of the capsule.

Additionally, or alternatively, a plurality of covalently linked cucurbiturils is provided and each cucurbituril may be used to form binary complexes with a guest molecule present on one or more building blocks. The formation of a binary complex with each of the covalently linked cucurbiturils thereby forms a network of material. This network is the shell of the capsule.

In one embodiment, the cucurbituril is capable of forming a ternary complex. For example, CB[8], is capable of forming a ternary complex.

In one embodiment, the cucurbituril is capable of forming a binary complex. For example, CB[7], is capable of forming a binary complex.

In one embodiment, the cucurbituril is capable of forming ternary and binary complexes. For example, CB[8], is capable of forming a ternary or a binary complex, depending upon the nature of the guest.

In one embodiment, the cucurbituril is a CB[5], CB[6], CB[7], CB[8], CB[9], CB[10], CB[11] or CB[12] compound.

In one embodiment, the cucurbituril is a CB[6], CB[7], or CB[8] compound.

In one embodiment, the cucurbituril is a CB[8] compound.

In one embodiment, references to a cucurbituril compound are references to variants and derivatives thereof.

Cucurbituril compounds differ in their water solubility. The methods of capsule preparation may be adapted to take into account this solubility, as described later. Therefore the choice of cucurbituril compound is not limited by its aqueous solubility.

In one embodiment, the cucurbituril compound has a solubility of at least 0.01 mg/mL, at least 0.02 mg/mL, at least 0.05 mg/mL, or at least 0.10 mg/mL.

In one embodiment, the solubility refers to aqueous solubility (i.e. an aqueous phase).

In one embodiment, the solubility refers to solubility in a water immiscible phase, such as an oil phase or an organic phase.

Cucurbit[8]uril (CB[8]; CAS 259886-51-6) is a barrel shaped container molecule which has eight repeat glycoluril units and an internal cavity size of 479 $Å^3$ (see structure below). CB[8] is readily synthesised using standard techniques and is available commercially (e.g. Sigma-Aldrich, MO USA).

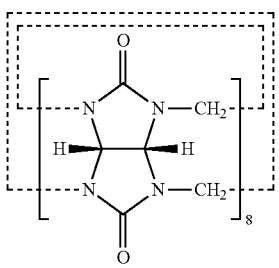

In other aspects of the invention, CB[8] variants are provided and find use in the methods described herein.

A variant of CB[8] may include a structure having one or more repeat units that are structurally analogous to glycoluril. The repeat unit may include an ethylurea unit. Where all the units are ethylurea units, the variant is a hemicucurbituril. The variant may be a hemicucurbit[12]uril (shown below, see also Lagona et al. *Angew. Chem. Int. Ed.* 2005, 44, 4844).

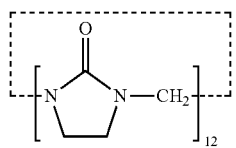

In other aspects of the invention, cucurbituril derivatives are provided and find use in the methods described herein. A derivative of a cucurbituril is a structure having one, two, three, four or more substituted glycoluril units. A substituted cucurbituril compound may be represented by the structure below:

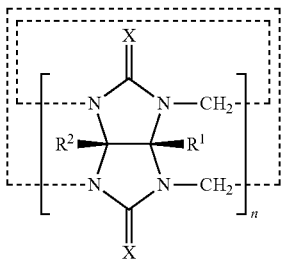

wherein:
n is an integer of at least 5;
and for each glycoluril unit
  each X is O, S or $NR^3$, and
  —$R^1$ and —$R^2$ are each independently selected from —H and the following optionally substituted groups: —$R^3$, —OH, —$OR^3$, —COOH, —$COOR^3$, —$NH_2$, —$NHR^3$ and —$N(R^3)_2$ where —$R^3$ is independently selected from $C_{1-20}$alkyl, $C_{6-20}$carboaryl, and $C_{5-20}$heteroaryl, or where -$R^1$ and/or -$R^2$ is —$N(R^3)_2$, both —$R^3$ together form a $C_{5-7}$ heterocyclic ring; or together —$R^1$ and —$R^2$ are $C_{4-6}$alkylene forming a $C_{6-8}$carbocyclic ring together with the uracil frame.

In one embodiment, one of the glycoluril units is a substituted glycoluril unit. Thus, —$R^1$ and —$R^2$ are each independently —H for n–1 of the glycoluril units In one embodiment, n is 5, 6, 7, 8, 9, 10, 11 or 12.
In one embodiment, n is 5, 6, 7, 8, 10 or 12.
In one embodiment, n is 8.
In one embodiment, each X is O.
In one embodiment, each X is S.
In one embodiment, $R^1$ and $R^2$ are each independently H.
In one embodiment, for each unit one of $R^1$ and $R^2$ is H and the other is independently selected from —H and the following optionally substituted groups: —$R^3$, —OH, —$OR^3$, —COOH, —$COOR^3$, —$NH_2$, —$NHR^3$ and —$N(R^3)_2$. In one embodiment, for one unit one of $R^1$ and $R^2$ is H and the other is independently selected from —H and the following optionally substituted groups: —$R^3$, —OH, —$OR^3$, —COOH, —$COOR^3$, —$NHR^3$ and —$N(R^3)_2$. In this embodiment, the remaining glycoluril units are such that $R^1$ and $R^2$ are each independently H.

Preferably —$R^3$ is $C_{1-20}$alkyl, most preferably $C_{1-6}$alkyl. The $C_{1-20}$alkyl group may be linear and/or saturated. Each group —$R^3$ may be independently unsubstituted or substituted. Preferred substituents are selected from: —$R^4$, —OH, —SH, —COOH, —$COOR^4$, —$NH_2$, —$NHR^4$ and —$N(R^4)_2$, wherein —$R^4$ is selected from $C_{1-20}$alkyl, $C_{6-20}$carboaryl, and $C_{5-20}$heteroaryl. The substituents may be independently selected from —COOH and —$COOR^4$.

In some embodiments, —$R^4$ is not the same as —$R^3$. In some embodiments, —$R^4$ is preferably unsubstituted.

Where —$R^1$ and/or —$R^2$ is —$OR^3$, —$NHR^3$ or —$N(R^3)_2$, then —$R^3$ is preferably $C_{1-6}$alkyl. In some embodiments, —$R^3$ is substituted with a substituent —$OR^4$, —$NHR^4$ or —$N(R^4)_2$. Each —$R^4$ is $C_{1-6}$alkyl and is itself preferably substituted In some embodiments of the invention there is provided the use of a plurality of covalently linked cucurbiturils. Such covalently linked cucurbiturils are suitable for forming networks based on the complexation of the cucurbituril with guest molecules of a building block. The complexes formed may be ternary or binary complexes.

A cucurbituril may be covalently linked to another cucurbituril via a linker group that is a substituent at position $R^1$ or $R^2$ at one of the glycoluril units in the cucurbituril as represented in the structure shown above. There are no particular limitations on the covalent link between the cucurbiturils. The linker may be in the form of a simple alkylene group, a polyoxyalkylene group or a polymer, such as a polymeric molecule described herein for use in the building block. Where the linker is a polymeric molecule, the cucurbiturils may be pendant to that polymer.

Building Block

Cucurbituril is used as a supramolecular handcuff to join together one or more building blocks. The formation of a complex of the cucurbituril with suitable guest components that are linked to the building blocks forms a network of material. This material is the capsule shell. The complex non-covalently crosslinks the building block or non-covalently links the building block to another building block.

It is understood from the above that a building bock is an entity that serves to provide structure to the formed network. The building block also serves as the link between a plurality of guest molecules, and it may therefore also be referred to as a linker. In some embodiments, a building block is provided for the purpose of introducing a desirable physical or chemical characteristic into the formed network. As mentioned above in relation to the network, a building block may include a functionality to aid detection and characterisation of the shell. Such building blocks need not necessarily participate in a crosslink.

A building block, such as a first building block, may be covalently linked to a plurality of cucurbituril guest molecules. A building block will therefore non-covalently link to a plurality of cucurbiturils, which cucurbiturils will non-covalently link to other building blocks, thereby to generate a network of material.

A building block, such as a first building block or a second building block, may be covalently linked to a plurality of cucurbituril guest molecules. In one embodiment, a building block is covalently linked to at least 3, at least 4, at least 5, at least 10, at least 20, at least 50, at least 100, at least 500, at least 1,000, at least 2,000, at least 5,000 or at least 10,000 cucurbituril guest molecules.

In certain embodiments, building blocks covalently linked to one or more cucurbituril guest molecules may be used. However, such building blocks are used only in combination with other building blocks that are covalently linked to at least two cucurbituril guest molecules.

In one embodiment, there is provided a first budding block covalently linked to a plurality of first guest molecules and a second building block covalently linked to a plurality of second guest molecules. Each of the first and second building blocks may be covalently linked to at least the number of guest molecules described above.

In one embodiment, there is provided a first building block covalently linked to a plurality of first guest molecules and covalently linked to a plurality of second guest molecules. The first building block may be covalently linked to at least the number of guest molecules described above, which numbers may refer independently to the number of first guest molecules and the number of second guest molecules.

In one embodiment, there is provided a second building block covalently linked to one or more third guest molecules and/or covalently linked to a one or more fourth guest molecules. In one embodiment, the second building block is covalently linked to at least the number of guest molecules described above, which numbers may refer independently to the number of third guest molecules and the number of fourth guest molecules. Such a second building block may be used together with the first building block described in the paragraph above.

Throughout the description, references are made to first and second building blocks. In some embodiments, the first and second building blocks may be distinguished from each other owing to differences, at least, in the structure of the building blocks themselves. In some embodiments, the structures of the first and second building blocks are the same. In this case, the building blocks may be distinguished from each other owing to differences, at least, in the guest molecules that are covalently linked to each of the first and the second guest molecules. Thus the terms first and second are intended to convey a difference between the first building block together with its guest molecules and the second building block together with its guest molecules.

The building blocks are not particularly limited, and the building block includes compounds and particles, and may encompass assemblies of either of these. The guest molecules are covalently linked to some portion of the building block.

At its simplest a building block is a linker for the connection of guest molecules.

In one embodiment the building block is a polymeric molecule or a particle.

Advantageously, a building block may be provided with certain functionality to aid the formation of the capsule shell, or to improve its physical or chemical properties.

In one embodiment, the building block is provided with functionality to alter, or preferably improve, water solubility. The functionality may take the form of a solubilising group, such as a group comprising polyethylene glycol functionality. Other examples include groups comprising amino, hydroxy, thiol, and carboxy functionality.

In one embodiment, the building block is provided with functionality to aid detection or analysis of the building block, and to aid detection or analysis of the formed shell. Advantageously, such functionality may also aid the detection of material encapsulated within the shell. The functionality may take the form of a detectable label, such as a fluorescent label.

In one embodiment, the building block is provided with reactive functionality for use in the later elaboration of the shell material. The reactive functionality may be protected for the shell forming reactions, then later deprotected to reveal the functionality. The functionality may be a group comprising amino, hydroxy, thiol, and carboxy functionality.

Where the building block is provided with reactive functionality is provided, this functionality may be suitable for linking the building block (and therefore the formed capsule) to a surface.

In one embodiment, the building block is provided with a catalyst for later use in the catalysis of a reaction at or near the shell surface. The catalyst may be provided at the inner or outer edges of the shell thereby to catalyse internal and/or external reactions.

In one embodiment, the building block is chosen for its ability to influence the opticoelectronic properties of the encapsulant Additionally or alternatively, the building block may be chosen for its ability to be influenced by the encapsulant. The building block may be suitable for transferring signals from the encapsulant to outside environment.

In one embodiment a building block is capable of providing a surface enhanced resonance effect.

Where functionality is provided it may be located at the outer side of, the inner side of and/or within the shell. Thus, the functionality may be provided in connection with the improvements related to the environment outwith the shell, within the internal space (the space for holding an encapsulant) of the shell and/or within the shell (within the network of shell material).

For the purposes of the methods described herein, the building block, together with the guest molecules to which it is covalently linked, should be soluble, for example in the second phase.

In one embodiment, the building block has a solubility of at least 0.01 mg/mL, at least 0.02 mg/mL, at least 0.05 mg/mL, or at least 0.10 mg/mL.

In one embodiment, the solubility refers to aqueous solubility (i.e. an aqueous phase).

In one embodiment, the solubility refers to solubility in a water immiscible phase, such as an oil phase or an organic phase.

A building block is linked to a cucurbituril guest molecule or guest molecules by covalent bonds. The covalent bond may be a carbon-carbon bond, a carbon-nitrogen bond, a carbon-oxygen bond. The bond may be part of a linking group such as an ester or an amide, and/or part of a group comprising an alkylene or alkoxylene functionality.

Each guest molecule may be linked to the budding block using routine chemical linkage techniques. For example, guest molecules may be linked to the building block by: alkylation of a building block bearing an appropriate leaving group; esterification reactions; amidation reactions; ether forming reactions; olefin cross metathesis; or small guest molecule initiated reactions in which a polymer chain is grown off an initiating guest molecule.

In one embodiment, the average molecular weight of a build ng block, optionally together with any guest molecules, is at least 1,000, at least 5,000, at least 10,000, or at least 20,000.

In one embodiment, the average molecular weight of a building block, optionally together with any guest molecules, is at most 30,000, at most 50,000, at most 100,000, at most 200,000, at most 500,000, at most 1,000,000, or at most 2,000,000.

The average molecular weight may refer to the number average molecular weight or weight average molecular weight.

In one embodiment, the average molecular weight of a building block is in a range where the minimum and maximum amounts are selected from the embodiments above. For example, the average molecular weight is in the range 1,000 to 100,000.

In one embodiment, a building block is capable of providing a surface enhanced resonance effect. Typically, such capability is provided by a particle, and most particularly a metal-containing particle. Suitable particles are such as those described herein. Most suitable are those particles that are capable of providing a surface enhanced effect for surface enhanced Raman spectroscopy.

Described below are building blocks that are based on polymeric molecules and particles, including nanoparticles.

In one embodiment, where the network is obtainable from a composition comprising first and second building blocks, the first building block is a polymeric molecule and the second building block is a particle or a polymeric molecule. In one embodiment, where the network is obtainable from a composition comprising first and second building blocks, the first building block is a polymeric molecule and the second building block is a particle. In one embodiment, where the network is obtainable from a composition comprising a first, the first building block is a polymeric molecule.

Polymeric Molecule

In one embodiment, a building block is a polymeric molecule.

Polymeric compounds that are covalently linked to cucurbituril guest molecules are known from WO 2009/071899, which s incorporated by reference herein. Polymeric molecules comprise a plurality of repeating structural units (monomers) which are connected by covalent bonds. Polymeric molecules may comprise a single type of monomer (homopolymers), or more than one type of monomer (co-polymers). Polymeric molecules may be straight or branched. Where the polymeric molecule is a co-polymer, it may be a random, alternating, periodic, statistical, or block polymer, or a mixture thereof. The co-polymer may also be a graft polymer.

In one embodiment, the polymeric molecule has 2, 3, 4 or 5 repeat units. For convenience, such a polymer may be referred to as an oligomer.

In other embodiments, the polymeric molecule has at least 4, at least 8, at least 15, at least 100, or at least 1,000 monomer units. The number of units may be an average number of units.

In other embodiment, the polymeric molecule has an average number of monomer units in a range selected from 10-200, 50-200, 50-150 or 75-125.

The number of guest molecules per polymeric molecule building block is as set out above. Alternatively, the number of guest molecules may be expressed as the percentage of monomers present in the polymer that are attached to guest molecules as a total of all the monomers present in the polymeric molecule. This may be referred to as the functionality percentage.

In one embodiment, the functionality of a polymeric molecule is at least 1%, at least 2% or at least 5%.

In one embodiment, the functionality of a polymeric molecule is at most 50%, at most 40%, at most 20%, at most 15 or at most 10%.

In one embodiment, the functionality is in a range where the minimum and maximum amounts are selected from the embodiments above. For example, the functionality is in the range 5 to 40%.

The functionality percentage may be determined from proton NMR measurements of a polymer sample.

In one embodiment, the polymeric molecule has a molecular weight (Mw) of greater than 500, greater than 1000, greater than 2000, greater than 3000 or greater than 4000. The molecular weight may be the weight average molecular weight or the number average molecule weight. The number average and weight average molecular weights of a polymer may be determined by conventional techniques.

In one embodiment, the polymer is a synthetic polydisperse polymer. A polydisperse polymer comprises polymeric molecules having a range of molecular masses. The polydispersity index (PDI) (weight average molecular weight divided by the number average molecular weight) of a polydisperse polymer is greater than 1, and may be in the range 5 to 20. The polydispersity of a polymeric molecule may be determined by conventional techniques such as gel permeation or size exclusion chromatography.

Suitable for use in the present invention are polymeric molecules having a relatively low polydispersity. Such polymeric molecules may have a polydispersity in the range selected from 1 to 5, 1 to 3, or 1 to 2. Such polymers may be referred to as low- or monodisperse in view of their relatively low dispersity.

The use of low- or monodisperse polymeric molecules is particularly attractive, as the reactively of individual molecules is relatively uniform, and the products that result from their use may also be physically and chemically relatively uniform, and may be relatively low- or monodisperse. Methods for the preparation of low- or monodisperse polymers are well known in the art, and include polymerisation reactions based on radical initiated polymerisation, including RAFT (reversible addition-fragmentation chain transfer) polymerisition (see, for example, Chiefari et al. *Macromolecules* 1998, 31, 5559). An example synthesis of a polymer having a low dispersity is also provided herein.

Many polymeric molecules are known in the art and may be used to produce shell material as described herein. The choice of polymeric molecule will depend on the particular application of the capsule. Suitable polymeric molecules include natural polymers, such as proteins, oligopeptides, nucleic acids, glycosaminoglycans or polysaccharides (including cellulose and related forms such as guar, chitosan chitosan, agarose, and alginate and their functionalised derivatives), or synthetic polymers, such as polyethylene glycol (PEG), cis-1,4-polyisoprene (PI), poly(meth)acrylate, polystyrene, polyacrylamide, and polyvinyl alcohol. The polymer may be a homo or copolymer.

The polymeric molecule may comprise two or more natural and/or synthetic polymers. These polymers may be arranged in a linear architecture, cyclic architecture, comb or graft architecture, (hyper)branched architecture or star architecture.

Suitable polymeric molecules include those polymeric molecules having hydrophilic characteristics. Thus, a part of the polymer, which part may refer to, amongst others, a monomer unit, the backbone itself, a side chain or a grafted polymer, is hydrophilic. In one embodiment, the polymeric molecule is capable of forming hydrogen bonds in a polar solvent, such as water. The polymeric molecule is soluble in water to form a continuous phase.

In one embodiment, the polymeric molecule is amphiphilic.

Where two or more building blocks are provided, such as a first and a second building block, each building block may be independently selected from the polymeric molecules described above. In one embodiment, the first and second building blocks are different.

In one embodiment, the first and second building blocks are the same. In this latter case, the building blocks themselves differ only with respect to the guest molecules that are covalently attached to each.

In one embodiment, the polymeric molecule is or comprises a poly(meth)aryclate-, a polystyrene- and/or a poly (meth)arcylamide polymer.

In one embodiment, the polymer is or comprises a poly (meth)aryclate polymer, which may be or comprise a polyaryclate polymer The acrylate functionality of the (meth)aryclate may be the site for connecting desirable functionality, for example, for connecting a solubilising group or a detectable label.

In one embodiment, the polymeric molecule is obtained or obtainable from a polymerisable composition comprising:
(i) monomer, such as a (meth)aryclate or a styrene, which is attached to a cucurbituril guest molecule;
and optionally further comprising:
(ii) a monomer, such as a (meth)aryclate or a styrene, which is attached to a detectable label; and/or
(iii) a monomer, such as a (meth)aryclate or a styrene, which is attached to a solubilising group, such as an aqueous solubilising group.

In one embodiment, each monomer is a (meth)aryclate monomer.

In one embodiment, each monomer is a styrene monomer.

Where (i) is present with other components, such as (ii) or (iii), it is present in the polymerisable composition in at least 1, at least 5, at least 10 or at least 20 mole %.

Where (i) is present with other components, such as (ii) or (iii), it is present in the polymerisable composition in at most 90, at most 50, at most 40 or at least 30 mole %.

In one embodiment, the amount of (i) present is in a range where the minimum and maximum amounts are selected from the embodiments above. For example, the amount present in the range 10 to 50 mole %.

In one embodiment, (i) is present at a level sufficient to provide a polymeric molecule having a plurality of cucurbituril guest molecules linked to each single polymer molecule.

In one embodiment, (i) is present at a level sufficient to provide a polymeric molecule having a single cucurbituril guest molecules linked to each single polymer molecule.

In one embodiment, (i) is present at a level sufficient to provide a polymeric molecule having the functionality % described above.

Where (ii) is present, it is present in the polymerisable composition in at least 0.5, at least 1, or at least 2 mole %.

Where (ii) is present, it is present in the polymerisable composition in at most 20, at most 10, or at most 5 mole %.

In one embodiment, the amount of (ii) present is in a range where the minimum and maximum amounts are selected from the embodiments above. For example, the amount present in the range 1 to 5 mole %.

Where (iii) is present, it is present in the polymerisable composition in at least 0.5, at least 1, at least 2, at least 5, at least 10, at least 20, or at least 50 mole %

Where (iii) is present, it is present in the polymerisable composition in at most 90, at most 80, or at most 70 mole %.

In one embodiment, the amount of (iii) present is in a range where the minimum and maximum amounts are selected from the embodiments above. For example, the amount present in the range 10 to 80 mole %.

Where a reference is made to mole %, this is a reference to the amount of a component present with respect to the total amount, in moles, of (i), and (ii) and (iii), where present, and any other polymerisable monomers, where present. The component referred to may be one of (i), (ii), (iii), or any other polymerisable monomers.

In one embodiment, the composition further comprises one or more additional (meth)acrylate monomers. One monomer may be a (meth)acrylate monomer. One or more monomers may be a (meth)acrylate monomer which is substituted at the ester group.

Where a reference is made to mole %, this is a reference to the amount of a component present with respect to the total amount, in moles, of (i), and (ii) and (iii), where present, and any other polymerisable monomers, where present. The component referred to may be one of (i), (ii), (iii), or any other polymerisable monomers. The component referred to may be a chain transfer agent or a radical initiator, as described below.

The term attached refers to the connection of the acrylate (ester), group or the phenyl group of the styrene, either directly or indirectly to the group specified. Where there is an indirect connected it is understood that a linker group may form the connection between the acrylate and the group specified. In one embodiment, the linker may comprise a (poly)ethylene glycol (PEG) group.

In one embodiment, the detectable label is a fluorescent label. The fluorescent label may be a fluorescein or rhodamine label. The "colour" of the label is not particularly restricted, and green, red, yellow, cyan and orange labels are suitable for use.

In one embodiment, the aqueous solubilising group is a PEG group. The PEG group may have at least 2, 3, 4, 5 or 10 repeat ethylene glycol units. The PEG group may have at most 50, 40, 20, or 15 repeat ethylene glycol units.

In one embodiment, the aqueous solubilising group is or comprises amino, hydroxy, carboxy, or sulfonic acid.

In one embodiment, the amino group is a quaternary amino group, for example a trimethylamino group.

In one embodiment, the composition further comprises a chain transfer agent.

In one embodiment, the chain transfer agent is a thiocarbonylthio compound.

Where a chain transfer agent is present, it is present in the polymerisable composition in at least 0.1, at least 0.5, or at least 1 mole %.

Where a chain transfer agent is present, it is present in the polymerisable composition in at most 10, at most 5, or at most 2 mole %.

In one embodiment, the amount of a chain transfer agent present is in a range where the minimum and maximum amounts are selected from the embodiments above. For example, the amount present in the range 0.5 to 2 mole %.

In one embodiment, the composition further comprises a radical initiator.

Where a radical initiator is present, it is present in the polymerisable composition in at least 0.01, at least 0.05, at least 0.1 mole %.

Where a radical initiator is present, it is present in the polymerisable composition in at most 5, at most 2, at most 1, or at most 0.5 mole %.

In one embodiment, the amount of a radical initiator present is in a range where the minimum and maximum amounts are selected from the embodiments above. For example, the amount present in the range 0.1 to 0.5 mole %.

In one embodiment, the radical initiator is selected from the group consisting of AIBN (azobisisobutyronitrile), ACPA (4,4'-azobis(4-cyanopentanoic acid)) and ACVA (4,4'-Azobis(4-cyanovaleric acid).

In one embodiment, the polymeric molecule is obtained or obtainable from the polymerisation of a composition comprising (i) and optionally (ii) and/or (iii) using the change transfer agent and/or radical initiator described.

In one embodiment, the polymeric molecule is obtainable or obtained from a composition described herein using a radical polymerisation process. In one embodiment, the In one embodiment, the polymerisation reaction is performed at elevated temperature.

The reaction may be performed at a temperature of at least 30, at least 40 or at least 50° C. The reaction may be performed at a temperature of at most 100, at most 90 or at most 80° C.

In one embodiment, the polymerisation reaction is performed in an organic solvent. The original solvent may be an ether solvent, for example 1,4-dioxane, or an alkyl alcohol solvent, for example ethanol. The polymerisation reaction may be performed at reflux temperature.

The concentration of the polymerisable mixture in the organic solvent may be at most 5.0, at most 2.0, or at most 1.5 M.

The concentration of the polymerisable mixture in the organic solvent may be at least 0.05, at least 0.1, at least 0.5 M, or at least 1.0 M.

In one embodiment, the concentration is in a range where the minimum and maximum amounts are selected from the embodiments above. For example, the concentration is in the range 1.0 to 2.0 M.

In one embodiment, the polymerisation reaction is performed for at least 1, at least 5 or at least 10 hours.

In one embodiment, the polymerisation reaction is performed for at most 72, or at most 48 hours.

The polymerisation reaction may be stopped using techniques familiar to those in the art. Steps may include reaction mixture dilution and/or temperature reduction.

In one embodiment, the polymerisation reaction is performed for a time sufficient to obtain a polymeric molecule having a molecular weight as described herein.

In one embodiment, the polymerisation reaction is performed for a time sufficient to obtain a polymeric molecule having a plurality of guest molecules.

In one embodiment, the polymerisation reaction is performed for a time sufficient to obtain a polymeric molecule having one guest molecule.

The concentration of the polymerisable mixture refers to the total amount of monomer present (which includes (i), and (ii) and (iii), where present, and any other polymerisable monomers, where present) in moles, in unit volume of organic solvent (i.e. per litre).

In one embodiment, the polymer may be formed as a particle.

Particle

In one embodiment, the building block is a particle. The type of particle for use in the present invention is not particularly limited.

In one embodiment, the particle is a first building block and the particle is linked to a plurality of cucurbituril guest molecules.

In one embodiment, the particle is a second building block and the particle is linked to one or more cucurbituril guest molecules.

In one embodiment, the particle is a second building block and the particle is linked to a plurality of cucurbituril guest molecules.

Typically, the particle has a size that is one, two, three or four magnitudes smaller than the size of the capsule.

In one embodiment, the particle is a nanoparticle. A nanoparticle has an average size of at least 1, at least 5, or at least 10 nm in diameter. A nanoparticle has an average size of at most 900, at most 500, at most 200, or at most 100 nm in diameter.

In one embodiment, the nanoparticle has an average size in the range 1-100 nm or 5-60 nm in diameter.

The average refers to the numerical average. The diameter of a particle may be measured using microscopic techniques, including TEM.

In one embodiment, the particles have a relative standard deviation (RSD) of at most 0.5%, at most 1%, at most 1.5%, at most 2%, at most 4%, at most 5%, at most 7%, at most 10%, at moist 15%, at most 20% or at most 25%.

In one embodiment, the particle has a hydrodynamic diameter of at least 1, at least 5, or at least 10 nM in diameter.

In one embodiment, the particle has a hydrodynamic diameter of at most 900, at most 500, at most 200, or at most 100 nM in diameter.

The hydrodynamic diameter may refer to the number average or volume average. The hydrodynamic diameter may be determined from dynamic light scattering (DLS) measurements of a particle sample.

In one embodiment, the particle is a metal particle.

In one embodiment, the particle is a transition metal particle.

In one embodiment, the particle is a noble metal particle.

In one embodiment, the particle is or comprises copper, ruthenium, palladium, platinum, titanium, zinc oxide, gold or silver, or mixtures thereof.

In one embodiment, the particle is or comprises gold, silver particle, or a mixture thereof.

In one embodiment, the particle is a gold or a silver particle, or a mixture thereof.

In one embodiment, the particle is a gold nanoparticle (AuNP).

In one embodiment, the particle is or comprises silica or calcium carbonate.

In one embodiment, the particle is a quantum dot.

In one embodiment, the particle is or comprises a polymer. The polymer may be a polystyrene or polyacrylamide polymer. The polymer may be a biological polymer including for example a polypeptide or a polynucleotide.

In one embodiment, the particle comprises a material suitable for use in surface enhanced Raman spectroscopy (SERS). Particles of gold and/or silver and/or other transition metals are suitable for such use.

Gold and silver particles may be prepared using techniques known in the art. Examples of preparations include those described by Coulston et al. (*Chem. Commun.* 2011, 47, 164) Martin et al. (Martin et al. *Langmuir* 2010, 26, 7410) and Frens (Frens *Nature Phys. Sci.* 1973, 241, 20), which are incorporated herein by reference in their entirety.

The particle is linked to one or more guest molecules, as appropriate. Typically, where the particle is a first building block, it is provided at least with a plurality of guest molecules. Where, the particle is a second building block, it is provided at one or more guest molecules.

In one embodiment, a guest molecule may be covalently linked to a particle via a linking group. The linking group may be a spacer element to provide distance between the guest molecule and the particle bulk. The linker may include functionality for enhancing the water solubility of the combined building block and guest molecule construct. The linker is provided with functionality to allow connection to the particle surface. For example, where the particle is a gold particle, the linker has thiol functionality for the formation of a connecting gold-sulfur bond.

Alternatively, a guest molecule may be attached directly to the particle surface, through suitable functionality. For example, where the particle is a gold particle, the guest molecule may be attached to the gold surface via a thiol functionality of the guest molecule.

In one embodiment, the particle comprises solubilising groups such that the particle, together with its guest molecules, is soluble in water or is soluble in a water immiscible phase.

The solubilising groups are attached to the surface of the particle. The solubilising group may be covalently attached to the particle through suitable functionality. Where the particle is a gold particle, the solubilising group is attached through a sulfur bond to the gold surface.

The solubilising group may be, or comprise, polyethylene glycol or amine, hydroxy, carboxy or thiol functionality.

In one embodiment, the building block is obtained or obtainable from a composition comprising:

(i) a gold particle;

(ii) a guest molecule together with a linking group that has thiol functionality; and (iii) a solubilising molecule having thiol functionality; and optionally further comprising (iv) a further guest molecule, together with a linking group that has thiol functionality.

In one embodiment, the amount of guest molecule present in the composition is at least 1, at least 5, at least 10 or at least 15 mole %.

In one embodiment, the amount of guest molecule present in the composition is at most 80, at most 50, or at most 25 mole %.

A reference to mole % is a reference to the amount of guest molecule present as a percentage of the total amount of (ii) and (iii), and (iv) where present, in the composition.

The amount of (ii) present in the composition may be such to allow the preparation of a particle building block having a plurality of guest molecules.

Cucurbituril Guest

As noted above, the guest is a compound that is capable of forming a guest-host complex with a cucurbituril. The term complexation therefore refers to the establishment of the guest-host complex.

In some embodiments of the invention, the guest host complex is a ternary complex comprising the cucurbituril host and a first guest molecule and a second molecule. Typically such complexes are based around CB[8] and variants and derivatives thereof.

In some embodiments of the invention, the guest host complex is a binary complex comprising the cucurbituril host and a first guest molecule. Typically such complexes are based around CB[5] or CB[7], and variants and derivatives thereof. In the present invention, binary complexes are obtainable from a plurality of covalently linked cucurbituils. CB[8], and variants and derivatives thereof, may also form binary complexes.

In principal, any compound having a suitable binding affinity may be used in the methods of the present invention. The compound used may be selected based on the size of the moieties that are thought to interact with the cavity of the cucurbituril. The size of these moieties may be sufficiently large to permit complexation only with larger cucurbituril forms.

The term selective may be used to refer to the amount of guest-host complex formed. where the cucurbituril (the first cucurbituril) and a second cucurbituril are present in a mixture with a particular guest molecule or guest molecules. The guest-host complex formed between the first cucurbituril and the guest (in a binary complex) or guests (in a ternary complex) may be at least 60 mol %, at least 70 mol %, at least 80 mol %, at least 90 mol %, at least 95 mol %, at least 97 mol %, at least 98 mol %, or at least 99 mol %, of the total amount of guest-host complex formed (for, example taking into account the amount of guest-host complex formed between the second cucurbituril and the guest or guests, if any).

In one embodiment, the guest-host complex formed from the (first) cucurbituril and the guest or guests has a binding affinity that is at least 100 times greater than the binding affinity of a guest host complex formed from the second cucurbituril and the guest or guests. Preferably, the binding affinity is at least $10^3$, at least $10^4$, at least $10^5$, at least $10^6$, or at least $10^7$ greater.

Cucurbituril guest molecules are well known in the art. Examples of guest compounds for use include those described in WO 2009/071899, Jiao et al. (Jiao et al. *Org. Lett.* 2011, 13, 3044), Jiao et al. (Jiao et al. *J. Am. Chem. Soc.* 2010, 132, 15734) and Rauwald et al. (Rauwald et al. *J. Phys. Chem.* 2010, 114, 8606).

Described below are guest molecules that are suitable for use in the formation of a capsule shell. Such guest molecules may be connected to a building block using standard synthetic techniques.

A cucurbituril guest molecule may be derived from, or contain, a structure from the table below:

| Guest Molecules |
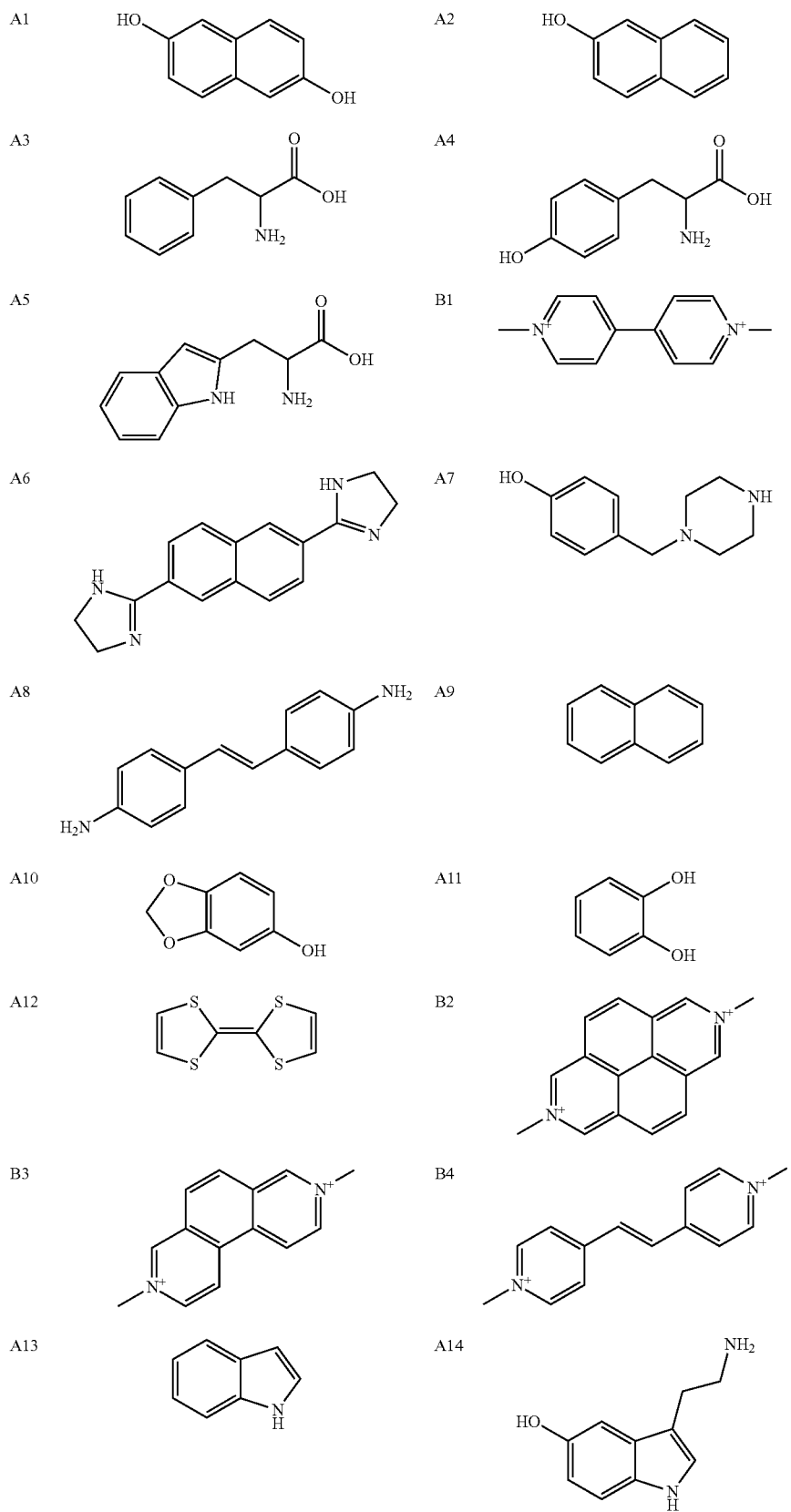

-continued
| Guest Molecules | |
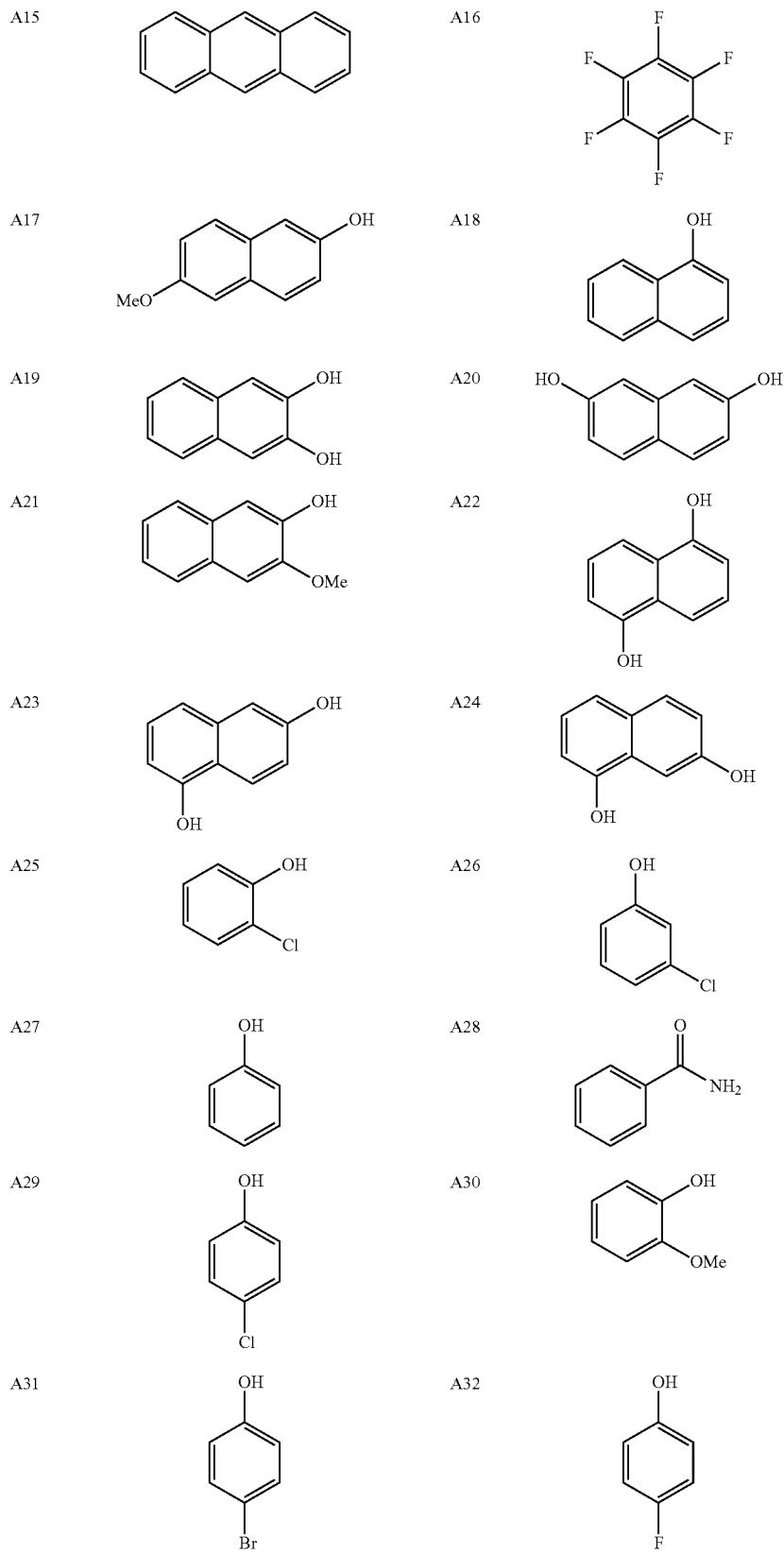

| | Guest Molecules | | |
|---|---|---|---|
| A33 | 4-iodophenol | A34 | 3-methoxyphenol |
| A35 | 3-hydroxybenzonitrile | A36 | resorcinol (1,3-dihydroxybenzene) |
| A37 | 2-hydroxybenzonitrile | A38 | 4-methoxyphenol |
| A39 | 1,4-dimethoxybenzene | A40 | hydroquinone (1,4-dihydroxybenzene) |
| A41 | phloroglucinol (1,3,5-trihydroxybenzene) | A42 | 4-hydroxybenzonitrile |
| A43 | 1H-benzotriazole | A44 | azobenzene |
| A45 | 2-naphthalenethiol | A46 | 1-adamantylamine | where the structure may be a salt, including protonated forms, where appropriate. In one embodiment, the guest molecules are guest molecules for CB[8].

In one embodiment, the guest molecule is, or is derived from, or contains, structure A1-A43, A46 or B1-B4, in the table above.

In one embodiment, the guest molecule is, or is derived from, or contains, structure A1, A2, or A13 in the table above.

In one embodiment, the guest molecule is, or is derived from, or contains, structure B1.

Additionally, the guest molecule is or is derived from, or contains, adamantane, ferrocene or cyclooctane (including bicyclo[2.2.2]octane). Such are described by Moghaddam et al. (see *J. Am. Chem. Soc.* 2011, 133, 3570).

In some embodiments, first and second guest molecules form a pair which may interact within the cavity of cucurbituril to form a stable ternary host-guest complex. Any guest pair that fits within the cavity of the cucurbituril may be employed. In some embodiments, the pair of guest molecules may form a charge transfer pair comprising an electron-rich and an electron-deficient compound. One of the first and second guest molecules acts as an electron acceptor and the other as an electron donor in the CT pair. For example, the first guest molecule may be an electron deficient molecule which acts an electron acceptor and the second guest molecule may be an electron rich molecule which acts as an electron donor or vice versa. In one embodiment, the cucurbituril is CB[8].

Suitable electron acceptors include 4,4'-bipyridinium derivatives, for example N,N'-dimethyldipyridyliumylethylene, and other related acceptors, such as those based on diazapyrenes and diazaphenanthrenes. Viologen compounds including alkyl viologens are particularly suitable for use in the present invention. Examples of alkyl viologen compounds include N,N'-dimethyl-4,4'-bipyridinium salts (also known as Paraquat). Suitable electron donors include electron-rich aromatic molecules, for example 1,2-dihydroxybenzene, 1,3-dihydroxybenzene, 1,4-dihydroxybenzene, tetrathiafulvalene, naphthalenes such as 2,6-dihydroxynaphthalene and 2-naphthol, indoles and sesamol (3,4-methylenedioxyphenol). Polycyclic aromatic compounds in general may find use as suitable electron donors in the present invention. Examples of such compounds include anthracene and naphthacene.

Amino acids, such as tryptophan, tyrosine and phenylalanine may be suitable for use as electron donors. Peptide sequences comprising these amino acids at their terminus may be used. For example, a donor comprising an amino acid sequence N-WGG-C, N-GGW-C or N-GWG-C may be used.

In some embodiments, the guest molecules are a pair of compounds, for example first and second guest molecules, where one of the pair is an A compound as set out in the table above (e.g. A1, A2, A3 etc.), and the other of the pair is a B compound as set out in the table above (e.g. B1, B2, B3 etc.). In one embodiment, the A compound is selected from A1-A43 and A46. In one embodiment, the B compound is B1.

Other suitable guest molecules include peptides such as WGG (Bush, M. E. et al *J. Am. Chem. Soc.* 2005, 127, 14511-14517).

An electron-rich guest molecule may be paired up with any electron-deficient CB[8] guest molecule. Examples of suitable pairs of guest molecules for example first and second guest molecules, for use as described herein may include:
viologen and naphthol;
viologen and dihydroxybenzene;
viologen and tetrathiafulvalene;
viologen and indole;
methylviologen and naphthol;
methylviologen and dihydroxybenzene;
methylviologen and tetrathiafulvalene;
methylviologen and indole;
N,N'-dimethyldipyridyliumylethylene and naphthol;
N,N'-dimethyldipyridyliumylethylene and dihydroxybenzene;
N,N'-dimethyldipyridyliumylethylene and tetrathiafulvalene;
N,N'-dimethyldipyridyliumylethylene and indole;
2,7-dimethyldiazapyrenium and naphthol;
2,7-dimethyldiazapyrenium and dihydroxybenzene;
2,7-dimethyldiazapyrenium and tetrathiafulvalene; and
2,7-dimethyldiazapyrenium and indole.

In particular, suitable pairs of guest molecules for use as described herein may include 2-naphthol and methyl viologen, 2,6-dihydroxynaphthalene and methyl viologen and tetrathiafulvalene and methyl viologen.

In one embodiment, the guest pair is 2-naphthol and methyl viologen.

In one embodiment, the guest pair is a reference to a pair of guest molecules suitable for forming a ternary complex with CB[8].

In one embodiment, the guest molecule is preferably an ionic liquid. Typically, such guests are suitable for forming a complex with CB[7]. However, they may also form complexes with CB[8] in either a binary complex, or in a ternary complex together with another small guest molecule or solvent (see Jiao et al. *Org. Lett.* 2011, 13, 3044).

The ionic liquid typically comprises a cationic organic nitrogen heterocycle, which may be an aromatic nitrogen heterocycle (a heteroaryl) or a non aromatic nitrogen heterocycle. The ionic liquid also typically comprises a counter-anion to the cationic organic nitrogen heterocycle. The nitrogen heteroaryl group is preferably a nitrogen $C_{5-10}$heteroaryl group, most preferably a nitrogen $C_{5-6}$heteroaryl group, where the subscript refers to the total number of atoms in the ring or rings, including carbon and nitrogen atoms. The non aromatic nitrogen heterocycle is preferably a nitrogen $C_{5-6}$heterocycle, where the subscript refers to the total number of atoms in the ring or rings, including carbon and nitrogen atoms. A nitrogen atom in the ring of the nitrogen heterocycle is quaternised.

The counter-anion may be a halide, preferably a bromide. Other counter-anions suitable for use are those that result in a complex that is soluble in water.

The guest is preferably a compound, including a salt, comprising one of the following groups selected from the list consisting of: imidazolium moiety; pyridinium moiety; quinolinium moiety; pyrimidinium moiety; pyrrolium moiety; and quaternary pyrrolidine moiety.

Preferably, the guest comprises an imidazolium moiety. An especially preferred guest is 1-alkyl-3-alkylimidazolium, where the alkyl groups are optionally substituted.

1-Alkyl-3-alkylimidazolium compounds, where the alkyl groups are unsubstituted, are especially suitable for forming a complex with CB[7].

1-Alkyl-3-alkylimidazolium compounds, where the alkyl groups are unsubstituted, are especially suitable for forming a complex with CB[6]

1-Alkyl-3-alkylimidazolium compounds, where an alkyl group is substituted with aryl (preferably napthyl), are especially suitable for forming a complex with CB[8].

The 1-alkyl and 3-alkyl substituents may the same or different. Preferably, they are different.

In one embodiment, the 3-alkyl substituent is methyl, and is preferably unsubstituted.

In one embodiment, the 1-alkyl substituent is ethyl or butyl, and each is preferably unsubstituted.

In one embodiment, the optional substituent is aryl, preferably $C_{5-10}$aryl. Aryl includes carboaryl and heteroaryl. Aryl groups include phenyl, napthyl and quinolinyl.

In one embodiment, the alkyl groups described herein are linear alkyl groups.

Each alkyl group is independently a $C_{1-6}$alkyl group, preferably a $C_{1-4}$alkyl group.

The aryl substituent may itself be another 1-alkyl-3-substituted-imidazolium moiety (where the alkyl group is attached to the 3-position of the ring).

In another embodiment, the compound preferably comprises a pyridinium moiety.

The ionic liquid molecules describe above are particular useful for forming binary guest-host complexes. Complexes comprising two ionic liquid molecules as guests within a cucurbituril host are also encompassed by the present invention.

A cucurbituril may be capable of forming both binary and ternary complexes. For example, it has been previously noted that CB[6] compounds form ternary complexes with short chain 1-alkyl-3-methylimidazolium guest molecules, whilst longer chain 1-alkyl-3-methylimidazolium guest molecules form binary complexes with the cucurbituril host.

Preferred guests for use in the present invention are of the form H⁺X⁻, where H⁺ is one of the following cations,

| Cation | Structure |
|---|---|
| A | 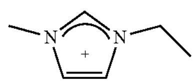 |
| B | 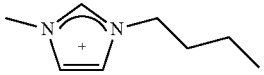 |
| C | 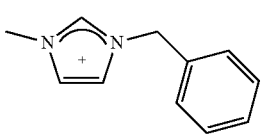 |
| D | 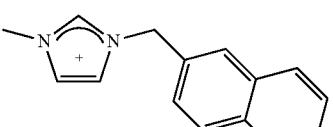 |
| E | 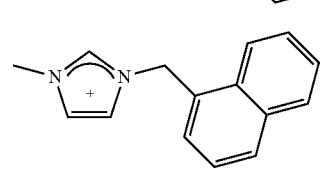 |
| F | 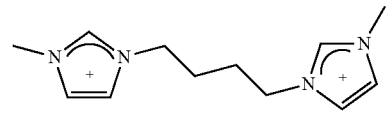 |
| G | 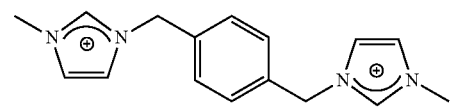 |
| H | 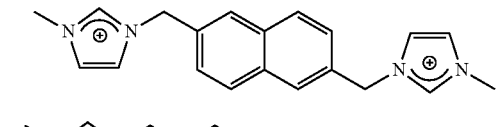 |
| I | 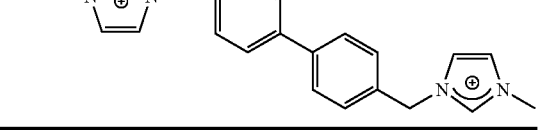 | and X⁻ is a suitable counter-anion, as defined above. A preferred counter anion is a halide anion, preferably Br⁻.

In a preferred embodiment, cation A or cation B may be used to form a complex with CB[7] or CB[6].

In a preferred embodiment, cation D or cation E may be used to form a complex with CB[8].

Cations A and B may be referred to as 1-ethyl-3-methylimidazolium and 1-butyl-3-methylimidazolium respectively.

Cations D and E may be referred to as 1-naphthalenylmethyl-3-methylimidazolium, where D is 1-naphthalen-2-ylmethyl-3-methylimidazolium and E is 1-naphthalen-1-ylmethyl-3-methylimidazolium.

Alternatively or additionally, the guest compounds may be an imidazolium salt of formula (I):

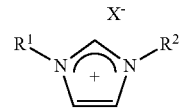

wherein X⁻ is a counter anion;

R¹ is independently selected from H and saturated $C_{1-6}$alkyl;

R² is independently $C_1$ alkyl which may optionally contain one or more double or triple bonds, and may be optionally interrupted by a heteroatom selected from —O—, —S—, —NH—, and —B—, and may be optionally substituted.

In one embodiment, X⁻ is independently selected from the group consisting of Cl⁻, Br⁻, I⁻, $BF_4^-$, $PF_6^-$, OH⁻, SH⁻, $HSO_4^-$, $HCO_3^-$, $NTf_2$, $C_2N_5O_4$, $AlCl_4^-$, $Fe_3Cl_{12}$, $NO_3^-$, $NMeS_2^-$, $MeSO_3^-$, $SbF_6^-$, $PrCB_{11}H_{11}^-$, $AuCl_4^-$, $HF_2^-$, $NO_2^-$, $Ag(CN)_2^-$, and $NiCl_4^-$. In one embodiment, X⁻ is selected from Cl⁻, Br⁻, and I⁻.

In one embodiment, R¹ is selected from H and linear saturated $C_{1-6}$alkyl.

In one embodiment, R² is linear $C_{1-10}$ alkyl, which may optionally contain one or more double bonds, and may be optionally interrupted by a heteroatom selected from —O—, —S—, —NH—, and —B—, and may be optionally substituted.

In one embodiment, R² is linear $C_{1-10}$ alkyl, which may optionally contain one or more double bonds, and may be optionally substituted.

In one embodiment, where a double or triple bond is present, it may be conjugated to the imidazolium moiety. Alternatively, the double or triple bond may not be conjugated to the imidazolium moiety.

In one embodiment, the optional substituents are independently selected from the group consisting of halo, optionally substituted $C_{5-20}$ aryl, —OR³, —OCOR³, =O, —SR³, =S, —BR³, —NR³R⁴, —NR³COR³, —N(R³)CONR³R⁴, —COOR³, —C(O)R³, —C(=O)SR³, —CONR³R⁴, —C(S)R³, —C(=S)SR³, and —C(=S)NR³R⁴, where each of R³ and R⁴ is independently selected from H and optionally substituted saturated $C_{1-6}$ alkyl, $C_{5-20}$ aryl and $C_{1-6}$ alkylene-$C_{5-20}$ aryl.

or R³ and R⁴ may together may form an optionally saturated 5-, 6- or 7-membered heterocyclic ring which is optionally substituted with a group —R³.

In one embodiment, the optional substituents are independently selected from the group consisting of halo, optionally substituted $C_{5-20}$ aryl, —OR³, —OCOR³, —NR³R⁴, —NR³COR³, —N(R³)CONR³R⁴, —COOR³, —C(O)R³, and —CONR³R⁴, where R³ and R⁴ are defined as above.

Each $C_{5-20}$ aryl group may be independently selected from a $C_{6-20}$ carboaryl group or a $C_{5-20}$ heteroaryl group.

Examples of $C_{6-20}$ carboaryl groups include phenyl and napthyl.

Examples of $C_{5-20}$ heteroaryl groups include pyrrole (azole) ($C_5$), pyridine (azine) ($C_6$), furan (oxole) ($C_5$), thiophene (thiole) ($C_5$), oxazole ($C_5$), thiazole ($C_5$), imidazole (1,3-diazole) ($C_5$), pyrazole (1,2-diazole) ($C_5$), pyridazine (1,2-diazine) ($C_5$), and pyrimidine (1,3-diazine) ($C_6$) (e.g., cytosine, thymine, uracil).

Each $C_{5-20}$ aryl is preferably selected from optionally substituted phenyl, napthyl and imidazolium.

Each $C_{5-20}$ aryl group is optionally substituted. The optional substituents are independently selected from halo, $C_{1-6}$ alkyl, —$OR^3$, —$OCOR^3$, —$NR^3R^4$, —$NR^3COR^3$, —$N(R^3)CONR^3R^4$, —$COOR^3$, —$C(O)R^3$, and —$CONR^3R^4$, where $R^3$ and $R^4$ are defined as above.

In one embodiment, each $C_{5-20}$ aryl group is optionally substituted with $C_{1-6}$ alkyl.

Where the $C_{5-20}$ aryl group is an imidazolium, such is preferably substituted at nitrogen with a group $R^1$ (thereby forming a quaternary nitrogen).

The compound of formula (I) comprises an imidazolium moiety having a substituent $R^2$ at the 1-position and a substituent $R^1$ at the 3-position. In a further aspect of the invention, the compound of formula (I) may be optionally further substituted at the 2-, 4- or 5-position with a group $R^4$, wherein $R^4$ has the same meaning as $R^1$.

The embodiments above are combinable in any combination, as appropriate.

Encapsulant

The capsule of the invention may be used to encapsulate a component (the encapsulant). In one embodiment there is provided a capsule comprising an encapsulant. The capsule is suitable for storing a component, and this component may be later released as required at a chosen location.

It is understood that a reference to an encapsulated component is not a reference to a solvent molecule. For example, the encapsulated component is not water or is not an oil or an organic solvent. It is also understood that a reference to an encapsulated component is not a reference to a cucurbituril or a building block for use in the preparation of the capsule shell. Otherwise, the component is not particularly limited.

The encapsulant is therefore a component of the capsule that is provided in addition to solvent that may be present within the shell.

In the methods of the invention the capsule shell is prepared from a composition comprising a cucurbituril and one or more building blocks, as appropriate. Not all the cucurbituril and one or more building blocks may react to form shell material. Additionally, the cucurbituril and one or more building blocks may react to form a network, but this network may be not be included in the shell that forms the capsule. These unreacted or partially reacted reagents and products may be contained within the shell, and may be contained in addition to the encapsulant. Thus, the encapsulant is a component of the capsule that is provided in addition to unreacted or partially reacted reagents and products that may be present within the shell.

In one embodiment, the encapsulant compound has a solubility of at least 0.01 mg/mL, at least 0.02 mg/mL, at least 0.05 mg/mL, or at least 0.10 mg/mL.

In one embodiment, the solubility refers to aqueous solubility (i.e. an aqueous phase).

In one embodiment, the solubility refers to solubility in an oil phase or an organic phase.

The capsules of the invention may be used to encapsulate a wide range of components.

In one embodiment, the encapsulated component has a molecular weight of at least 100, at least 200, at least 300, at least 1,000, at least 5,000 (1 k), at least 10,000 (10 k), at least 50,000 (50 k), at least 100,000 (100 k) or at least 200,000 (200 k).

In one embodiment, the encapsulant is a therapeutic compound.

In one embodiment, the encapsulant is a biological molecule, such as a polynucleotide (for example DNA and RNA), a polypeptide or a polysaccharide.

In one embodiment, the encapsulant is a polymeric molecule, including biological polymers such as those polymers mentioned above.

In one embodiment, the encapsulant is a cell.

In one embodiment, the encapsulant is an ink.

In one embodiment, the encapsulant is a carbon nanotube.

In one embodiment, the encapsulant is a particle. The particle may be a metal particle.

The size of the capsule is selected so as to accommodate the size of the encapsulant.

Thus, the internal diameter (the distance from innermost wall to innermost wall) is greater than the greatest dimension of the encapsulant.

In one embodiment, the encapsulant has a detectable label. The detectable label may be used to quantify and/or locate the encapsulant. The label may be used to determine the amount of encapsulant contained with the capsule.

In one embodiment, the detectable label is a luminescent label. In one embodiment, the detectable label is a fluorescent label or a phosphorescent label.

In one embodiment, the detectable label is a visible.

In one embodiment, the fluorescent label is a rhodamine or fluorescein label.

In one embodiment, the capsule of the invention is for use as a reactor. The method of preparing the capsule as described herein brings together the reagents, which are supplied in separate second phase sub-flows, and are contacted at substantially the same time as the second phases contact the first phase. A shell of material is formed at the interface of the discrete regions that is formed, and this shell contains the reagents which may be permitted to react. The localisation of reagents within a discrete region is allows control over reaction timings.

Where the capsule is for use as a microreactor it is understood that the composition of the shell inner space will change over time as the reagents react to form a product, along with associated by-products, if any. As will be apparent, the amount of reagent will decrease as the reaction progresses.

Additional and Alternative Encapsulants

In addition to, or as alternatives to, the encapsulants mentioned above, the encapsulant may be selected from one or more of the encapsulants discussed below. In one embodiment, the molecular weight preferences given above apply to these encapsulants.

In one embodiment, the encapsulant is selected from the group consisting of toxic molecules (such as nerve agents and heavy metals), hormones, herbicides, pesticides, antibodies, pathogens (such as viruses), adjuvants, gels, nanoparticles (including metal or non-metal particles), polymers (including synthetic and natural polymers), catalysts (organic, inorganic, and organometallic), adhesives and sealants.

A pathogen is an agent that is capable of causing disease in a host. The pathogen may be a virus, a bacterium, a fungus, or a prion.

In one embodiment, the encapsulant is a virus.

The virus may be virus selected from a family selected from the group consisting of adenoviridae (e.g. adenovirus), herpesviridae (e.g. Herpes simplex, type 1 and type 2, and Epstein-barr), papillomaviridae (e.g. human papillomavirus), hepadnaviridae (e.g. Hepatitis B), flaviviridae (e.g. Hepatitis C, yellow fever, dengue, West Nile), retroviridae (e.g. immunodeficiency virus (HIV)), orthomyxoviridae (e.g. Influenza), paramyxoviridae (e.g. measles, mumps), rhabdoviridae (e.g. rabies), and reoviridae (e.g. rotavirus).

In one embodiment, the encapsulant is a microorganism

As noted above, in one embodiment, the encapsulant is a cell. The cell may be a prokaryotic or a eukaryotic cell.

The cell may be a mammal cell, such as a human cell, a rodent cell (e.g., a guinea pig, a hamster, a rat, a mouse) a lagomorph cell (e.g., a rabbit), an avian cell (e.g., a bird), a canine cell (e.g., a dog), a feline cell (e.g., a cat), an equine cell (e.g., a horse), a porcine cell (e.g., a pig), an ovine cell (e.g., a sheep), a bovine cell (e.g., a cow), a simian cell (e.g., a monkey or ape), a monkey cell (e.g., marmoset, baboon), an ape cell (e.g., gorilla, chimpanzee, orangutang, gibbon), or an ornithorhynchidae cell (e.g. platypus).

The cell may be a tumour cell, which may be a benign or malignant tumour cell.

Examples of eukaryotic cells include epithelial, endothelial, neural, skeletal, and fibroblast cells, amongst others.

In one embodiment, the encapsulant is a bacterium, such as a gram positive bacterium and a gram negative bacterium.

Examples of gram positive bacteria include *Corynebacterium, Mycobacterium, Nocardia, Streptomyces, Staphylococcus* (such as *S. aureus*), *Streptococcus* (such as *S. pneumoniae*), *Enterococcus* (such as *E. faecium*), *Bacillus, Clostridium* (such as *C. diff.*) and *Listeria*.

Examples of gram negative bacteria include *Hemophilus, Klebsiella, Legionella, Pseudomonas, Escherichia* (such as *E. coli*), *Proteus, Enterobacter, Serratia, Helicobacter* (such as *Helicobacter pylori*), and *Salmonella*.

In one embodiment, the encapsulant is an antibody.

The term "antibody" herein is used in the broadest sense and specifically covers monoclonal antibodies, polyclonal antibodies, dimers, multimers, multispecific antibodies (e.g., bispecific antibodies), and antibody fragments, so long as they exhibit the desired biological activity. Antibodies may be murine, human, humanized, chimeric, or derived from other species. An antibody is a protein generated by the immune system that is capable of recognizing and binding to a specific antigen. A target antigen generally has numerous binding sites, also called epitopes, recognized by CDRs on multiple antibodies. Each antibody that specifically binds to a different epitope has a different structure. Thus, one antigen may have more than one corresponding antibody. An antibody includes a full-length immunoglobulin molecule or an immunologically active portion of a full-length immunoglobulin molecule, i.e., a molecule that contains an antigen binding site that immunospecifically binds an antigen of a target of interest or part thereof, such targets including but not limited to, cancer cell or cells that produce autoimmune antibodies associated with an autoimmune disease. The immunoglobulin can be of any type (e.g. IgG, IgE, IgM, IgD, and IgA), class (e.g. IgG1, IgG2, IgG3, IgG4, IgA1 and IgA2) or subclass of immunoglobulin molecule. The immunoglobulins can be derived from any species, including human, murine, or rabbit origin.

"Antibody fragments" comprise a portion of a full length antibody, generally the antigen binding or variable region thereof. Examples of antibody fragments include Fab, Fab', F(ab')2, and Fv fragments; diabodies; linear antibodies; fragments produced by a Fab expression library, anti-idiotypic (anti-Id) antibodies, CDR (complementary determining region), and epitope-binding fragments of any of the above which immunospecifically bind to cancer cell antigens, viral antigens or microbial antigens, single-chain antibody molecules; and multispecific antibodies formed from antibody fragments.

The term "monoclonal antibody" as used herein refers to an antibody obtained from a population of substantially homogeneous antibodies, i.e. the individual antibodies comprising the population are identical except for possible naturally occurring mutations that may be present in minor amounts. Monoclonal antibodies are highly specific, being directed against a single antigenic site. Furthermore, in contrast to polyclonal antibody preparations which include different antibodies directed against different determinants (epitopes), each monoclonal antibody is directed against a single determinant on the antigen. In addition to their specificity, the monoclonal antibodies are advantageous in that they may be synthesized uncontaminated by other antibodies. The modifier "monoclonal" indicates the character of the antibody as being obtained from a substantially homogeneous population of antibodies, and is not to be construed as requiring production of the antibody by any particular method. For example, the monoclonal antibodies to be used in accordance with the present invention may be made by the hybridoma method, or may be made by recombinant DNA methods. The monoclonal antibodies may also be isolated from phage antibody libraries.

The monoclonal antibodies herein specifically include "chimeric" antibodies in which a portion of the heavy and/or light chain is identical with or homologous to corresponding sequences in antibodies derived from a particular species or belonging to a particular antibody class or subclass, while the remainder of the chain(s) is identical with or homologous to corresponding sequences in antibodies derived from another species or belonging to another antibody class or subclass, as well as fragments of such antibodies, so long as they exhibit the desired biological activity In one embodiment, the antibody is an antibody-drug conjugate (ADC).

The antibody may be suitably labelled for detection and analysis, either whilst held in the capsule, of for later use, when the antibody is released.

In one embodiment, the encapsulant is a hormone. The hormone may a peptidic hormone, such as insulin or growth hormone, or a lipid hormone, such as a steroid hormone, for example prostaglandin and estrogen.

In one embodiment, the encapsulant is a polypeptide. In one embodiment, the polypeptide is a protein. In one embodiment the protein has catalytic activity, for example having ligase, isomerase, lyase, hydrolase, transferase or oxidoreductase activity.

In one embodiment, the encapsulant is a polymer. In some embodiments, the capsule shell of the present invention includes a building block that is a functionalised polymer. Where such a building block is present, a polymer that is an encapsulant differs from the building block. In one embodiment, the encapsulant polymer is not suitable for forming a non-covalent link with a cucurbituril.

In one embodiment, the encapsulant is a metal particle.

In one embodiment, the nanoparticle is or comprises a noble metal.

In one embodiment, the nanoparticle is or comprises a transition metal.

In some embodiments, the capsule shell of the present invention includes a building block that is a functionalised particle. Where such a building block is present, a particle that is an encapsulant differs from the building block. In one embodiment, the encapsulant particle is not suitable for forming a non-covalent link with a cucurbituril.

In one embodiment, the nanoparticle is a gold nanoparticle (AuNP) or a silver nanoparticle (AgNP), or a nanoparticle comprising both silver and gold.

Generally, the particle is substantially spherical. However, particles having other shapes may be used, if appropriate or desirable.

In one embodiment, the nanoparticle has a diameter of at most 500 nm, at most 200 nm, at most 150 nm, at most 100 nm, at most 80 nm, or at most 70 nm.

In one embodiment, the nanoparticle has a diameter of at least 1 nm, at least 2 nm, at least 5 nm, at least 10 nm, at least 15 nm, at least 20 nm, at least 30 nm, or at least 40 nm.

In one embodiment, the diameter of the particle is in a range where the minimum and maximum rates are selected from the embodiments above. For example, the diameter is in the range 1 to 100 nm, or for example in the range 10 to 100 nm. For example, the diameter is in the range 2 to 500 nm In one embodiment, the nanoparticle has a diameter of about 20 nm.

The average refers to the numerical average. The diameter of a particle may be measured using microscopic techniques, including TEM.

The particles used in the present invention are sustainably monodisperse or have a very low dispersity. In one embodiment, the particles have a relative standard deviation (RSD) of at most 0.5%, at most 1%, at most 1.5%, at most 2%, at most 4%, at most 5%, at most 7%, at most 10%, at moist 15%, at most 20% or at most 25%.

In one embodiment, the particle has a hydrodynamic diameter of at least 5 nm, at least 10 nm, at least 15 nm, at least 20 nm, at least 30 nm, at least 40 nm.

In one embodiment, the particle has a hydrodynamic diameter of at most 500 nm, at most 200 nm, at most 150 nm, at most 100 nm, at most 80 nm, or at most 70 nm.

The hydrodynamic diameter may refer to the number average or volume average. The hydrodynamic diameter may be determined from dynamic light scattering (DLS) measurements of a particle sample.

The size of the particle and the composition of the particle may be selected to provide the most appropriate or beneficial surface enhanced effect.

Gold and silver particles may be prepared using techniques known in the art. Examples of preparations include those described by Coulston (Coulston et al *Chem. Commun.* 2011, 47, 164) and Martin (Martin et al. *Langmuir* 2010, 26, 7410) and Frens (Frens *Nature Phys. Sci.* 1973, 241, 20), which are incorporated herein by reference in their entirety.

In one embodiment, the encapsulant is a polymer. In one embodiment, the polymer is not a polymer that is present as building block in the capsule shell. Otherwise, the polymer is not particularly limited.

Further Additional and Alternative Encapsulants

In addition to, or as alternatives to, the encapsulants mentioned above and the additional and alternative encapsulants mentioned above, the encapsulant may be selected from one or more of the further encapsulants discussed below. In one embodiment, the molecular weight preferences given above apply to these encapsulants.

In one embodiment, the encapsulant is a fragrance compound or a fragrance composition. A fragrance compound or composition has suitable odorant properties for use in a perfume.

In one embodiment, the encapsulant is a flavourant compound or a flavourant composition. A flavourant may be or include a flavour enhancer, such as a sweetener.

In one embodiment, the encapsulant is an oil, such as an essential oil. Examples of essential oils include those obtained or obtainable from sweet orange, peppermint, lemon and clove, amongst others.

In one embodiment, the encapsulant is itself a vehicle for holding a encapsulant within. For example, the encapsulant may be a liposome, micelle, or vesicle. The liposome, micelle, or vesicle may hold an encapsulant, such as one of the encapsulants described herein. Suitably loaded liposomes, micelles, or vesicles may be prepared using standard techniques known in the art. The loaded liposome, micelle, or vesicle may then be encapsulated into the supramolecular capsules of the invention using the methods described herein.

Methods for the Preparation of Capsules

In a second aspect of the invention there is provided a method for the preparation of a capsule having a shell, such as the capsule of the first aspect of the invention, the method comprising the steps of:

(i) contacting a flow of a first phase and a flow of a second phase in a channel, thereby to generate in the channel a dispersion of discrete regions, preferably droplets, of the second phase in the first phase, wherein the second phase comprises cucurbituril and one or more building blocks having suitable cucurbituril guest functionality suitable to form a supramolecular cross-linked network, thereby to form a capsule shell within the discrete region, wherein the first and second phases are immiscible.

In one embodiment, the second phase comprises either (a) a cucurbituril and (1) or (2); or (b) a plurality of covalently linked cucurbiturils and (1), (2) or (3), thereby to form a capsule shell within the discrete region, wherein the first and second phases are immiscible.

In one embodiment, the second phase comprises a cucurbituril and (1) or (2).

In one embodiment, the second phase comprises a cucurbituril and (1).

In the method of the invention a dispersion of the second phase is created within the continuous first phase. In one embodiment, one of the first and second phases is an aqueous phase and the other phase is a water immiscible phase.

In one embodiment, the second phase is an aqueous phase. The first phase is a water immiscible phase, for example an oil phase.

In one embodiment, the first phase is an aqueous phase. The second phase is a water immiscible phase, for example an oil phase.

In one embodiment, the method further comprises the step of (ii) collecting the outflow from the channel, thereby to obtain a droplet, within which is a capsule.

In one embodiment, the method comprises the step (ii) above and (iii) optionally drying the capsule obtained in step (ii). The drying step refers to the desolvation of the droplet and the capsule. Where the second phase is an aqueous phase, the drying step is a dehydration.

In one embodiment, the flow of the second (dispersed) phase is a flow generated by the combination of a plurality of sub-flows, where each sub-flow comprises a reagent for use in the preparation of the shell. Thus, one sub flow may comprise a cucurbituril (as in case (a)) or a plurality of covalently linked cucurbiturils (as in case (b)). Further sub-flows may comprise a first building block and a second building block (as with composition (1)). The first and second building blocks may be contained within the same or different sub-flows. In one embodiment cucurbituril and the building block (or blocks) are provided in separate sub-flows.

In one embodiment, a sub-flow is provided for each reagent for use in the preparation of the shell. In this embodiment, it is possible to independently alter the flow rate of each sub-flow, thereby independently altering the final concentration of a particular reagent in the formed discrete region. The ability to independently alter the flow rate and therefore reagent concentration allows control over the structure of the shell formed. Thus, the pore size and the thickness of the shell may be controlled by appropriate changes in the sub-flow rates.

The sub-flows may be brought into contact prior to contact with the flow of the first phase. In this arrangement, multiple sub-flows may be brought into contact at the same time, or may be contacted in a sequence. Alternatively, the sub-flows may be brought into contact at substantially the same time as the second phases are brought into contact with the flow of the first phase.

In order to minimise the formation of an unstructured aggregation, including for example a hydrogel, within the second phase, the cucurbituril or the plurality of covalently linked cucurbiturils are brought into contact with the building blocks immediately before or at substantially the same time as the second phases are brought into contact with the flow of the first phase.

In one embodiment, the flow of the second phase is brought into contact with the flow of the first phase substantially perpendicular to the first phase. In this embodiment, the channel structure may be a T-junction geometry. The path of the channel may follow the path of the flow of the first phase, in which case the second flow will be substantially perpendicular to the resulting combined flow in the channel. Alternatively, the path of the channel may follow the path of the flow of the second phase, in which case the first phase flow will be substantially perpendicular to the resulting combined flow in the channel.

Methods utilising a T-junction geometry provide discrete regions, typically droplets, of the aqueous phase in the oil phase as a result of induced shear forces within the two phase system.

In one embodiment, an additional flow of the first phase is provided. The first phase flows are brought into contact with each side of the second phase flow in a channel, and the flow of phases is then passed through a region of the channel of reduced cross-section (an orifice) thereby to generate a discrete region, preferably a droplet, of the second phase in the channel. Such methods, which have an inner second phase flow and two outer first phase flows, are referred to as flow-focussing configurations.

Methods using flow-focussing techniques provide discrete regions, typically droplets, of the second phase in the first phase as a result of the outer first phase applying pressure and viscous stresses to the inner second phase, thereby generating a narrow flow of that phase. This narrowed flow then separates into discrete regions, typically droplets, at the orifice or soon after the combined flow has passed through the orifice.

In one embodiment, the discrete region is a droplet.
In one embodiment, the discrete region is a slug.
After the discrete region is formed in the channel, the discrete region may be passed along the channel to a collection area. The residence time of the discrete region in the channel is not particularly limited. In one embodiment, the residency time is sufficient to allow the shell to form.

As the discrete region is passed along the channel it may be subjected to a mixing stage whereby the components of the discrete region are more evenly distributed around that discrete region. In one embodiment, the channel comprises a winding region. The winding region may take the form of a substantially sigmoid path through which the discrete region is passed.

In one embodiment, the second phase further comprises a component for encapsulation, and the step (i) provides a capsule encapsulating the component.

The first phase and the second phase may be contacted at a simple T-junction. The second phase may be formed from the combination of separate flows of cucurbituril and (1), (2) or (3) as appropriate. Where there are more than two components, these components may be brought into contact simultaneously or sequentially.

These flows may be contacted prior to contact with the first phase. Alternatively they may be brought into contact simultaneously on contact with the first phase.

Discrete regions of second phase are generated in the channel as the immiscible first phase shears off the second phase. The frequency of shearing is dependent on the flow rate ratio of the two phases.

In one embodiment, the flow rate is selected so as to provide a set number of droplets per unit time (droplets per second).

The droplets may be prepared at a rate of at most 10,000, at most, 5,000, at most 1,000 or at most 500 Hz.

The droplets may be prepared at a rate of at least 1, at least 10, at least 50, at least 100, or at least 200 Hz.

In one embodiment, the droplets may be prepared at a rate that is in a range where the minimum and maximum rates are selected from the embodiments above. For example, the rate is in range 100 to 500 Hz.

In one embodiment, the method comprises the step of (iii) drying the capsule. The drying step at least partially removes solvent (which may be water or organic solvent) from the capsule and may be referred to as desolvation.

There are no particular limitations placed on the method for drying the capsules. In one embodiment, the capsules obtained may simply be allowed to stand at ambient conditions, and the solvent permitted to evaporate.

In one embodiment, the method comprise the steps (ii) and (iii) and optionally the step (iv), which step is a washing step, whereby the capsules obtained are washed with a solvent. The purpose of the washing step may be to remove surfactant (where used) or any other component used in the shell-forming step. Step (iv) may be performed as an intermediate step between steps (ii) and (iii)

In one embodiment, the method comprises the step of (iii) drying the capsule and (v) subsequently resolvating the capsule. The resolvation step may be performed minutes, hours, days, weeks or months after step (iii) is complete.

In one embodiment, a reference to a size of a droplet is also a direct reference to a size of a capsule. The droplet is a droplet formed in a channel of a fluidic device or a droplet that is collected from the channel of such a device. The size refers to a droplet that has not been subjected to a desolvation step.

The capsules may be desolvated for storage and subsequently resolvated for use. In the resolvation step the capsule is contacted with solvent thereby to resolvate the capsule.

A capsule formed directly after preparation is substantially spherical. Desolvation of the capsule may result in the collapse of the capsule as the spherical edge becomes distorted. The shell material appears to fold in a random manner.

In the preparation method described herein, a droplet is formed and the shell of a capsule forms at the interface of the droplet. The formed droplet may be subjected to a desolvation step, thereby resulting in the shrinkage of the capsule shell. In one embodiment, the size of the capsule refers to the size of a capsule that has been subjected to a dehydration step.

The shell of the capsule may have pores. Such pores may be is a size suitable to permit an encapsulated molecule to pass through the shell thereby to be released from the capsule.

The flow rate of the first phase and/or the second phase may be varied to allow preparation of droplets, and therefore capsules, of a desired size. As the flow rate of the first phase is increased relative to the second phase, the average size of the droplet decreases, and the formed capsule size decreases also.

Typically, the flow rate of the first phase is at least 1.5, 2, 3, 4, 5 or 10 times greater than that of the second phase.

In one embodiment, the flow rates of the first and the second phases are selected so as to provide droplets having a desired average diameter.

The average particle size may be determined from measurements of a sample of droplets collected from the flow channel using simple microscopy techniques.

In one embodiment, the each droplet is a microdroplet.

In one embodiment, the each droplet is a nanodroplet.

In one embodiment, the average size of the droplet is at least 1, 5, 10, 20, 30, or 40 µm in diameter.

In one embodiment, the average size of the droplet at most 400, 200, 100, 75 or 50 µm in diameter.

In one embodiment, the average size of the droplet is in a range where the minimum and maximum rates are selected from the embodiments above. For example, the average size is in the range 1 to 100 µm.

The droplet formed from the fluidic preparation has a narrow size distribution. This may be gauged empirically by observation of the packing of collected droplets. A hexagonal close packing arrangement of collected droplets is indicative of a low i value (see, for example, L. J. De Cock et al. Angew. Chem. Int. Ed. 2010, 49, 6954).

In one embodiment, the droplets have a relative standard deviation (RSD) of at most 1.5%, at most 2%, at most 4%, at most 5%, at most 7%, or at most 10%.

The concentration of one or more of the components in the second phase may be altered. Changes in concentration may alter the physical and chemical properties of the shell material subsequently formed.

In one embodiment, the concentration of cucurbituril may be altered in order to alter the degree of linking and/or crosslinking in the formed network. An increase in linking or cross-linking is associated with a decrease in the pore size in the material.

In one embodiment, the concentration of cucurbituril and building block present in the second phase may be altered in order to alter the thickness of the shell.

In one embodiment, the concentration of the cucurbituril in the second phase is at least 0.05, at least 0.1, at least 0.2, at least 0.3, at least 0.5, at least 1.0, at least 5.0 or at least 10 µM.

In one embodiment, the concentration of the cucurbituril in the second phase is at most 500, at most 200, at most 100, at most 75, at most 50 µM.

In one embodiment, the concentration of the cucurbituril in the second phase is in a range where the minimum and maximum rates are selected from the embodiments above. For example, the concentration of the cucurbituril in the second phase is in the range 0.1 to 100 µM.

In one embodiment, the concentration of a building block in the second phase is at least 0.05, at least 0.1, at least 0.2, at least 0.3, at least 0.5, at least 1.0, at least 5.0 or at least 10 µM.

In one embodiment, the concentration of a building block in the second phase is at most 500, at most 200, at most 100, at most 75, at most 50 µM.

In one embodiment, the concentration of a building block in the second phase is in a range where the minimum and maximum rates are selected from the embodiments above. For example, the concentration of a building block in the second phase is in the range 0.1 to 100 µM.

The reference to a building block may refer to a first building block or a second building block as described herein.

In one embodiment, the ratio of cucurbituril concentration to building block concentration in the second phase is selected from the group consisting of: 1:1, 1:2, 2:3, 1:3, 15:85, 7.5:92.5 and 5:95.

Where two or more building blocks are present the concentration of building block may refer to the combined concentration of all building blocks present.

In one embodiment, the concentration of the cucurbituril and the building block refers to the concentration in the second phase after any sub-flows, where present, have been brought together.

Alternatively, the concentration of the cucurbituril and the building block refers to the concentration within a sub flow, prior to the bringing together of the sub-flows to make the second phase. In this embodiment, it will be appreciated that the final concentration of a particular reagent in the second phase will be less than the concentration of that reagent in the sub-flow. The final concentration of a particular reagent in the final combined second phase is determined by the flow rate of the sub-flow in relation to the flow rate of the one or more sub-flows with which it is combined. The ratio of flow rates will therefore influence the final concentration of a reagent.

In one embodiment, the concentration of a component in the second phase may be 5%, 7.5%, 10%, 15%, 20%, 25%, 30%, 33%, 35%, 40%, 45%, 50%, 55%, 60%, 65%, 66%, 70%, 75%, 80%, 85% 90%, or 95% of the concentration of that component in the sub-flow.

In one embodiment, the second phase is generated from the combination of three separate sub-flows. These flows each independently comprise a cucurbituril, a first building block and a second building block. Where, the flow rates are equal, it will be appreciated that the concentration of each of the cucurbituril, the first building block and the second building block in the combined aqueous phase will be a third of the concentration of each of the reagents within the respective sub-flows.

In one embodiment, the ratio of flow rates for the cucurbituril, first building block and second building block sub-flows is selected from the group consisting of: 1:1:1, 2:2:1, 1:1:2, 15:15:70, 7.5:7.5:85, and 5:5:90.

In this embodiment, the first building block may comprise a polymeric molecule and the second building block may comprise a particle.

In one embodiment, the methods of the invention are performed at ambient temperature.

In one embodiment, the methods of the invention are performed at about 5, 10, 15, 20, 25, or greater than 25° C.

Apparatus

The methods of the present invention call for a flow of a second phase and a flow of a first phase, which is immiscible with the second phase, to be brought together in a channel, thereby to generate a dispersion of the second phase in the first phase. Methods for the generation of a flow of a first phase and a second phase are well known in the art.

In one embodiment, each flow (either a flow or a sub-flow) may be generated from a syringe under the control a programmable syringe pump. Each syringe is loaded with an appropriate aqueous solution or water-immiscible phase.

In the method of the invention, droplets may be collected only when the flows are at the required flow rate The channel in which the second phase and first phase flows are contacted is not particularly limited.

In one embodiment, the channel is a microfluidic channel.

In one embodiment, the channel has a largest cross-section of at most 1,000, at most 500, at most 200, at most 100 or at most 50 µm.

In one embodiment, the channel has a largest cross-section of at least 0.1, at least 1, at least 10 or at least 20 µm.

The channel may be provided in an appropriate substrate. The substrate is one that will not react with the components of the complexable composition.

The substrate may be a PDMS-based substrate.

The preparation of substrates for use in fluidic flow techniques are well known to those of skill in the art. Examples in the art include the preparation described by Yang et al. (Yang et al. *Lab Chip* 2009, 9, 961), which is incorporated herein.

Second Phase

The second phase is immiscible with the first phase. The second phase may be referred to as a dispersed phase, particularly once it has contacted the first phase and is separated into discrete regions, such as droplets.

In one embodiment, one of the first or second phases is an aqueous phase. Therefore, the other of the first or second phases is water immiscible.

However, it is not essential that one of the phases is an aqueous phase, and those familiar with fluidic techniques will recognise that other combinations of immiscible phases may be used. For example, the use of a chloroform organic phase together with a polyvinyl alcohol phase has been described (see Yang et al. *Lab Chip* 2009, 9, 961).

Typically the second phase is a phase that is suitable for holding, for example dissolving, one or more of the cucurbituril and the building blocks, and the encapsulant, where present.

In one embodiment, the second phase is chosen for its ability to dissolve the cucurbituril.

Cucurbituril compounds differ in their water solubility. The methods of preparation may be adapted to take into account this solubility. As described herein, the methods of the invention call for the use of a second phase comprising the cucurbituril. The second phase may be selected as a phase that is suitable for dissolving the cucurbituril. Where the cucurbituril compound is water soluble, the second phase may be an aqueous phase. Where the cucurbituril compound has low or no water solubility, the second phase may be a water immiscible phase, such as an oil phase or an organic phase.

In one embodiment, the flow rate of the second phase is at most 1,000, at most 500, at most 250, or at most 100 µL/min.

In one embodiment, the flow rate of the second phase is at least 0.05, at least 0.1, at least 0.5, at least 1, at least 5, at least 10, or at least 50 µL/min.

In one embodiment, the flow rate of the second phase is in a range where the minimum and maximum rates are selected from the embodiments above. For example, the flow rate of the second phase in the range 0.1 to 100 µL/min.

The flow rate of the second phase refers to the flow rate of that phase before the phase is contacted with the first phase.

Where the second flow is a combination of two or more sub-flows that are bought into contact, the flow rate of the second phase refers to the numerical sum of the flow rates of each of the sub-flows. The flow rate refers to the combined flow rate of the sub-flows when they are brought into contact, which may be before, or at substantially the same time as, the flows come into contact with the first phase.

First Phase

The first phase comprises a component that is immiscible with the second phase. The first phase may be referred to as a continuous or carrier phase.

In one embodiment, the flow rate of the first phase is at most 1,000, at most 500, or at most 250 µL/min.

In one embodiment, the flow rate of the first phase is at least 10, at least 50, or at least 100 µL/min.

In one embodiment, the flow rate of the first phase is in a range where the minimum and maximum rates are selected from the embodiments above. For example, the flow rate of the first phase in the range 100 to 250 µL/min.

The flow rate of the first phase refers to the flow rate of that phase before the phase is contacted with the second phase.

Where a flow focusing technique is used to develop discrete regions of a second phase, the flow rates of the two first phases may be the same.

The first phase may additionally comprise a surfactant. The surfactant is provided in the first phase in order to stabilise the macroemulsion that is formed in the fluidic preparation methods. The step of forming the discrete region (such as a droplet) may require the presence of a surfactant. Furthermore, the presence of a surfactant is useful in limiting or preventing the coalescence of the droplets collected.

The surfactant chosen is not particularly limited, and encompasses any surfactant that is capable of promoting and/or stabilising the formation of discrete regions, such as droplets, of the second phase in the first phase.

Suitable surfactants for use in the present invention include those described by Holtze et al. *Lab Chip* 2008, 8, 1632. Typically such surfactants comprise an oligomeric perfluorinated polyether (PFPE) linked to a polyethyleneglycol. Such surfactants are especially useful for stabilising water-in-fluorocarbon oil emulsions.

The surfactant is present at most 0.1%, at most 0.2%, at most 0.5%, at most 0.75%, at most 1%, at most 2%, at most 5% w/w to the total phase.

The surfactant is present at least 0.05% or at least 0.07% w/w to the total phase.

Where the first phase is an aqueous phase, the surfactant may be polyvinyl alcohol.

In one embodiment, the first phase has a solubility in the second phase of at most 50, at most 20, at most 10, or at most 5 ppmw.

In one embodiment, second phase has a solubility in the first phase of at most 50, at most 20, at most 10, or at most 5 ppmw.

Aqueous Phase

The present invention calls for the use of an aqueous phase either as the continuous or dispersed phase in the methods of the invention. Methods for the preparation of suitable aqueous solutions comprising the appropriate components will be apparent to those of skill in the art.

Water Immiscible Phase

The present invention calls for the use of a phase that is immiscible with water. That phase may be an oil-based phase (oil phase) or an organic solvent-based phase (organic phase), or a combination of the two.

In one embodiment, the water immiscible phase is a liquid phase.

In another embodiment, the water immiscible phase is a gas phase. Typically, this embodiment is appropriate where the water immiscible phase is the first phase.

The oil phase has as a principal component an oil. The oil is a liquid at ambient temperature.

The oil is inert. That is, it does not react with the cucurbituril to form a complex, or any other product. The oil does not react with any building block present. The oil does not react with the shell.

In one embodiment, the oil is a hydrocarbon-based oil.

In one embodiment, the oil is a mineral oil.

In one embodiment, the oil is a fluorinated hydrocarbon oil.

In one embodiment, the oil is a perfluorinated oil. An example of a perfluorinated for use in the invention is FC-40 (Fluoroinert as available from 3M).

In one embodiment, the oil is a silicone oil.

In one embodiment, the water immiscible phase has as a principal component an organic solvent. For example, the organic solvent is selected from chloroform and octane.

Capsule with Encapsulant

The methods of the invention are suitable for the incorporation of a material into a capsule. The capsule produced therefore comprises an encapsulated material (an encapsulant).

In a further aspect of the invention there is provided a method for the preparation of a capsule having a shell, wherein the capsule encapsulates a component, the method comprising the steps of:

(i) contacting a flow of a first phase and a flow of a second phase in a channel, thereby to generate a discrete region, preferably a droplet, of the second phase in the channel, wherein the second phase comprises either (a) a cucurbituril, a component and (1) or (2); or (b) a plurality of covalently linked cucurbiturils, a component and (1), (2) or (3), thereby to form a capsule shell within the discrete region, wherein the capsule encapsulates the component and the first and second phases are immiscible.

The method of the invention is particularly attractive as it allows all the component present in the second phase flow to be encapsulated within the capsule shell. The formation of the capsule shell occurs at the boundary of the droplet at the interface with the first phase. All the component, therefore, is encapsulated within the formed shell. The present method therefore provides an efficient method for the incorporation of component into a capsule.

In one embodiment, the component to be encapsulated is provided in a sub-flow. This sub-flow is brought into contact with one or more other sub-flows that comprise the reagents for the preparation of the shell, for example cucurbituril and the one or more building blocks. The sub-flow comprising the component to be encapsulated may be brought into contact with another sub-flow prior to contact with the flow of the first phase. Alternatively, the sub-flow comprising the component to be encapsulated may be brought into contact with another sub-flow at substantially the same time as the first phases are brought into contact with the flow of the second phase.

Providing a sub-flow for the component to be encapsulated that is separate from a sub-flow comprising a material for the capsule shell allows the concentration of the component in the formed discrete region (such as a droplet) to be controlled, and the final amount of encapsulant present within the shell to be likewise controlled.

In one embodiment, the method is a method for the preparation of a capsule encapsulating a plurality of components. In this embodiment, the aqueous phase comprises at least a first component to be encapsulated and a second component to be encapsulated. The plurality of components may be provided in separate sub-flows that are contacted prior to contact with the first phase or at substantially the same time as the second phases are brought into contact with the flow of the first phase.

In one embodiment, the concentration of a component to be encapsulated in the second phase is at least 0.01, at least 0.02, at least 0.05, at least 0.1, at least 0.2, at least 0.3, at least 0.5, at least 1.0, or at least 5.0 µM.

In one embodiment, the concentration of a component to be encapsulated in the second phase is at most 500, at most 200, at most 100, at most 75, at most 50, or at most 10 µM.

In one embodiment, the concentration of a component to be encapsulated in the second phase is in a range where the minimum and maximum rates are selected from the embodiments above. For example, the concentration of a component to be encapsulated in the second phase is in the range 0.02 to 50 µM.

In one embodiment, the concentration of the component to be encapsulated refers to the concentration in the second phase after any sub-flows, where present, have been brought together.

Alternatively, where the aqueous flow is a combination of two or more sub-flows that are bought into contact, the concentration of the component to be encapsulated refers to the concentration within a sub-flow, prior to the bringing together of the sub-flows to make the second phase. In this embodiment, it will be appreciated that the final concentration of the encapsulant in the second phase will be less than the concentration of that reagent in the sub-flow. The final concentration of the encapsulant in the final combined second phase is determined by the flow rate of the sub-flow in relation to the flow rate of the one or more sub-flows with which it is combined. The ratio of flow rates will therefore influence the final concentration of a reagent.

In one embodiment, the concentration of a component in the aqueous phase may be 5%, 10%, 15%, 20%, 25%, 30%, 35%, 40%, 45%, 50%, 55%, 60%, 65%, 70%, 75%, 80%, 85% 90%, or 95% of the concentration of that component in the sub-flow.

Where an additional encapsulant sub-flow is provided along with the sub-flows of each of the cucurbituril and the one or more building block flows, the flow rates for each of the cucurbituril and the one or more building blocks may be altered to take into account the dilution effect of providing an additional sub-flow for the encapsulant.

The present invention provides a capsule that is obtained or obtainable from any of the methods described herein. The capsule may comprise an encapsulated component, which may also be prepared using the methods described herein.

Analysis of Capsule

In the sections above, the analysis of the shell material, shell shape, shell dimensions is described. For example, the capsule may be analysed by simple bright field microscopy to determine the shape of the capsule shell. The images obtained may also be used to determine the cross-section, typically the diameter, of the capsule shell.

The capsule shell may also be analysed for shape, cross-section and its thickness using scanning electron microscopy and transmission electron microscopy. The latter is particularly useful for studying the compositions of the shell network. For example, where the network comprises a polymeric compound building block and a nanoparticle building block, the nanoparticles may be observed as dispersed throughout a polymeric material. This dispersion is the result of the complexation and interlinking of nanoparticles and polymeric molecules with the cucurbituril.

The present inventors have usefully incorporated a detectable label into the shell material and into the encapsulant, thereby to allow each to be located and defined. Where that label is a fluorescent label, it may be detected by laser scanning fluorescent microscopy, for example.

The present inventors have also generated capsules having building blocks that are capable of providing a surface enhanced resonance effect. Particularly, this effect is provided by particles, such as metal nanoparticles, that are used as building blocks.

The presence of building blocks within the shell that are capable of providing a surface enhanced resonance effect can be used advantageously to analyse the shell itself, or the material encapsulated within. A building block may be chosen to provide the greatest a suitably useful enhancement. For example, a larger nanoparticle building block, for example a 5 nm diameter nanoparticle, may provide an enhancement greater than that of a 2 nm diameter nanoparticle.

In one embodiment, the surface enhanced spectroscopy is surface enhanced Raman spectroscopy (SERS).

In one embodiment, the surface enhanced spectroscopy is Coherent anti-Stokes Raman spectroscopy (CARS).

In one embodiment, the surface enhanced spectroscopy is photoluminescence spectroscopy.

In one embodiment, the surface enhanced spectroscopy is infrared spectroscopy.

The present inventors have demonstrated that surface enhanced resonance spectroscopy may be used to confirm the presence of an encapsulant within the capsule. For example, SERS may be used to identify the presence of a biological molecule, such as dextran, by identification of the characteristic signals in the Raman spectrum for the dextran.

The intensity of the peaks may be used to quantify the amount of encapsulant present within the capsule.

Surface enhanced spectroscopic techniques are well known to those in the field, and suitable techniques are described in detail herein.

Use of Capsules

The capsules described herein are suitable for use as encapsulants for material. This material may be stored within the capsule and released from the capsule as required.

In one embodiment there is provided a capsule of the invention comprising an encapsulated component.

In one aspect, the present invention provides a method of delivering a component to a location, the method comprising the steps of:

(i) providing a capsule of the invention, which comprises an encapsulated component;
(ii) delivering the capsule to a location; and
(iii) permitting release of the encapsulated component from the capsule at the location.

In one embodiment, the location is in vivo.

In one embodiment, the location is ex vivo.

In one embodiment the release of the encapsulated component is in response to an external stimulus.

In one embodiment, the external stimulus is selected from the group consisting of competitor guest compound, light, oxidising agent, and reducing agent.

In one embodiment the release of the encapsulated component is in response to a change in the local conditions.

In on embodiment, the change in local conditions may be a change in pH, a change in temperature, a change in oxidation level, change in concentration, or the appearance of a reactive chemical entity.

In one embodiment, the release of the encapsulant is achieved by disrupting the complex formed between the cucurbituril and the guest molecule or molecules. In one embodiment, a compound covalently linked to a competitor guest molecule is provided at the release location. The competitor guest molecule displaces a guest molecule of a building block thereby to disrupt the network that forms the capsule shell. Such disruption may cause pores to appear in the shell, through which the encapsulated compound may pass through and be released. In one embodiment, the competitor guest molecule causes an extensive disruption of the capsule shell.

In one embodiment, the release of the encapsulant is achieved by disrupting the complex using light, for example an incident laser light. In their experiments to determine the surface enhanced spectroscopic properties of the capsules of the invention (for examples those capsule containing particles), the present inventors have found that exposure of the capsule to a laser light results in the at least partial loss of integrity of the capsule. the inventors have found that SERS analysis may still be conducted on the capsules of the inventions. When the power of the incident laser light is increased and/or the exposure time of the capsules to the laser light is increased, the capsules are seen to degrade. The degrading effect may be influences by the components of the shell, for example the nature of the building blocks. For example, small gold nanoparticles (e.g. 5 nm diameter) are known to absorb rather than scatter incident laser light. This absorbed light may radiate as heat, which may have the effect of disrupting the local network of complexes.

In one embodiment, the capsule encapsulates two, or more, components.

Where there are two or more components, the components may be later released simultaneously, or sequentially.

In one embodiment, a first component is released first. A second component is released after the first component.

In one embodiment, the capsule of the invention is suitable for connection to a surface. For example, the capsule may be provided with functionality that is suitable for forming a bond, such as a covalent bond, to the surface. This functionality may be contained within a building block that is a component of the shell. The capsules may be arranged on a surface to provide an array.

Alternative Guest-Host Supramolecular Complexes

Described herein are capsules having a shell that is obtainable from the supramolecular complexation of cucurbituril with building blocks covalently linked to appropriate cucurbituril guest molecules.

In a further general aspect of the invention, the present invention provides capsules having a shell that is obtainable from the supramolecular complexation of a host with building blocks covalently linked to appropriate host guest molecules.

As noted above, the host may be cucurbituril and the guest may be a cucurbituril guest molecule. Other guest-host complexes may be used, in the alternative to the cucurbituril guest-host complex or in addition to the cucurbituril guest-host complex.

The present invention therefore encompasses the use of a guest that is capable of non-covalently hosting one or two guests, thereby to crosslink the building blocks to which the guests are covalently bound.

The use of cucurbituril is preferred owing to the high binding constants that available and the ease through which complexes, and capsules, may be assembled.

A reference to cucurbituril in the present application may therefore be taken as a reference to an alternative host. A reference to a cucurbituril guest molecule may therefore be taken as a reference to an alternative host guest molecule. The preferences set out in the sections relating to the capsule, the complex, the building block, the method for preparation, and the use of the capsule apply to the additional and alternative guest and hosts described herein, with appropriate adaptations of the features, as necessary. Thus, the inventors believe that the methods and techniques described here are generally applicable to other guest host systems.

An alternative host may be capable of forming a ternary complex. Where the complex comprises two guests within a cavity of the guest, the association constant, $K_a$, for that complex is at least $10^3$ $M^{-2}$, at least $10^4$ $M^{-2}$, at least $10^5$ $M^{-2}$, at least $10^6$ $M^{-2}$, at least $10^7$ $M^{-2}$, at least $10^8$ $M^{-2}$, at least $10^9$ $M^{-2}$, at least $10^{10}$ $M^{-2}$, at least $10^{11}$ $M^{-2}$, or at least $10^{12}$ $M^{-2}$. In this embodiment, the shell is a network having a plurality of complexes, wherein each complex comprises a host hosting a first guest molecule and a second guest molecule. The first and second guest molecules are covalently linked to a first building block, or to a first building block and a second building block.

An alternative host may be capable of forming a binary complex. Where the complex comprises one guest within a cavity of the guest, the association constant, $K_a$, for that complex is at least $10^3$ $M^{-1}$, of at least $10^4$ $M^{-1}$, of at least $10^5$ $M^{-1}$, of at least $10^6$ $M^{-1}$, of at least $10^7$ $M^{-1}$, of at least $10^8$ $M^{-1}$, of at least $10^9$ $M^{-1}$, of at least $10^{10}$ $M^{-1}$, of at least $10^{11}$ $M^{-1}$, or of at least $10^{12}$ $M^{-1}$. In this embodiment, the shell is a network having a plurality of complexes, wherein each complex comprises a host hosting one guest molecule, and each host is covalently linked to at least one other host. The guest molecules are covalently linked to a first building block, or to a first building block and a second building block.

In one embodiment, the host is selected from cyclodextrin, calix[n] arene, crown ether and cucurbituril, and the one or more building blocks have suitable host guest functionality for the cyclodextrin, calix[n]arene, crown ether or cucurbituril host respectively.

In one embodiment, the host is selected from cyclodextrin, calix[n]arene, and crown ether, and the one or more building blocks have suitable host guest functionality for the cyclodextrin, calix[n]arene, or crown ether respectively.

In one embodiment, the host is cyclodextrin and the one or more building blocks have suitable cyclodextrin guest functionality.

The host may form a binary complex with a guest. In such cases, the host will be covalently linked to one or more other guest molecules to allow the formation of crosslinks between building blocks.

In one embodiment, the host is cyclodextrin. Cyclodextrin compounds are readily available from commercial sources. Many guest compounds for use with cyclodextrin are also known.

Cyclodextrin is a non-symmetric barrel shaped cyclic oligomers of D-glucopyranose. Typically, the cyclodextrin is capable of hosting hydrophobic uncharged guests. For example, guests include those molecules having hydrocarbon and aromatic functionalities such as adamantane, azobenzene, and stilbene derivatives. Other guest molecules for cyclodextrin include biomolecules such as xylose, tryptophan, estriol, esterone and estradiol.

In one embodiment, the cyclodextrin is an α-, β- or γ-cyclodextrin. In one embodiment, the cyclodextrin is a β- or γ-cyclodextrin. Typically larger guests are used together with a γ-cyclodextrin.

The cyclodextrin has a toroid geometry, with the secondary hydroxyl groups of the D-glucopyranose located at the larger opening, and the primary hydroxyl groups at the smaller opening. One or more of the hydroxy groups, which may be the secondary or the primary hydroxy groups, may be functionalised. Typically, the primary hydroxyl groups are functionalised. In one embodiment, references to a cyclodextrin compound are references to derivatives thereof. For example, one or two primary hydroxyl groups of the cyclodextrin is functionalised with a alkylamine-containing subsistent. In another example one, two or three of the hydroxyl groups within each D-glucopyranose unit is replaced with an alkyl ether group, for example a methoxy group. A plurality of covalently linked cyclodextrins may be connected via the hydroxyl groups.

Examples of unfunctionalised and functionalised cyclodextrins are set out in Chart 1 of Rekharsky et al. (*Chem. Rev.* 1998, 98, 1875), and examples of compounds for use as guests are set out over Tables 1 to 3 and Chart 2. Rekharsky et al. is incorporated by reference herein.

In the methods of preparation, the cyclodextrin may be present in the second phase, for example in an aqueous phase, as described herein.

In one embodiment, the host is calix[n]arene. Calix[n]arenes compounds are readily available from commercial sources, or may be prepared by condensation of phenol, resorcinol and pyrogallol aldehydes, for example formaldehyde.

Many guest compounds for use with calix[n]arenes are known. Typically, the calix[n]arene is capable of hosting amino-containing molecules. Piperidine-based compounds and amino-functionalised cyclohexyl compounds may find use as guests. Further examples of guests include atropine, crytand, phenol blue, and anthrol blue amongst others.

Examples of unfunctionalised and functionalised cyclodextrins are set out in Chart 1 of Danil de Namor et al. (*Chem. Rev.* 1998, 98, 2495-2525), which is incorporated by reference herein. Examples of compounds for use as guests are set out over Tables 2, 3, 5 and 10 of Danil de Namor et al.

In one embodiment, the calix[n]arene is a calix[4]arene, calix[5]arene or calix[6]arene. In one embodiment, the calix[n]arene is a calix[4]arene.

Suitably functionalised calix[n]arenes may be prepared through use of appropriately functionalised hydroxy aryl aldehydes. For example, the hydroxyl group may be replaced with an alkyl ether-containing group or an ethylene glycol-containing group. A plurality of covalently linked calix[n]arenes may be connected via the hydroxyl groups.

In the methods of preparation, the calix[n]arene may be present in the second phase, for example in an aqueous phase or a water immiscible phase, as described herein.

In one embodiment, the host is a crown ether. Crown ether compounds are readily available from commercial sources or may be readily prepared.

Many guest compounds for use with crown ether are also known. For example, cationic guests such as amino- and pyridinium-functionalized molecules may be suitable guest molecules.

Examples of unfunctionalised and functionalised cyclodextrins are set out throughout Gokel et al. (*Chem. Rev.* 2004, 104, 2723-2750), which is incorporated by reference herein. Examples of compounds for use as guests are described throughout the text.

In one embodiment, the crown ether is selected from the groups consisting of 18-crown-6, dibenzo-18-crown-6, diaza-18-crown-6 and 21-crown-7. In the present invention, larger crown ethers are preferred. Smaller crown ethers may have be capable of binding small metal ions only. Larger crown ethers are capable of binding functional groups and molecules.

In some embodiments, the host is a guest having crown ether and calix[n]arene functionality. Such hosts are referred to as calix[n]crowns.

In the methods of preparation, the crown ether may be present in the second phase, for example in a water immiscible phase, as described herein.

Other guest-host relationships may be used as will be apparent to a person of skill in the art. Other guest-host complexes for use in the present invention include those highlighted by Dsouza et al. (*Chem. Rev.* 2011, 111, 7941-7980) which is incorporated by reference herein, and in particular those hosts set out in Schemes 6 and 7, which includes cucurbituril, cyclodextrin, and calixerane as well as cyclophane AVCyc, calixpyridine C4P and squarimide SQAM.

The use of cyclodextrin is preferred over crown ether and calix[n]arene hosts.

Other Preferences

Each and every compatible combination of the embodiments described above is explicitly disclosed herein, as if each and every combination was individually and explicitly recited.

Various further aspects and embodiments of the present invention will be apparent to those skilled in the art in view of the present disclosure.

"and/or" where used herein is to be taken as specific disclosure of each of the two specified features or components with or without the other. For example "A and/or B" is to be taken as specific disclosure of each of (i) A, (ii) B and (iii) A and B, just as if each is set out individually herein.

Unless context dictates otherwise, the descriptions and definitions of the features set out above are not limited to any particular aspect or embodiment of the invention and apply equally to all aspects and embodiments which are described.

Certain aspects and embodiments of the invention will now be illustrated by way of example and with reference to the figures described above.

Experimental and Results $^1$H NMR (400 MHz) spectra were recorded using a Bruker Avance QNP 400. Chemical shifts are recorded in ppm (δ) in CDCl$_3$ with the internal reference set to d 7.26 ppm or MeOD with the internal reference set to d 3.31 ppm. Chemical shifts are recorded in ppm (δ) in CDCl$_3$ with the internal reference set to d 77.16 ppm and d 49.00 ppm, respectively. ATR FT-IR spectroscopy was performed using a Perkin-Elmer Spectrum 100 series FT-IR spectrometer equipped with a universal ATR sampling accessory. UV-Visible studies were performed on a Varian Cary 4000 UV-Vis spectrophotometer. High resolution mass spectra were recorded on a Bruker BioASpex II 4.7e FT-ICR mass spectrometer liquid chromatography-mass spectrometry Waters ZQ. All starting materials were purchased from Alfa Aesar and Sigma Aldrich and used as received unless stated otherwise. CB[8] was prepared as documented previously by Kim (see Kim et al. *J. Am. Chem. Soc.* 2000, 122, 540). MV$^{2+}$-AuNP (5 nm) and Np-pol were synthesized according to the literature methods (see Coulston et al. *Chem. Commun.* 2011, 47, 164), while MV$^{2+}$-pol was prepared as reported previously (see Appel et al. *J. Am. Chem. Soc.* 2010, 132, 14251). All aqueous phase was dissolved in deionized water treated with a Milli-Q™ reagent system ensuring a resistivity of >15 MΩcm$^{-1}$.

General Strategy for the Formation of Capsules

The general strategy for the preparation of capsules is described below. The detailed experimental details are provided in subsequent sections.

Figure 1:
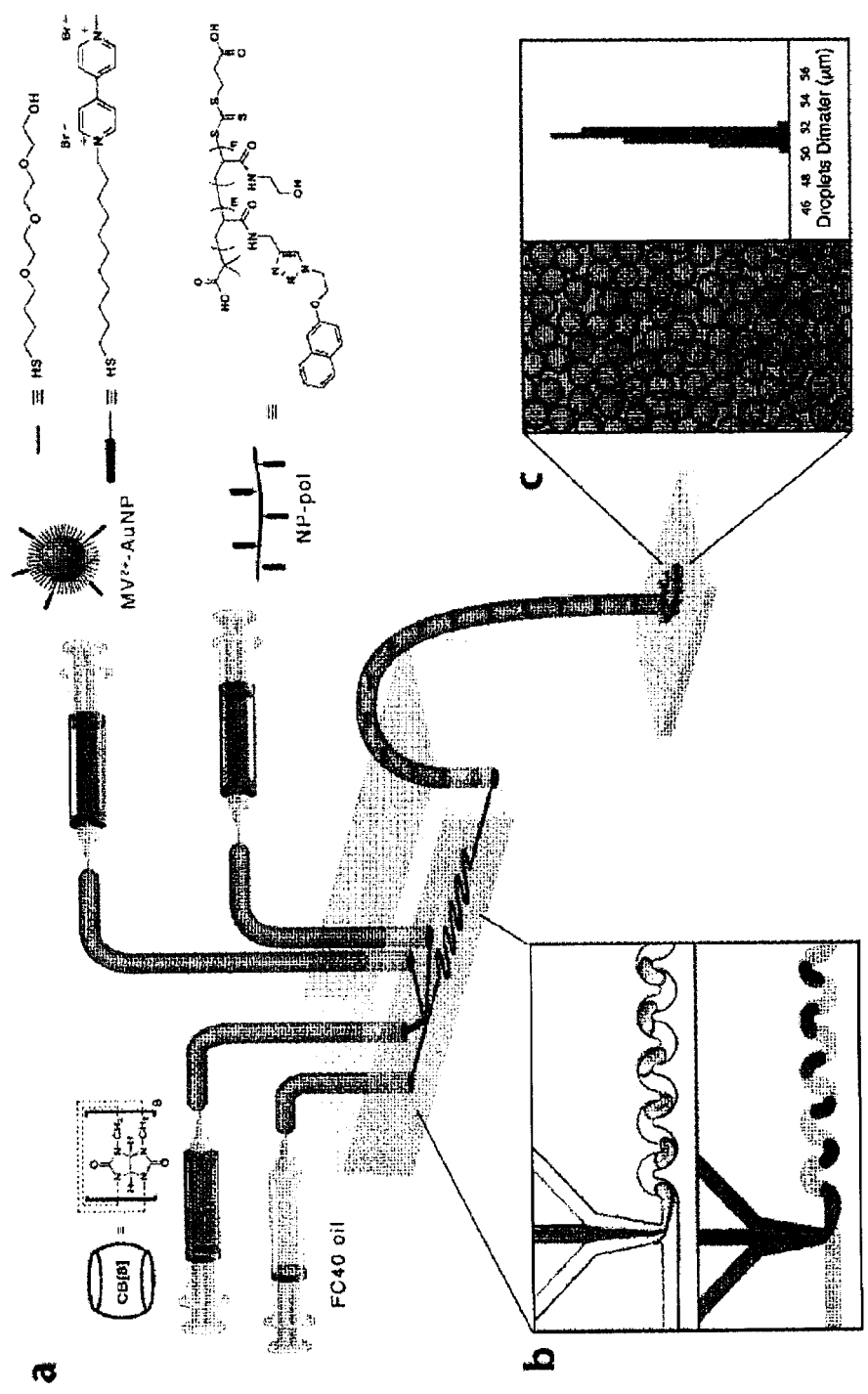
FIG. 1 (a) is a schematic representation of the microdroplet generation process using a microfluidic flow focusing device, consisting of the oil continuous phase perpendicular to a combination of aqueous solutions of CB[8] 1, $MV^{2+}$-AuNP 2, and Np-pol 3 as the dispersed phase. (b) Microscopic image and schematic representation of the flow focusing region, with downstream mixing channel allowing thorough mixing of reagents online. (c) The high monodispersity of microfluidic droplets is demonstrated by its narrow size distribution.

In a typical microcapsule preparation procedure, microdroplets were first generated using a simple T-junction geometry (see Xu et al. *AIChE Journal* 2006, 52, 3005 and Thorsen et al. *Phys. Rev. Lett.* 2001, 86, 4163) as schematically represented in FIG. 1a. In this experiment, the first phase is an oil phase comprising a surfactant, and the second phase is an aqueous phase. The oil carrier phase was directed into the device perpendicular to the aqueous dispersed phase, which comprises three inlets for the solution of CB[8]1, the solution of MV$^{2+}$-AuNP 2, and the solution of Np-pol 3. Droplets are generated as the immiscible oil phase shears off the aqueous phase at a frequency that is dependent on the flow rate ratio of the two phases. Immediately after generation, droplets pass through a winding channel that is designed for thorough mixing of the three reagents online, as depicted in FIG. 1b. With an oil:water flow rate ratio of 2:1 (where the flow rate of the aqueous phase refers to the combined flow rate of the three sub-flows)), droplets were generated at a frequency of 300 Hz and exhibit a high level of monodispersity when collected on a microscope slide, as indicated by its narrow size distribution and a low coefficient of variation of 1.3% (FIG. 1c).

Figure 2:
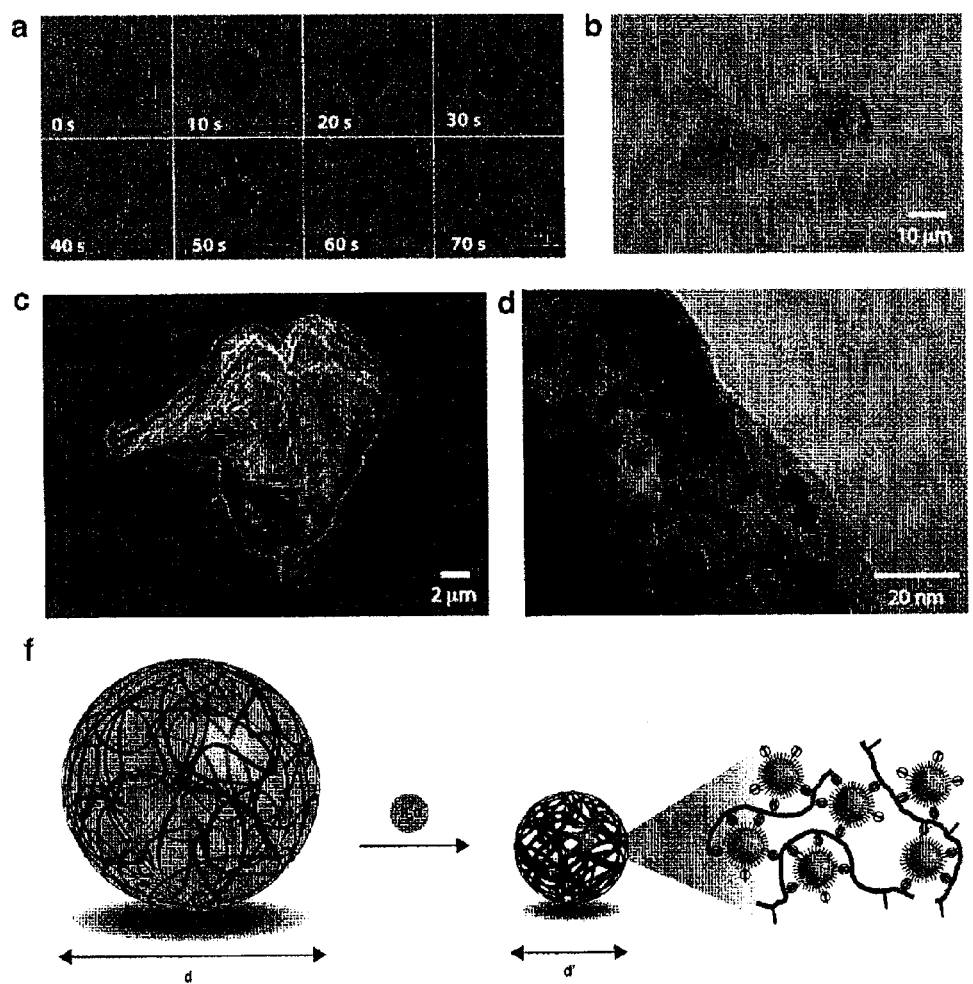
FIG. 2 (a) Bright field images of the late stage of the capsule formation process as water evaporates, rendering a collapsed microcapsule. Scale bar=5 µm. (b) Light microscope image of the exploded capsules showing the relics of the capsule shell. Scale bar=10 µm. (c) SEM image of a dried and at least partially collapsed capsule. Scale bar=2 µm. (d) TEM image of the microcapsule shell, showing 5 nm AuNPs dispersed in a mesh of polymer. Scale bar=10 nm. (e) Schematic representation of the proposed microcapsule formation process from the initial droplet (with diameter d) to the dehydrated stable capsule (with diameter d'). The cross-linking structure of 1 and 2 for the capsule material is also proposed.

The formation of microcapsules was observed after dehydration of the microdroplets. The process was captured in FIG. 2a where in the final stage of the droplets shrinking, the formation of the microcapsule was visible as the spherical shape of the droplet was distorted. It appeared to be folded at the edge in a random manner, seemingly collapsed. The nature of this capsule-like structure was further verified when exploded capsules were seen after inducing the mechanism of osmotic force of rehydration (FIG. 2b). Scanning electron microscopy (SEM) image was also obtained (FIG. 2c), showing a highly wrinkled, randomly folded structure, resembling a hollow capsule that has collapsed due to lack of internal support. The capsule shell consists of a network of MV$^{2+}$-AuNPs and polymers, as shown in the transmission electron microscopy (TEM) image (FIG. 2d), whereby individual MV$^{2+}$-AuNPs were interlinked via a mesh of presumably Np-polymers. It is likely that the capsules shells consisted of multiple layers, as the MV$^{2+}$-AuNPs appeared to be superimposing on each other. The process of this supramolecular microcapsule formation is schematically represented as in FIG. 2e. While the aqueous mixture of CB[8], MV$^{2+}$-AuNP, and Np-pol was confined in the droplets initially, the deposition of the cross-linked supramolecular composite at the oil-water interface is thought to be assisted by not only the driving force from water evaporation, but also the interfacial energy stabilization through colloidal nanoparticles (see Patra et al. *Chemistry—An Asian journal* 2010, 5, 2442). Once formed, these microcapsules were highly resistant to heat (100° C.) and reduced pressure, presumably due to the highly stable backbone of CB[8] 1:1:1 ternary complexes. Microcapsule formation was not observed when CB[8] is replaced with CB[7], which is unable to form ternary complexes, or when the AuNPs were not functionalised with the MV$^{2+}$ ligand (see below).

The interfacial templating effect was further investigated by incorporating a fluorophore to the polymer such that the distribution of the polymer can be visualized during the formation of the capsules. As shown in FIG. 3a, the rhodamine-6G functionality was incorporated into the polymer containing PEG and NP functionality (NP-RD-pol 4) via RAFT polymerization (Supplementary Information). The aqueous solution NP-RD-pol was then injected into the droplet generation device along with the aqueous solution of the other two components of the microcapsule as described before. Droplets were directed into and collected by a PDMS reservoir mounted on a glass slide and the fluorescence images of the aqueous droplets in oil were recorded using a laser scanning confocal microscope (LSCM) with an 63× oil immersion objective. FIG. 3b shows a clearly defined layer of rhodamine fluorescence confined to the water-oil interface of a droplet, indicative of the distribution of the polymer during the formation of the microcapsule. This observation is due to the hydrophobic interaction between the fluorous oil and the polymer, and is consistent with the previously reported interfacial templated synthesis of polymeric microcapsules (see Abraham et al. *Advanced Materials* 2008, 20, 2177 and Yang et al. *Lab Chip* 2009, 9, 961).

The fact that a hollow capsule can be facilely fabricated via microdroplet-assisted encapsulation in turn lead to the notion that water-soluble cargos can be loaded into these microcapsules with 100% efficiency, since the loading does not rely on passive diffusion post-microcapsule synthesis (see Peyratout et al. *Angew. Chem. Int. Ed.* 2004, 43, 3762; Abraham et al. *Advanced Materials* 2008, 20, 2177; An et al. *Biomacromolecules* 2006, 7, 580). The hypothesis was tested by loading fluorescein isothiocyanate labeled dextran (FITC-dextran) into the capsules. Dextrans, due to there high biocompatibility and versatility, have been widely exploited for delivery of drugs, proteins and imaging agents (see Mehvar *Journal of Controlled Release* 2000, 69, 1). Using the current microfluidic system, loading of the FITC-dextran was achieved by simply incorporating a solution of FITC-dextran into one of the aqueous inlets. Microdroplets generated this way contained 25% v/v FITC-dextran in addition to the mixture of CB[8], MV$^{2+}$-AuNP, and Np-RD-pol.

The LSCM images were recorded and analyzed as before and shown in FIG. 3c. The initial droplet of 46 μm in diameter exhibited a defined layer of rhodamine fluorescence at the water-oil interface, while the centre of the capsule was evenly filled with FITC fluorescence from the FITC-dextran. Examining the fluorescence intensity plot, one can clearly see that the rhodamine-exterior is distributed on the outer rim the FITC-interior, showing that the "shell" is indeed forming outside of the "cargo". As droplets dehydrate over time, the material became more concentrated and hence the fluorescence intensity increases. The same droplet of 23 μm in diameter, with its LSCM image and fluorescence intensity profile recorded (FIG. 3d), showed a less clear boundary between the FITC interior and the rhodamine exterior. In fact the FITC-interior appeared to have started to become a part of the shell wall, most probably through the interstitial sites of the capsule shell. This observation provides the foundation for the SERS analysis of this material, which will be elaborated later. Overall, these LSCM results unambiguously demonstrated the hollow nature of such supramolecular microcapsules exhibiting quantitative loading efficiency with supramolecularly built capsule shells readily subjective to various functionalities.

General Strategy for the Formation of Capsules Comprising an Encapsulant

Figure 4:
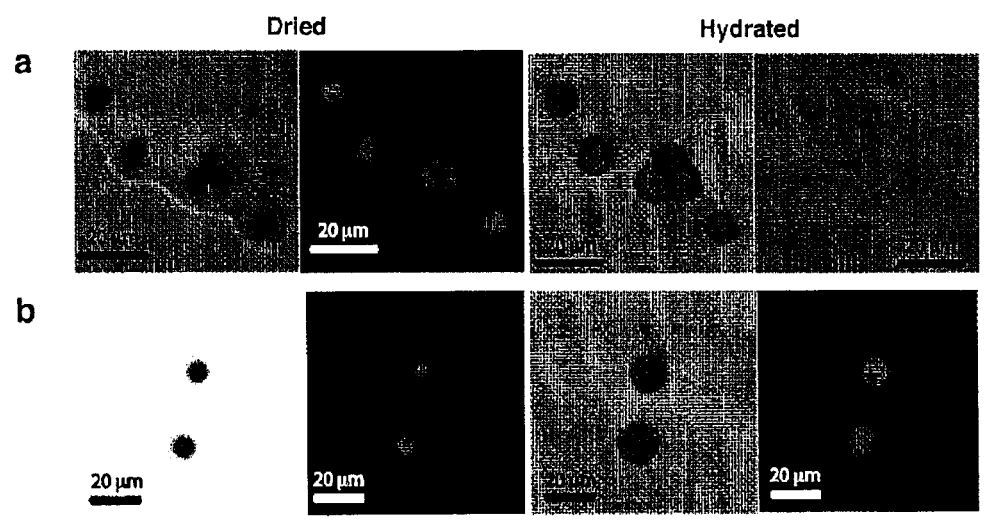
FIG. 4 is the bright field and fluorescence images of dried microcapsules containing FITC-dextran before and after rehydration, showing (a) the expansion of the microcapsule wall accompanied by the leakage of FITC-dextran (10 kDa), (b) the retaining of the FITC-dextran (500 kDa), and (c) the partial permeability of the FITC-dextran (70 kDa) for microcapsules containing twice concentrated CB[8] cross-linker. Scale bars=20 µm.
Figure 5:
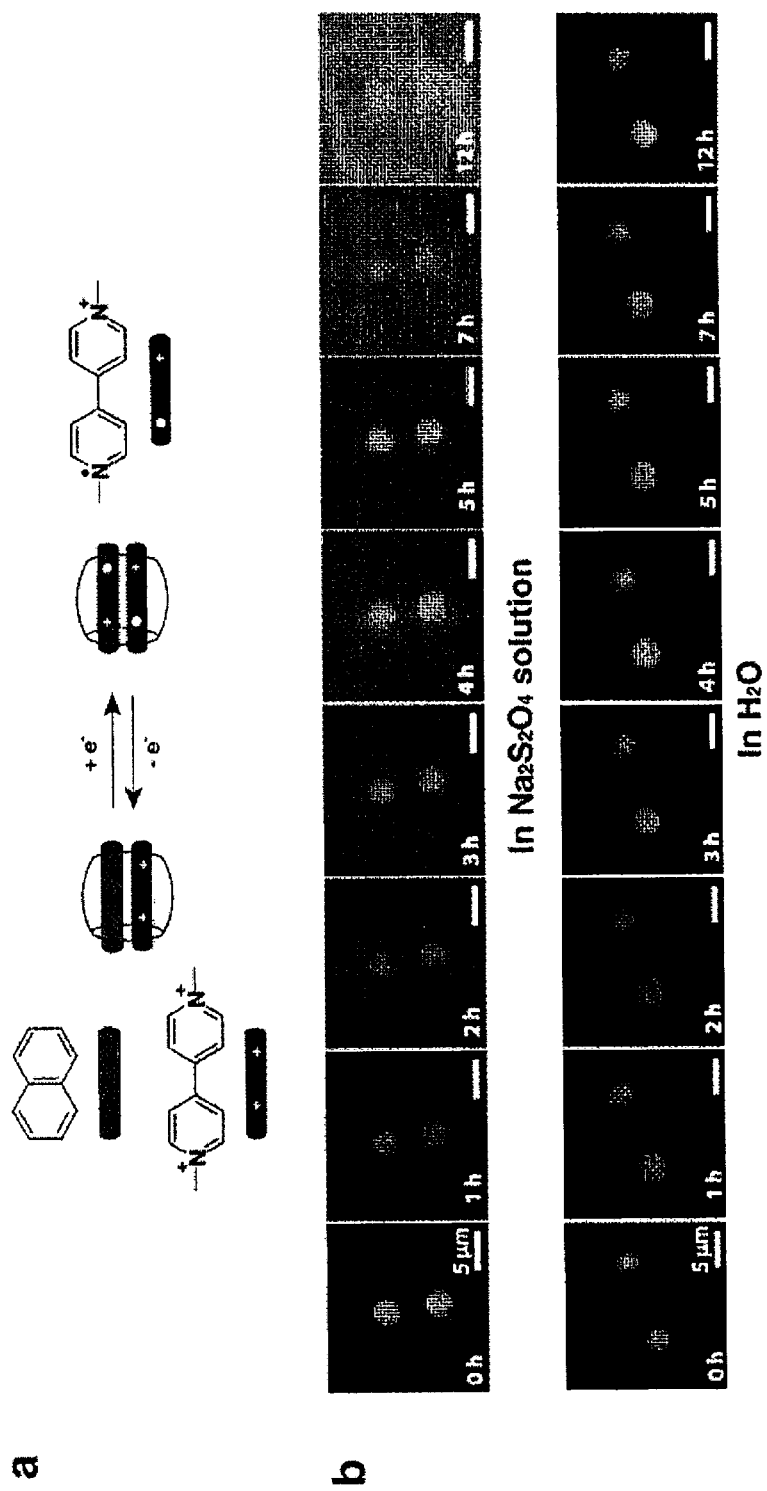
FIG. 5 (a) Schematic representation of the proposed effect of the reduction of $MV^{2+}$ on the ternary complex CB[8]

The permeability of polymeric microcapsules is usually studied using commercially available FITC-dextrans of various molecular weight as a model cargo, due to its simplicity in chemical composition and uniformity in shape (see An et al. *Biomacromolecules* 2006, 7, 580; Hermanson et al. *Physical Chemistry Chemical Physics* 2007, 9, 6442). The permeability of the present microcapsules was studied by encapsulating an aqueous solution of the FITC-dextran followed by complete dehydration, and then rehydrating the capsules while monitoring the distribution of FITC using a fluorescence microscope. As shown in FIG. 4a, dried microcapsules containing FITC-dextran exhibit bright fluorescence despite the wrinkled surface. The permeation of the fluorescent cargo was initiated by re-dispersing the capsules in water. When 10 kDa FITC-dextran-containing microcapsules were hydrated, the capsule wall expanded to resume the initial spherical outline, whereas the previously confined FITC fluorescence had leaked into the external aqueous phase (FIG. 4a). Conversely, when 500 kDa FITC-dextran was encapsulated in the capsules, upon rehydration the fluorescence was strictly localized inside the capsules without any permeation (FIG. 4b). Such a result reveals the porous nature of the microcapsule shell, which has a certain threshold for a particular sized cargo. This is in agreement with many previously reported polymeric and polyelectrolyte microcapsules (see An et al. *Biomacromolecules* 2006, 7, 580; Cavalieri et al. *ACS Nano* 2009, 3, 234; Ameloot et al. *Nat. Chem.* 2011, 3, 382). Despite swelling and expansion of the capsule wall to some extent, these capsules were stable in water for at least 48 h.

In addition to the abovementioned FITC-dextrans, other molecular weight fluorescence probe were also tested for further elucidating the permeability of the microcapsules. The results are summarized in Table 1a, where a "0" permeability denotes the complete blockage of the dextrans by the microcapsule shell, and an "100%" means that the capsules are completely permeable. Each result was observed in over 20 capsules. For this particular microcapsule fabricated from a certain ratio of the components, any dextrans with a molecular weight of 70 kDa and below are able to diffuse out of the capsules with ease while any dextrans with a molecular weight of 150 kDa and above are completely trapped by the capsule shell. Considering that the dextran chain conformation can be viewed as a small globular particle in solution, the radius of gyration ($R_E$) of the FITC-dextran can give a good evaluation of the pore size (see Andrieux et al. *Analytical Chemistry* 2002, 74, 5217). FITC-dextran with a molecular weight of 70 kDa has a radius of gyration of approximately 8 nm, while its 150 kDa counterpart has a radius of 11 nm (see Granath *Journal of Colloid Science* 1958, 13, 308). Given the permeability variation as a function of the molecular weight of FITC-dextran, this indicates that the microcapsule is permeable for macromolecules with a size less than 11 nm.

Table 1 has data for the qualitative permeability variation of (a) microcapsules containing $MV^{2+}$-AuNP, CB[8] and Np-pol with a molar ratio of 2:1:2 for $MV^{2+}$:CB[8]:Np, and (b) microcapsules containing $MV^{2+}$-AuNP, CB[8] and Np-pol with a molar ratio of 1:1:1 for $MV^{2+}$+:CB[8]:Np, as a function of the molecular weight (MW) of the fluorescence probe.

TABLE 1A

Permeability to FITC-Dextran

| Fluorescence Probe | Permeability |
| --- | --- |
| FITC-dextran, MW 500 000 | 0 |
| FITC-dextran, MW 250 000 | 0 |
| FITC-dextran, MW 150 000 | 0 |
| FITC-dextran, MW 70 000 | 100 |
| FITC-dextran, MW 40 000 | 100 |
| FITC-dextran, MW 10 000 | 100 |
| FITC, MW 376 | 100 |

Table 1B

Permeability to FITC-Dextran

| Fluorescence Probe | Permeability |
| --- | --- |
| FITC-dextran, MW 150 000 | 0 |
| FITC-dextran, MW 70 000 | 0 |
| FITC-dextran, MW 40 000 | 100 |

The relationship between this degree of permeability of the capsule shell and the extent of cross-linking between the $MV^{2+}$-AuNP and the Np-pol the via CB[8] was also investigated. For this purpose, a different microcapsule was fabricated containing twice the amount of CB[8], simply by varying the flow rate of the reagents and hence the percentage of the component. This was thought to increase the degree of cross-linking accordingly as more cross-linkers are provided before all binding sites are saturated. The permeability studies were then performed by encapsulating and diffusing FITC-dextrans with various molecular weight in water. The results are summarized in Table 1b, showing that these capsules are completely permeable to FITC-dextran with a molecular weight of 40 kDa and are impermeable to those with a molecular weight of 70 kDa and above. In comparison with the permeability cut-off of its counterpart with only 50% of the CB[8] in the mixture, these capsules have are permeable for macromolecules with a size less than 8 nm. This demonstrates the ease of adjusting the pore size of these supramolecular microcapsules by varying the ratio of capsule shell components, providing a promising potential for the pore size to be customized depending on the properties of the cargo to be released.

Additional Comments on General Strategy for the Formation of Capsules Comprising an Encapsulant The present inventors have also confirmed that the methods of the present invention may be used to prepare a capsule encapsulating a microorganism, and in particular a cell. In the examples described above for the preparation of a dextran-containing capsule, the dextran-contain phase was adapted such that a bacterial cell suspension was used in place of the dextran. In this case, a green fluorescent protein expressing (GFP) *E. coli* suspension was used. A capsule containing *E. coli* was obtained and analysed by LSCM. The LCSM image and intensity profile are shown in FIG. 10.

General Methods for Determining Capsule Surface Enhanced Resonance Effects

Figure 6A:
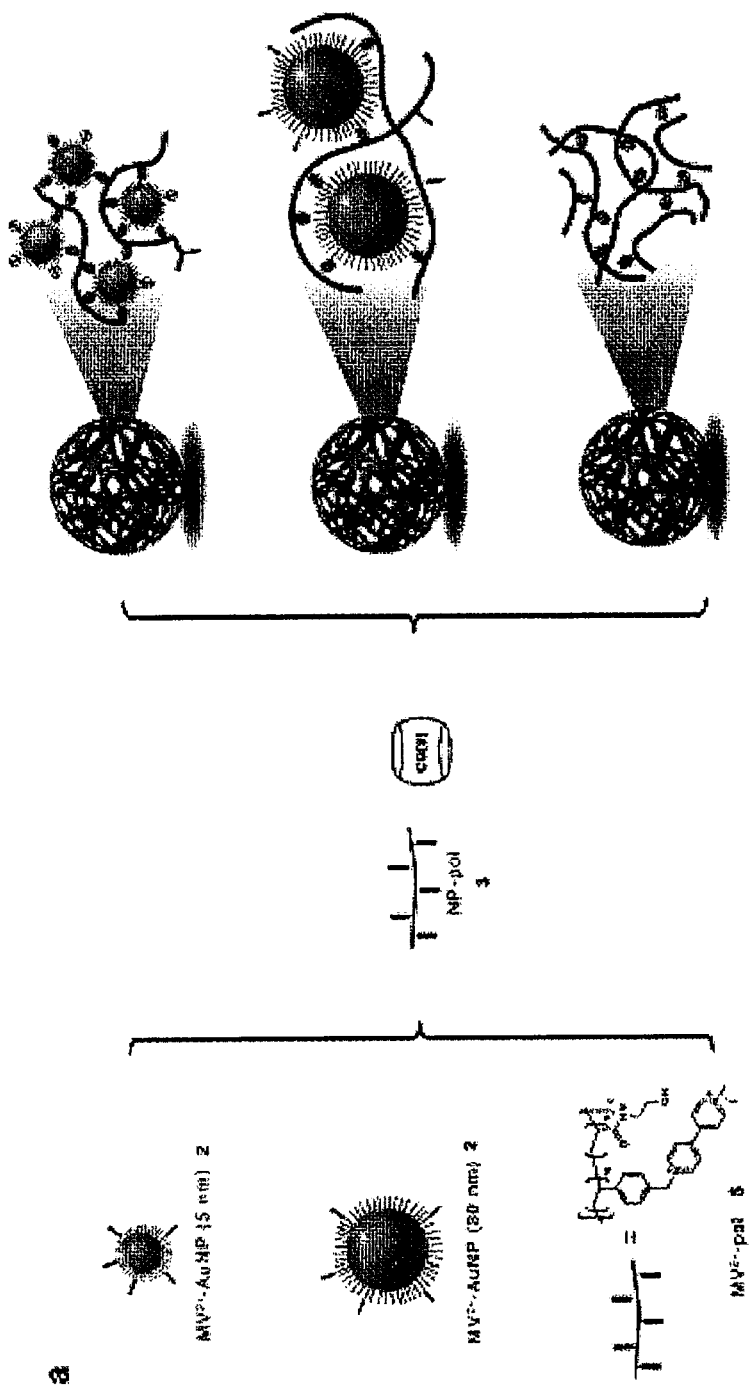

The potential of using these AuNP-containing microcapsules as a novel type of plasmonic material for surface enhanced Raman spectroscopy was also investigated. Given that as the dehydration proceeds during the capsule formation a small quantity of the encapsulated material appears to be localized in the pores of the shell, these capsules would have the potential of enhancing not only the Raman signals from the capsule shell material itself, but also possibly that of any material which has been encapsulated by the microcapsule. This hypothesis was investigated by preparing different microcapsules containing 5 nm and 20 nm $MV^{2+}$-AuNPs and with a multivalent methyl viologen functionalized polymer ($MV^{2+}$-pol 5) (FIG. 6*a*). In both examples of capsules containing AuNP, when the sample was excited using 633 nm laser line, characteristic SERS signals for CB[8] and MV were acquired: C—N—C deformation and CH2 rocking for CB[8]($830\ cm^{-1}$), and C—C ring stretching for $MV^{2+}$+($1630\ cm^{-1}$), C—N ring stretching for $MV^{2+}$+ ($1560\ cm^{-1}$), and C—C inter-ring stretching for $MV^{2+}$+ ($1308\ cm^{-1}$ peaks) (see Forster et al. *Journal of Raman Spectroscopy* 1982,12, 36) (FIG. 6*b*). However the signal strength of the capsules containing 5 nm $MV^{2+}$-AuNPs is almost negligible compared to that of the capsules containing 20 nm $MV^{2+}$-AuNPs. This is in agreement with the fact that SERS field enhancement is dependent on the distance between NPs and hence the NPs size (see Anema et al. *Annual Review of Analytical Chemistry* 2011). SERS mapping of a microcapsule showed that the SERS signals were uniformly localized only to the area of the capsule (FIG. 6*c*). A true indication of the utility of our microcapsule fabrication method, a negative control microcapsule was also synthesized by replacing the $MV^{2+}$-AuNPs with a multivalent $MV^{2+}$-polymer 5, to produce a polymer-polymer host-guest microcapsule. For this system no SERS signals were recorded (FIG. 6*c*). These results demonstrate that these supramolecular microcapsules can be used as an effective plasmonic material that gives rise to strong SERS signals for compounds between the AuNPs.

To investigate the feasibility of detecting encapsulated materials, FITC-dextran was loaded into the capsules containing $MV^{2+}$-AuNPs. Significant Raman enhancement from FITC was observed in addition to that from CB[8] and MV: 1186, 1232 and 1400 $cm^{-1}$ (FIG. 6*d*). Similar dependence of the degree of enhancement on the size of AuNPs was observed where strong signals were measured for the capsules containing the 20 nm $MV^{2+}$-AuNPs, negligible enhancement for the ones containing the 5 nm $MV^{2+}$-AuNPs, while no signals were recorded when no AuNPs were incorporated in the shell. This may also be attributed to the highly absorptive nature of the smaller size $MV^{2+}$-AuNPs (see Link et al. *The Journal of Physical Chemistry B* 1999, 103, 4212), where light is more efficiently converted to heat and thus giving poor SERS signals. AuNPs with a diameter of 20 nm, conversely, have a stronger plasmonic resonance (see Kelly et al. *Journal of Physical Chemistry B* 2002, 107, 668) and therefore produce strong SERS signals. This result indisputably demonstrated that the porous shell of this supramolecular microcapsule can be used as a SERS substrate for the detection of encapsulated materials.

Synthesis of 30 nm MV-AuNPs

AuNPs were synthesised via a modified literature Method (see Martin et al. *Langmuir* 2010, 26, 7410). In brief, to an aqueous solution (200 mL) of gold(III)chloride trihydrate (24 mg, 0.06 mmol), sodium borohydride (3.4 mg, 0.09 mmol) in 50% (v/v) aqueous ethanol (5 mL) was added and the resultant solution immediately cooled in an ice bath for 30 seconds. The solution became red in colour and was stored in the fridge (approx. 4° C.) until further use (Note: AuNPs were used within 2-3 days of preparation). Stock solutions (5 mL) for each of the thiols EG3 S1 (4.72 mg, $1.98 \times 10^{-2}$ mmol) and $MV^{2+}$ S2 (8.5 mg, $1.98 \times 10^{-2}$ mmol) were prepared in water (5 mL). Aliquots of the stock solutions ($MV^{2+}$; S2: 0.45 mL, $MV^{2+}$ 20%, approx. 1170 MV ligands per AuNP; EG3 S1: 1.8 mL) were combined and added rapidly to a swirling solution (10 mL) of the as synthesised AuNPs. The mixture was then incubated for 48 hours. The $MV^{2+}$-AuNPs were purified using centrifuge (120 secs, 12,100 g) washes with Milli-Q water. On the final wash the AuNPs were concentrated to 1 mL and used directly to prepare the microcapsules.

Mean diameter: 32 nm±5 nm, (TEM), $\lambda_{max}$ 529 nm.

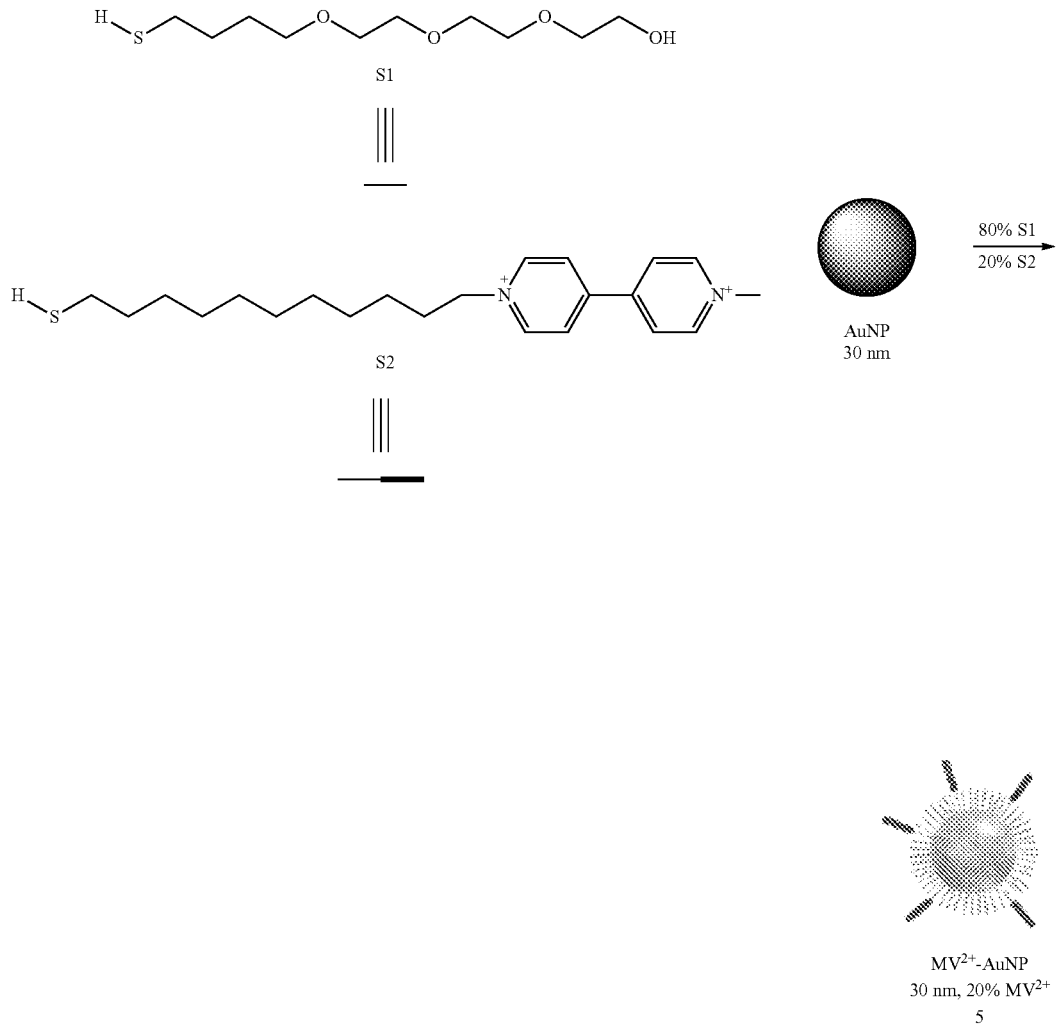

Synthesis of 50 nm MV-AuNPs

Synthesis of citrate stabilized AuNPs followed a standard literature method (see G. Frens *Nature Phys. Sci.* 1973, 241, 20). The citrate stabilized AuNPs (10 mL) were added dropwise to an aqueous solution (10 mL) of CTAB (3.6 mg, 9.8 µmol). The AuNPs were then washed using centrifuge (120 sees, 12,100 g) and Milli-Q water to remove any excess ligands. Stock solutions (5 mL) for each of the thiols EG3 S1 (4.72 mg, $1.98 \times 10^{-2}$ mmol) and $MV^{2+}$ S2 (8.5 mg, $1.98 \times 10^{-2}$ mmol) were prepared in water (5 mL). Aliquots of the stock solutions ($MV^{2+}$ S2: 0.45 mL, MV 20%, approx. 7340 MV ligands per AuNP; EG3 S1: 1.8 mL) were combined and then added rapidly to a swirling solution (10 mL) of the CTAB stabilized AuNPs. The mixture was then placed on a shaker for 48 hours at 150 rpm. The 50 mm $MV^{2+}$-AuNPs were then isolated from excess ligands with two washes using centrifuge (1×60 s, 12,100 g and 1×45 s, 12,100 g) and Milli-Q water. On the final wash the AuNPs were concentrated to 1 mL and used directly to prepare the microcapsules. Mean diameter: 52 nm±7 nm (TEM), $\lambda_{max}$ 547 nm.

General Synthesis of Np and Rhodamine Functional Polymer

Based on RAFT polymerization (see Chiefari et al. *Macromolecules* 1998, 31, 5559), S1 (6.3 mg, 0.026 mmol), S2 (0.50 g, 1.05 mmol), S3 (0.18 g, 0.52 mmol), 54 (34.0 mg, 0.052 mmol), 4,4-azobis(4cyanopentanoic acid (ACPA, 1.4 mg, 0.0052 mmol), and dioxane (1.0 mL) were added to a Schlenk tube and the mixture was thoroughly degassed using three freeze-pump-thaw cycles. The mixture was subsequently immersed in an oil bath thermostated to 70° C. for 10 h. The polymerization was quenched using liquid nitrogen, followed by dilution with THF before the solution was added dropwise to diethyl ether. The polymer was dissolved in water and then placed into a dialysis tubing (NMWCO cut off 2,000 Da) and was dialyzed against water for more than 48 hours with 3× water replacement. The aqueous solution was then freeze-dried to give the polymer 5 as a pink oil (0.46 g, 68%). $^1$H-NMR Spectroscopy ($D_2O$, 500 MHz, 298.5 K) δ=7.41, 7.18, 6.98, 4.11, 3.60, 3.31, 0.91, 0.35 ppm. FT-IR (ATR) v=2867.61, 1730.65, 1629.16, 1600.63, 1511.08, 1452.77, 1390.05, 1349.85, 1257.03, 1218.03, 1099.26, 1038.26, 947.86, 844.85, 751.49 $cm^{-1}$. GPC (DMF): $M_n$=25.7 kDa (PDI)=1.18. Fluorescence spectrum: $\lambda_{ex\ max}$ ($H_2O$)=566 nm, $\lambda_{sm\ max}$ ($H_2O$)=580 nm.

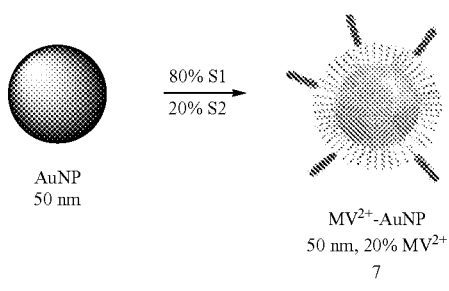

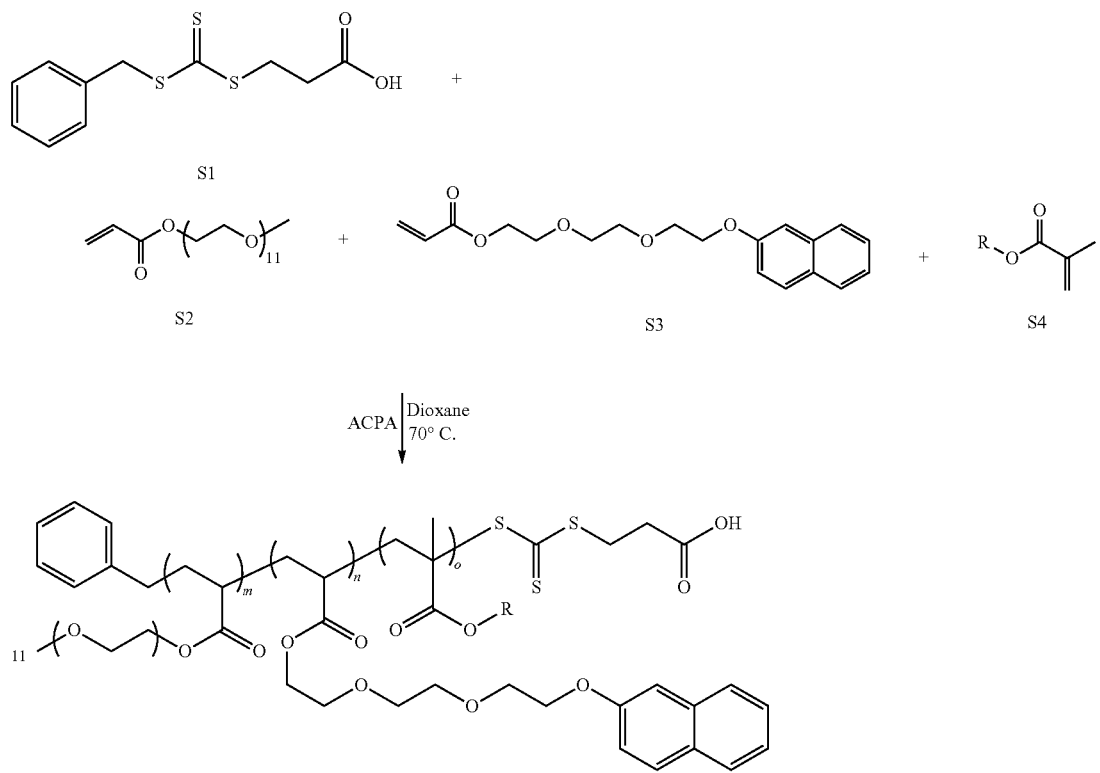

-continued

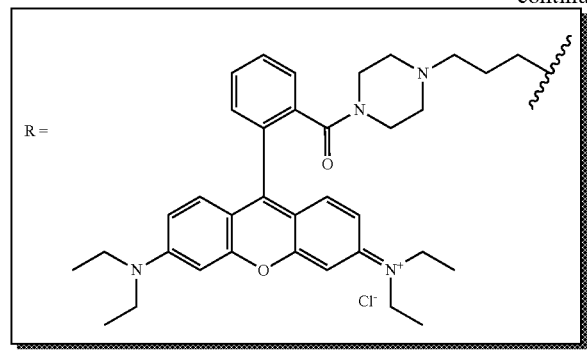

The excitation spectrum of the isolated Np-RD-pol is shown in FIG. 8.

Microfluidic Device

Detailed procedure of soft lithography for master fabrication was as reported by Duffy (see Duffy, et al. *Anal. Chem.* 1998, 70, 4974). The microfluidic device was fabricated by covering the master with a thoroughly stirred mixture of polydimethysiloxane (PDMS) and its curing agent (10% w/w) (Sylgard® 184, Dow Coring). The PDMS was allowed to solidify at 70° C. overnight before it was peeled off, while inlets and outlets were generated using a biopsy punch (Kai Medical, ID 1.0 mm). The enclosed microfluidic channels were formed by attaching the moulded PDMS replica onto microscope slides (Thermo Scientific) after exposure to an oxygen plasma (Femto, 40 kHz, 100 W, Diener Electronic). The microchannels of sealed devices were quickly rinsed with Aquapel (Duxback™) before washing with Flourinert FC-40 (3M).

Fabrication and Characterization of the Microcapsules

The fluorous oil phase and the appropriate dispersed phase solution were loaded into syringes (Hamilton, Gasligh®) with needles (Becton Dickinson, PrecisionGlide®) attached. The needles were fitted with a polyethylene tubing (Portex® Fine Bore, 0.38 mm ID, 1.09 mm OO). The syringes were mounted on syringe pumps (Harvard PHD 2000 Infusion), while the other end of the tubing was inserted into the appropriate inlets in the PDMS device. The devices were imaged in real time using an inverted microscope (IX71, Olympus) connected to a Phantom fast camera (V72, Vision Research). Still images and videos were recorded and analyzed using Phantom software. Droplet formation was initiated as oil was first pumped into the device at 200 µL/h to fill the appropriate channels. The aqueous dispersed phase was then pumped into the device at 10-90 µL/h depending on individual experiment. Fluorus surfactant (1% w/v) was dissolved in FC-40 oil and used as the carrier phase. In a typical experiment, the concentrations of the stock solutions of the reagents were 0.3 to 80 µM, making the final concentration $C_n$ of certain reagent in droplets further diluted based on its initial concentration ($C_0$), its flow rate Qn, and the total flow rate of all aqueous streams ($Q_T$) once encapsulated in droplets:

$$C_n = C_0 \times \frac{Q_n}{Q_T}$$

After formation, droplets were either collected in the PDMS reservoir downstream or transferred to a microscope slide (76×26 mm, 1.2 mm, Menzel-Glaser). Upon collection, droplets were allowed to dehydrate over time for the complete formation of microcapsules.

Example Detailed Preparation of Capsules

In a standard capsule fabrication experiment, an oil phase was introduced into the channel of the microfluidic device described above at a flow rate of 200 µL/h, which flow rate was kept constant. Aqueous phases were introduced into the channel at a total flow rate of 100 µL/h, where the individual flow rates were 50 µL/h for CB[8]1 (40 µM), 25 µL/h for $MV^{2+}$-AuNP 2 (0.4 µM), and 25 µL/h for Np-pol 3 (2.3 µM). Such combination of flow rates at the T-junction geometry of 40 µm (cross-section) generates discrete aqueous droplets in oil with a diameter of approximately 60 µm. Upon drying, the resulting stable individual capsules retain a diameter of approximately 25 µm. A sample of the microcapsules generated using above parameters was collected and the size (diameter) of the droplets was measured:

| Droplet number | Diameter/µm |
|---|---|
| 1 | 59.02 |
| 2 | 59.67 |
| 3 | 59.90 |
| 4 | 57.69 |
| 5 | 59.16 |
| 6 | 60.50 |
| 7 | 60.45 |
| 8 | 59.53 |
| 9 | 59.53 |
| 10 | 58.93 |
| 11 | 59.76 |
| 12 | 58.78 |
| 13 | 59.39 |
| 14 | 58.64 |
| 15 | 60.59 |
| 16 | 59.63 |
| 17 | 60.09 |
| 18 | 60.36 |
| 19 | 58.55 |
| 20 | 58.22 |

The size of the droplets and hence that of the capsules are subjective to change based the geometry of the T-junction and on the ratio of the flow rate of the continuous phase and the total flow rate of the dispersed phase (see, for example, Garstecki et al.). The effect of these factors is investigated and summarised in FIG. 8.

However, varying the flow rates of individual aqueous streams will not change the resulting size of the droplets as long as the overall flow rate of the aqueous streams remain in the same ratio to that of the oil phase. The graph below shows that while the overall droplet size varies depending on the ratio of oil flow rate to combined aqueous flow rate, the variation in the ratio of the flow rates of individual aqueous streams does not result in any significant change in the resulting droplet size distribution. The raw data are summarised in the table below.

| Ratio of individual aqueous flow rates | Ratio of oil flow rate to combined aqueous flow rate | Average of droplet diameter (μm) | Standard deviation |
|---|---|---|---|
|  | 1/1 | 70.62 | 0.98 |
| 25/25/50 | 2/1 | 59.43 | 1.03 |
|  | 4/1 | 50.50 | 0.17 |
|  | 8/1 | 41.03 | 0.64 |
|  | 1/1 | 70.25 | 0.68 |
| 33/33/34 | 2/1 | 59.40 | 0.75 |
|  | 4/1 | 50.29 | 0.38 |
|  | 8/1 | 42.60 | 0.22 |
|  | 1/1 | 69.47 | 0.87 |
| 40/30/30 | 2/1 | 59.85 | 0.52 |
|  | 4/1 | 50.49 | 0.24 |
|  | 8/1 | 42.53 | 0.32 |
|  | 1/1 | 70.62 | 0.98 |
| 60/20/20 | 2/1 | 59.35 | 0.82 |
|  | 4/1 | 50.46 | 0.24 |
|  | 8/1 | 42.91 | 0.39 |

Laser Scanning Confocal Microscopy Experiments and Analysis

The sample preparation involved initially collecting aqueous droplets in FC40 oil in a PDMS reservoir mounted on a microscope cover slide (22×50 mm, 0.17 mm, MenzelGlaser). The sample was imaged in the reservoir at different time intervals to capture capsules at different stages of dehydration. The LSCM measurements were carried out using a Leica TCS SP5 confocal microscope using a 63× objective (NA=1.4, Leica HCX PL APO Lambda blue) with water or oil (Leica Type F Immersion Fluid, $n_{23}$=1.518) used as the immersion medium depending on the experiment. Samples were illuminated with either 488 nm or 544 nm laser lines for exciting the FITC-dextran and the rhodamine-containing polymer respectively. The emission of FITC-dextrans, peaking at 520 nm (product data sheet) and the emission of Np-RD-pol, peaking at 582 nm (shown in FIG. 7), were collected over emission band passes of 550-540 nm and 560-650 nm respectively. The fluorescence images were analyzed and the intensity profiles obtained using the Leica software LAS AF 2.3.6.

Electron Microscopy

For the scanning electron microscopy (SEM), samples were prepared by dehydrating the capsules in a reservoir before transferring them to a vial and washed with fresh FC-40 oil twice by centrifugation. An oil suspension of dried capsules was deposited onto a silica wafer followed by gentle blow of nitrogen to remove the excess oil. Measurements were made and images recorded using a Leo 1530 variable pressure SEM and an InLens detector. For the transmission electron microscopy (TEM), similar sample preparation was performed by applying several drops of the oil suspension of the dried capsules onto a carbon coated copper TEM sample grid (400 mesh). Excess oil was removed by firstly drying at room temperature then in the oven (100° C.). Measurements and images were obtained using a JEOL 2000FX TEM under an accelerating voltage of 200 kV.

Andor Camera Setup and Fluorescence Permeability Analysis

Fluorescence images of microcapsules were recorded using an EM-CCO camera (Xion+, Andor Technologies model A247 from Pixelinkand) connected to an inverted microscope (IX 71, Olympus) operating in epifluorescence mode, mounted with an automatic microscope stage (ProScan II, Prior Scientific). A mercury lamp (U-LH100HG, Olympus) was installed for wide-spectrum illumination with FITCfilters and dichroics (BrightLine©, Semrock) fitted to separate the fluorescence excitation and emission light. A computer controlled shutter was added to the excitation path to reduce the time during which the specimen was excited upon to minimize photobleaching. The camera, the stage and the shutter were controlled by a custom-written software (LabVIEW 8.2, National Instruments), which was used to record and analyze bright field and fluorescence images.

The permeability of the microcapsules was analyzed by encapsulating FITC-dextrans of various molecular weight. The encapsulation was generated by introducing a separate stream of an aqueous solution of FITC-dextran (1-10 μM) online, by either adding a separate inlet channel in the device, or by incorporating the FITC-dextran solution with an existing aqueous solution. The flow rates were adjusted accordingly to generate a variety of concentrations of FITC-dextran in the microcapsule before the concentration for optimal imaging quality was obtained. The droplets were then allowed to dehydrate on glass slides completely as described previously and their bright field and fluorescent images were taken. The dried capsules were re-dispersed in $H_2O$ by covering the sample with a water drop and a microscope cover slide. Another set of bright field and fluorescent images were taken immediately after rehydration, while the permeability of the capsule was judged by the distribution of the FITC fluorescence relative to the location of the capsules.

To demonstrate the active and reduction-responsive release of the FITC-dextran, capsules were fabricated containing FITC-dextran (500 kDa) and dried on glass slides as described previously. The sample was placed in a clear chamber sealed with parafilm. Nitrogen was directed into the chamber to create an oxygen-free environment. The chamber was then mounted on the Andor microscope, and a few drops of an aqueous solution of excess sodium ditionite ($Na_2S_2O_4$) were applied over the dried capsules using a syringe. Fluorescent images of the capsules were taken every 30 min for 10 h.

SERS Measurements

All SERS experiments were performed on a Renishaw InVia Raman confocal microscope with a 100× (NA=0.85) objective in the backscattering geometry. The microcapsule samples for SERS were prepared by collecting and drying droplets on a glass slide. SERS spectra were acquired using either the 633 nm or the 785 nm laser line typically with an incident power of 0.015 mW and 0.20 mW, respectively, with an acquisition time ranging between 1 and 20 s. SERS image maps were collected using Streamline® scanning and took 2-20 min depending on the sample specific SERS enhancements and the acquisition conditions (including area) with typical pixel dwell times of 1-20 s. All measurements were performed at room temperature.

REFERENCES

All documents mentioned in this specification are incorporated herein by reference in their entirety.
Abraham et al. *Advanced Materials* 2008, 20, 2177
Ameloot et al. *Nat. Chem.* 2011, 3, 382
An et al. *Biomacromolecules* 2006, 7, 580
Andrieux et al. *Analytical Chemistry* 2002, 74, 5217
Anema et al. *Annual Review of Analytical Chemistry* 2011
Appel et al. *J. Am. Chem. Soc.* 2010, 132, 14251
Bush, M. E. et al. *J. Am. Chem. Soc.* 2005, 127, 14511
Caruso et al. *Science* 1998, 282, 1111
Cavalieri et al. *ACS Nano* 2009, 3, 234
Chiefari et al. *Macromolecules* 1998, 31, 5559
Comiskey et al. *Nature* 1998, 394, 253
Coulston et al. *Chem. Commun.* 2011, 47, 164
Cui et al. *Adv. Funct. Mater.* 2010, 20, 1625
De Cock et al. *Angew. Chem. Int. Ed.* 2010, 49, 6954
Donath et al. *Angew. Chem. Int. Ed.* 1998, 37, 2201
Duffy, et al. *Anal. Chem.* 1998, 70, 4974
Forster et al. *Journal of Raman Spectroscopy* 1982, 12, 36
Frens *Nature Phys. Sci.* 1973, 241, 20
Garstecki et al. *Lab Chip* 2006, 6, 437
Granath *Journal of Colloid Science* 1958, 13, 308
Gunther et al. *Lab Chip* 2006, 6, 1487
Hermanson et al. *Physical Chemistry Chemical Physics* 2007, 9, 6442
Huebner et al. *Lab Chip* 2008, 8, 1244
Holtze et al. *Lab Chip* 2008, 8, 1632
Jiao et al. *J. Am. Chem. Soc.* 2010, 132, 15734
Jiao et al. *Org. Lett.* 2011, 13, 3044
Kelly et al. *Journal of Physical Chemistry B* 2002, 107, 668
Kim et al. *J. Am. Chem. Soc.* 2000, 122, 540
Lagona et al. *Angew. Chem. Int. Ed.* 2005, 44, 4844
Link et al. *The Journal of Physical Chemistry B* 1999, 103, 4212
Martin et al. *Langmuir* 2010, 26, 7410
Mehvar *Journal of Con trolled Release* 2000, 69, 1
Moghaddam et al. *J. Am. Chem. Soc.* 2011, 133, 3570
Patra et al., *Langmuir* 2009, 25, 13852
Patra et al. *Chemistry—An Asian journal* 2010, 5, 2442
Peyratout et al. *Angew. Chem. Int. Ed.* 2004, 43, 3762
Priest et al. *Lab Chip* 2008, 8, 2182
Rauwald et al. *J. Phys. Chem.* 2010, 114, 8606
Theberge et al. *Angew. Chem. Int. Ed.* 2010, 49, 5846
Thorsen et al. *Phys. Rev. Lett.* 2001, 86, 4163
Utada et al. *Science* 2005, 308, 537
Wang et al., *Chemistry of Materials* 2008, 20, 419
WO 2009/071899.
Xu et al. *AlChE Journal* 2006, 52, 3005
Yang et al. *Lab Chip* 2009, 9, 961
Yang et al. *Angew. Chem.* 2011, 123, 497
Zhou et al. *Electrophoresis* 2009, 31, 2
Additionally
Coulston et al *Chem. Commun.* 2011, 47, 164
Danil de Namor et al., *Chem. Rev.* 1998, 98, 2495-2525
Dsouza et al. *Chem. Rev.* 2011, 111, 7941-7980
Frens *Nature Phys. Sci.* 1973, 241, 20
Gokel et al., *Chem. Rev.* 2004, 104, 2723-2750
Martin et al. *Langmuir* 2010, 26, 7410
Rekharsky et al. *Chem. Rev.* 1998, 98, 1875

The invention claimed is:

1. A capsule having a shell which is obtained from the complexation of a composition comprising a host and one or more building blocks having suitable host guest functionality thereby to form a supramolecular cross-linked network; wherein the host is cucurbituril and the one or more building blocks have suitable cucurbituril guest functionality, and the shell is obtained from the complexation of (a) a composition comprising cucurbituril and (1) or (2) or (b) a composition comprising a plurality of covalently linked cucurbituril and (1), (2) or (3), wherein:

(1) comprises a first building block covalently linked to a plurality of first cucurbituril guest molecules and a second building block covalently linked to a plurality of second cucurbituril guest molecules, wherein a first guest molecule and a second guest molecule together with cucurbituril are suitable for forming a ternary guest-host complex, (2) comprises a first building block covalently linked to a plurality of first cucurbituril guest molecules and a plurality of second cucurbituril guest molecules wherein a first and a second guest molecule together with cucurbituril are suitable for forming a ternary guest-host complex and optionally the composition further comprises a second building block covalently linked to one or more third cucurbituril guest molecules, one or more fourth cucurbituril guest molecules or both, wherein a third and a fourth molecule together with cucurbituril are suitable for forming a ternary guest-host complex, and/or the first and fourth molecules together with cucurbituril are suitable for forming a ternary guest-host complex, and/or the second and third molecules together with cucurbituril are suitable for forming a ternary guest-host complex, and (3) comprises a first building block covalently linked to a plurality of first cucurbituril guest molecules, wherein the first guest molecule together with the cucurbituril are suitable for forming a binary guest-host complex, optionally the composition further comprises a second building block covalently linked to one or more second. cucurbituril guest molecules, wherein the second guest molecule together with the cucurhituril are suitable for forming a binary guest-host complex.

2. The capsule of claim 1, wherein the shell is obtained from the complexation of a composition comprising cucurbituril and (1) or (2).

3. The capsule of claim 2, wherein the shell is obtained from the complexation of a composition comprising cucurbituril and (1).

4. The capsule of claim 1, wherein the cucurbituril is selected from CB [8] and variants and derivatives thereof.

5. The capsule of claim 4, wherein the cucurbituril is CB[8].

6. The capsule of claim 4, wherein the cucurbituril forms a ternary complex with a first guest molecule and a second guest molecule, and the first and second guest molecules are selected from the following pairs:
viologen and naphthol;
viologen and dihydroxybenzene;
viologen and tetrathiafulvalene;
viologen and indole;
methylviologen and naphthol;
methylviologen and dihydroxybenzene;
methylviologen and tetrathiafulvalene;
methylviologen and indole;
N,N'-dimethyldipyridyliumylethylene and naphthol;
N,N'-dimethyldipyridyliumylethylene and dihydroxybenzene;

N,N'-dimethyldipyridyliumylethylene and tetrathiafulvalene;
N,N'-dimethyldipyridyliumylethylene and indole;
2,7-dimethyldiazapyrenium and naphthol;
2,7-dimethyldiazapyrenium and dihydroxybenzene;
2,7-dimethyldiazapyrenium and tetrathiafulvalene; and
2,7-dimethyldiazapyrenium and indole.

7. The capsule of claim 1, wherein the first building block is a polymeric molecule.

8. The capsule of claim 7, wherein the polymeric molecule is or comprises a poly(meth)acrylate-, a polystyrene- and/or a poly(meth)acrylamide polymer.

9. The capsule of claim 7, wherein the polymeric molecule comprises a detectable label.

10. The capsule of claim 1, wherein the second building block is a particle.

11. The capsule of claim 10, wherein the particle is or comprises gold or silver or mixtures thereof.

12. The capsule according to claim 1, wherein the capsule size is in range from 10 to 100µm in diameter.

13. The capsule according to claim 1, wherein the capsule diameter has a relative standard deviation (RSD) of at most 10%.

14. The capsule according to claim 1, wherein the shell pore size is in range 1 to 20 nm.

15. The capsule according to claim 1, wherein the capsule encapsulates a component.

16. The capsule according to claim 15, wherein the component is a biological molecule.

17. A method for the preparation of the capsule having a shell according to claim 1, the method comprising the step of:
(i) contacting a flow of a first phase and a flow of a second phase in a channel, thereby to generate in the channel a dispersion of discrete regions of the second phase in the first phase, wherein the second phase comprises cucurbituril and one or more building blocks having suitable cucurbituril guest functionality suitable to form a supramolecular cross-linked network, thereby to form a capsule shell within the discrete region, wherein the first and second phases are immiscible; wherein
the host is cucurbituril and the one or more building blocks have suitable cucurbituril guest functionality, and
the shell is obtained from the complexation of (a) a composition comprising cucurbituril and (1) or (2) or (b) a composition comprising a plurality of covalently linked cucurbituril and (1), (2) or (3), wherein:
(1) comprises a first building block covalently linked to a plurality of first cucurbituril guest molecules and a second building block covalently linked to a plurality of second cucurbituril guest molecules, wherein a first guest molecule and a second guest molecule together with cucurbituril are suitable for forming a ternary guest-host complex,
(2) comprises a first building block covalently linked to a plurality of first cucurbituril guest molecules and a plurality of second cucurbituril guest molecules, wherein a first and a second guest molecule together with cucurbituril are suitable for forming a ternary guest-host complex and optionally the composition further comprises a second building block covalently linked to one or more third cucurbituril guest molecules, one or more fourth cucurbituril guest molecules or both, wherein a third and a fourth molecule together with cucurbituril are suitable for forming a ternary guest-host complex, and/or the first and fourth molecules together with cucurbituril are suitable for forming a ternary guest-host complex, and/or the second and third molecules together with cucurbituril are suitable for forming a ternary guest-host complex, and
(3) comprises a first building block covalently linked to a plurality of first cucurbituril guest molecules, wherein the first guest molecule together with the cucurbituril are suitable for forming a binary guest-host complex, optionally the composition further comprises a second building block covalently linked to one or more second cucurbituril guest molecules, wherein the second guest molecule together with the cucurbituril are suitable for forming a binary guest-host complex.

18. The method of claim 17, wherein the composition further comprises a second building block covalently linked to one or more second cucurbituril guest molecules, wherein the second guest molecule together with the cucurbituril are suitable for forming a binary guest-host complex.

19. The method of claim 18 wherein the second phase comprises cucurbituril and (1) or (2).

20. The method of claim 19, wherein the second phase comprises cucurbituril and (1).

21. The method of claim 17, wherein the cucurbituril is selected from CB[8] and variants and derivatives thereof.

22. The method of claim 21, wherein the cucurbituril is CB[8].

23. The method of claim 21, wherein the cucurbituril forms a ternary complex with a first guest molecule and a second guest molecule, and the first and second guest molecules are selected from the following pairs:
viologen and naphthol;
viologen and dihydroxybenzene;
viologen and tetrathiafulvalene;
viologen and indole;
methylviologen and naphthol;
methylviologen and dihydroxybenzene;
methylviologen and tetrathiafulvalene;
methylviologen and indole;
N,N'-dimethyldipyridyliumylethylene and naphthol;
N,N'-dimethyldipyridyliumylethylene and dihydroxybenzene;
N,N'-dimethyldipyridyliumylethylene and tetrathiafulvalene;
N,N'-dimethyldipyridyliumylethylene and indole;
2,7-dimethyldiazapyrenium and naphthol;
2,7-dimethyldiazapyrenium and dihydroxybenzene;
2,7-dimethyldiazapyrenium and tetrathiafulvalene; and
2,7-dimethyldiazapyrenium and indole.

24. The method of claim 17, wherein the first building block is a polymeric molecule.

25. The method of claim 24, wherein the polymeric molecule is or comprises a poly(meth)acrylate-, a polystyrene- and/or a poly(meth)acrylamide polymer.

26. The method of claim 24, wherein the polymeric molecule comprises a detectable label.

27. The method of claim 17, wherein the second building block, is a particle.

28. The method of claim 27, wherein the particle is or comprises gold or silver or mixtures thereof.

29. The method of claim 17, wherein the second phase is an aqueous phase and the first phase is a water immiscible phase.

30. The method of claim 17, wherein the second phase further comprises a component for encapsulation, and the step (i) provides a capsule having a shell encapsulating the component.

31. The method of claim 17, wherein the method further comprises the step of (ii) collecting the outflow from the channel, thereby to obtain a droplet, which contains a capsule.

32. The method of claim 31, further comprising the step of drying the capsule obtained in step (ii).

33. A method of delivering a component to a location, the method comprising the steps of:
   (i) providing a capsule having a shell encapsulating a component, as defined in claim 15;
   (ii) delivering the capsule to a target location;
   (iii) releasing the component from the shell.

* * * * *